(12) United States Patent
Holson et al.

(10) Patent No.: US 8,691,875 B2
(45) Date of Patent: Apr. 8, 2014

(54) SOLID FORMS OF TACEDINALINE

(75) Inventors: Edward Holson, Newton, MA (US);
Florence F. Wagner, Ashland, MA (US);
G. Patrick Stahly, West Lafayette, IN (US)

(73) Assignee: Broad Institute, Inc., Cambridge, MA (US)

( * ) Notice: Subject to any disclaimer, the term of this patent is extended or adjusted under 35 U.S.C. 154(b) by 0 days.

(21) Appl. No.: 13/620,772

(22) Filed: Sep. 15, 2012

(65) Prior Publication Data

US 2013/0102677 A1   Apr. 25, 2013

Related U.S. Application Data

(62) Division of application No. 13/174,780, filed on Jul. 1, 2011, now abandoned.

(51) Int. Cl.
| | | |
|---|---|---|
| *A61K 31/167* | (2006.01) | |
| *C07C 237/40* | (2006.01) | |
| *A61P 25/28* | (2006.01) | |
| *A61P 25/00* | (2006.01) | |
| *A61P 25/18* | (2006.01) | |
| *A61P 25/22* | (2006.01) | |
| *A61P 25/30* | (2006.01) | |

(52) U.S. Cl.
USPC ........................... 514/616; 514/619; 564/157

(58) Field of Classification Search
None
See application file for complete search history.

(56) References Cited

U.S. PATENT DOCUMENTS

| | | |
|---|---|---|
| 5,137,918 A | 8/1992 | Weiershausen et al. |
| 6,469,058 B1 | 10/2002 | Grove et al. |
| 2011/0224303 A1* | 9/2011 | Tsai et al. ..................... 514/616 |
| 2013/0102677 A1 | 4/2013 | Holson et al. |

FOREIGN PATENT DOCUMENTS

| | | |
|---|---|---|
| EP | 1 273 296 B1 | 11/2003 |
| WO | WO 2009/076234 A2 | 6/2009 |
| WO | WO 2011/053876 A1 | 5/2011 |

OTHER PUBLICATIONS

Byrn, S. et al., "Pharmaceutical Solids: A Strategic Approach to Regulatory Considerations", *Pharmaceutical Research*, vol. 12, No. 7, pp. 945-954 (1995).
Gediya L.K., et al., "Improved synthesis of histone deacetylase inhibitors (HDIs) (MS-275 and CI-994) and inhibitory effects of HDIs alone or in combination with RAMBAs or retinoids on growth of human LNCaP prostate cancer cells and tumor xenografts", *Bioorganic & Medicinal Chemistry* 16, pp. 3352-3360 (2008).
Riva, L. et al., "Pharmacokinetics and Cerebrospinal Fluid Penetration of Cl-994 (N-Acetyldinaline) in the Nonhuman Primate", *Clinical Cancer Research*, vol. 6, pp. 994-997 (2000).
Thomas, M. et al., "Synthesis and biological evaluation of glucuronide prodrugs of the histone deacetylase inhibitor Cl-994 for application in selective cancer chemotherapy", *Bioorganic & Medicinal Chemistry*, 16, pp. 8109-8116 (2008).
International Preliminary Report on Patentability, International Application No. PCT/US2011/042728, issued Jan. 8, 2013.
Written Opinion, International Application No. PCT/US2011/042728, mailed Nov. 29, 2011.

* cited by examiner

*Primary Examiner* — Anna Pagonakis
(74) *Attorney, Agent, or Firm* — Vedder Price PC; Thomas J. Kowalski; Samuel H. Megerditchian

(57) ABSTRACT

Novel solid forms of tacedinaline (4-(acetylamino)-N-(2-aminophenyl)benzamide), including crystalline tacedinaline Forms A, B, and D, a novel crystalline tacedinaline TFA salt, and amorphous tacedinaline, are disclosed. Pharmaceutical compositions comprising crystalline tacedinaline Forms A, B, and D, the novel crystalline tacedinaline TFA salt, and/or amorphous tacedinaline, and methods of treating various conditions by administering those novel solid forms, are also disclosed.

4 Claims, 66 Drawing Sheets

SOLID FORMS OF TACEDINALINE

CROSS-REFERENCE TO RELATED APPLICATION

This is a division of application Ser. No. 13/174,780, filed Jul. 1, 2011, which has been allowed, incorporated herein by reference.

TECHNICAL FIELD

The invention relates to novel solid forms of tacedinaline, pharmaceutical compositions comprising the novel solid forms, and methods of treating and/or preventing various conditions by administering the novel solid forms.

BACKGROUND

The solid form (i.e., the crystalline or amorphous form) of a pharmaceutical compound can be important relative to its pharmacological properties and development as a viable active pharmaceutical ingredient ("API").

Pharmaceutical products are often formulated from crystalline compounds because crystalline materials may provide higher levels of purity and resistance to physical and chemical instabilities under ambient conditions, relative to amorphous forms. Crystalline forms of a compound may, in some cases, offer advantages over amorphous forms, such as improved solubility, stability, processing improvements, etc., and different crystalline forms (e.g. polymorphs of the compound) may offer greater or lesser advantages over one another. However, crystalline forms of a compound are not predictable, and in fact, are not always possible. It is a well-accepted principle that the formation of a new polymorphic or crystalline form (e.g. a new crystalline salt form) of a compound is totally unpredictable, and until a particular polymorph is prepared, there is no way to know whether it might exist, how to prepare it, or what its properties might be. Bernstein, J. *Polymorphism in Molecular Crystals*. New York: Oxford University Press, 9 (2002).

Unlike a crystalline solid, which has an orderly array of unit cells in three dimensions, amorphous forms lack long-range order because molecular packing is more random. As a result, amorphous organic compounds tend to have different properties than their crystalline counterparts. For example, amorphous compounds often have greater solubility than crystalline forms of the same compound. Thus, by way of example only, in pharmaceutical formulations whose crystalline forms are poorly soluble, amorphous forms may present attractive formulation options. As such, amorphous APIs may be used to improve physical and chemical properties of drugs, such as, for example, dissolution and bioavailability.

Solid forms of a compound, including both crystalline and amorphous forms, are of particular interest to the pharmaceutical industry, for example to those involved in the development of suitable dosage forms. If the solid form of the API (e.g. the crystalline polymorphic form or amorphous form) is not held constant during clinical or stability studies, the exact dosage form used or studied may not be comparable from one lot to another. In addition, regulatory agencies require solid form characterization and control of the API for approval. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies. As such, finding the right conditions to obtain a particular solid form of the desired API (e.g. a particular crystalline polymorphic form or an amorphous form), with pharmaceutically acceptable properties, is critical to drug development, but can take significant time, resources, and effort.

Tacedinaline, 4-(acetylamino)-N-(2-aminophenyl)benzamide, (shown below) is a known API useful for treating and/or preventing a variety of conditions, such as, for example, combating neoplastic diseases, and is recognized as an HDAC inhibitor.

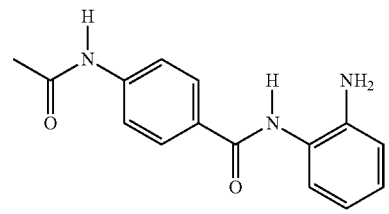 [SMILES: CC(=O)Nc1ccc(C(=O)Nc2ccccc2N)cc1]

For example, tacedinaline has positive indications for the treatment of prostate cancer. The preparation and pharmacologic activity of tacedinaline are described in, for example, U.S. Pat. No. 5,137,918, WO 2009/076234, Gediya, L. K. et al., *Bioorganic & Medicinal Chemistry* 2008, 16, 3352-3360; and Thomas, M. et al., *Bioorganic & Medicinal Chemistry* 2008, 16, 8109-8116, all of which are incorporated herein by reference.

While therapeutic efficacy is a primary concern for a therapeutic agent such as tacedinaline, as discussed above the solid form of a pharmaceutical drug candidate is also important. For example, each solid form of a drug candidate can have different solid state (physical and chemical) properties. The differences in physical properties exhibited by a different solid form of an API, such as a polymorph of the original compound, can affect pharmaceutical parameters such as storage stability, compressibility and density, all of which may be important in formulation and product manufacturing, and solubility and dissolution rates, which may be important factors in determining bioavailability. Because these practical physical properties can be influenced by the solid form of the API, they can significantly impact the selection of a compound as an API, the ultimate pharmaceutical dosage form, the optimization of manufacturing processes, and absorption in the body. Moreover, finding the most adequate form for further drug development can reduce the time and the cost of that development. It may also be beneficial to identify and characterize additional crystal forms so that they may be recognized if they appear during drug development and/or manufacturing.

Obtaining pure solid forms, then, can be extremely useful in drug development, as it generally permits better characterization of the drug candidate's chemical and physical properties. Crystalline forms often have more favorable chemical and physical properties than amorphous forms of the same compound. As such, one or more crystalline forms may possess more favorable pharmacology than amorphous forms or be easier to process, or may have better storage stability. Similarly, one crystalline form may possess more favorable pharmacology, may be easier to process, or may have better storage stability than another, or than an amorphous form, or vice versa.

One such physical property is a pharmaceutical compound's dissolution rate in aqueous fluid. The rate of dissolution of an API in a patient's stomach fluid may have therapeutic consequences since it impacts the rate at which an orally administered active ingredient may reach the patient's bloodstream.

Another such physical property is thermodynamic stability. The thermodynamic stability of an active ingredient may have consequences on the manufacturing process and storage stability of the API and/or the formulation.

A crystalline form of a compound generally possesses distinct crystallographic and spectroscopic properties when compared to other crystalline forms having the same chemical composition. Crystallographic and spectroscopic properties of the particular form are typically measured by one or more techniques such as x-ray powder diffraction (XRPD), single crystal x-ray crystallography, solid state NMR spectroscopy, infrared spectroscopy (IR), or Raman spectroscopy, among other techniques. A particular solid form of a compound may often exhibit distinct thermal behavior as well. Thermal behavior is measured in the laboratory by such techniques as capillary melting point, thermogravimetric analysis (TGA), and differential scanning calorimetry (DSC).

Referenced above, U.S. Pat. No. 5,137,918 describes the synthesis and basic activities of a family of compounds including tacedinaline. The tacedinaline disclosed therein is reported as having a melting point of 243.7° C.

Accordingly, there is a need in the art to identify novel solid forms of tacedinaline, particularly those having advantageous chemical and/or physical properties. This invention answers those needs by providing novel solid forms of tacedinaline, including forms having improved properties.

SUMMARY

In accordance with various embodiments of the invention and after extensive experimentation are disclosed novel crystalline forms of tacedinaline, including the three forms referred to herein as Forms A, B, and D, and a novel crystalline tacedinaline TFA salt form.

The invention in various embodiments also relates to pharmaceutical compositions and formulations comprising the novel crystalline forms, and methods of treating and/or preventing various conditions by administering the novel crystalline forms.

In further embodiments, the invention relates to a novel amorphous form of tacedinaline, as well as pharmaceutical compositions and formulations comprising the novel amorphous form, and methods of treating and/or preventing various conditions by administering the novel amorphous form.

As used herein, the term "polymorph" refers to different crystalline forms of the same compound and other solid state molecular forms, including pseudopolymorphs. The terms "pseudopolymorph" and "pseudomorph" as used herein are interchangeable and are meant to include hydrates (i.e., water present in the crystalline structure) and solvates (i.e., solvents other than water) of the compound, of both a fixed or stoichiometric and variable nature. Different crystalline forms, such as polymorphs, have different crystal structures due to a different packing of the molecules in the lattice. This results in a different crystal symmetry and/or unit cell parameters which directly influences the physical properties of the form, including X-ray characteristics (both single-crystal and XRPD) of crystals or powders. A different polymorph, for example, will in general diffract at a different set of angles and will give different values for the intensities. Therefore, when available, X-ray techniques can be used to identify different polymorphs, or a solid form that comprises more than one polymorph, generally in a reproducible and reliable way. S. Byrn et al., "Pharmaceutical Solids: A Strategic Approach to Regulatory Considerations," *Pharmaceutical Research*, Vol. 12, No. 7, p. 945-954, 1995; J. K. Haleblian and W. McCrone, "Pharmaceutical Applications of Polymorphism," *Journal of Pharmaceutical Sciences*, Vol. 58, No. 8, p. 911-929, 1969.

As used herein, the term "XRPD" refers to x-ray powder diffraction. Unless otherwise noted, XRPD analyses were performed either on a Scintag $X_1$ Advanced Diffraction system or a Rigaku Smart Lab X-ray diffraction system.

The Scintag $X_1$ Advanced Diffraction system is equipped with a Vortex Silicon Multi-Cathode detector. Data were collected using Cu Kα radiation. The X-ray tube voltage and amperage were set to 45 kV and 40 mA, respectively. The slits used were a 1 mm divergence slit, a 2 mm tube scatter slit, a 0.5 mm detector scatter slit, and a 0.3 mm reference slit. Data were collected in continuous mode from 2 to 40° 2θ using a 0.04 degree step and a 2 second collection time per step. Each specimen was prepared for analysis by placing it in the 1-mm deep, round well of a stainless steel holder and leveling the surface with a glass slide.

The Rigaku Smart-Lab X-ray diffraction system was configured for reflection Bragg-Brentano geometry using a line source X-ray beam. The x-ray source is a Cu Long Fine Focus tube was operated at 40 kV and 44 ma. That source provides an incident beam profile at the specimen that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the specimen itself acting as the focusing component in the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0° Soller slits in both the incident and diffracted beam paths. Each powder specimen was prepared in a low background Si holder using light manual pressure to keep the sample surface flat and level with the reference surface of the sample holder. The single crystal Si low background holders have a small circular recess (7 mm diameter and about 1 mm depth) that holds between 5 and 10 mg of powdered material. The standard measurement range was from 2 to 40° 2θ using a continuous scan of 3° 2θ per minute with an effective step size of 0.02° 2θ.

As used herein, "IR" refers to infrared spectroscopy. Unless otherwise noted, IR spectra were obtained on a Nicolet 6700 FT-IR system. Samples were analyzed using a Nicolet SMART iTR attenuated total reflectance device.

As used herein, "mp" refers to melting point. Melting points were determined on a Stuart SMP3 apparatus that was calibrated using a caffeine USP melting point standard. A ramp rate of 1° C./minute was used.

As used herein, the term "DSC" refers to differential scanning calorimetry. Unless otherwise noted, DSC data disclosed herein were obtained using a TA Instruments 2920 instrument. Samples were prepared in crimped aluminum pans and kept under a flow of nitrogen during analysis. The heating rate was 10° C./minute.

As used herein, the term "TGA" refers to thermogravimetric analysis. Unless otherwise noted, TGA data disclosed herein were obtained using TA Instruments 2050 instrument. Samples were kept under a flow of nitrogen during analysis. The heating rate was 10° C./minute.

As used herein, the term "$^1$H-NMR" refers to proton nuclear magnetic resonance spectroscopy. Solution $^1$H NMR data disclosed herein were acquired on a Bruker 300 (300 MHz $^1$H) spectrometer. Proton chemical shifts are reported in ppm, referenced to the NMR solvent. Unless otherwise indicated, NMR data were collected at 25° C.

As used herein, "LC/MS" refers to tandem liquid chromatography/mass spectrometry. LC/MS data referenced herein were acquired on a Waters 2795 Alliance HPLC coupled with a Waters 2996 Photodiode Array Detector and a Waters ZQ Mass Spectrometer. The column was an XBridge 4.6×30 mm, 3.5 μm, using a 5 to 95% acetonitrile/water gradient containing 0.01% formic acid over 2.5 minutes. As used herein, "UPLC/MS" refers to tandem Ultra Performance Liquid Chromatography/Mass Spectrometer. UPLC/MS data referenced herein was acquired on a Waters Acquity UPLC coupled with a Waters Acquity PDA Detector and a Waters SQ Mass Spectrometer (single quadrupole). The column was an Acquity BEH C18 1.0×50 mm, 1.7 um, using 5 to 95% acetonitrile/water gradient containing 0.05% trifluoroacetic acid (water) and 0.1% triflouroacetic acid (acetonitrile) over 15 minutes.

Single crystal x-ray data reported herein were acquired at low temperature (150 K) on a Rigaku Rapid II equipped with confocal optics. Crystals were mounted on a fiber in a random orientation. Additional details are provided below.

As used herein with respect to the various analytical techniques described herein and data generated therefrom, the terms "substantially the same as" or "substantially similar to" is meant to convey that a particular set of analytical data is, within acceptable scientific limits, sufficiently similar to that disclosed herein such that one of skill in the art would appreciate that the crystal form of the compound is the same as that of the present invention. One of skill in the art would appreciate that certain analytical techniques, such as, for example, XRPD, $^1$H-NMR, LC/MS, IR, DSC, TGA, and Raman, will not produce exactly the same results every time due to, for example, instrumental variation, sample preparation, scientific error, etc. By way of example only, XRPD results (e.g., peak locations, intensities, and/or presence) may vary slightly from sample to sample, despite the fact that the samples are, within accepted scientific principles, the same crystalline form, and this may be due to, for example, preferred orientation or varying solvent or water content. It is well within the ability of those skilled in the art, looking at the data as a whole, to appreciate whether such differences indicate the same or a different form, and thus determine whether analytical data being compared to those disclosed herein are or are not substantially the same or similar to the solid form it is being compared with.

In this regard, and as is commonly practiced within the scientific community, it is not intended that the exemplary analytical data of the novel polymorphic forms of tacedinaline disclosed herein be met literally in order to determine whether comparative data represent the same form as those disclosed and claimed herein, such as, for example, whether each and every peak of an exemplary XRPD pattern of the novel polymorphic forms of tacedinaline disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form than the novel polymorphic forms of tacedinaline disclosed herein.

It is to be understood that both the foregoing general description and the following detailed description are exemplary and explanatory only and are not restrictive of the invention, as claimed.

DETAILED DESCRIPTION

In various embodiments, the invention relates to novel crystalline Forms A, B, and D of tacedinaline, as well as novel amorphous tacedinaline and a novel crystalline tacedinaline TFA salt form. Exemplary methods of preparing these novel solid forms are found in the examples below.

In further embodiments, the invention relates to pharmaceutical compositions and formulations comprising the novel solid forms of tacedinaline, and methods of treating and/or preventing various conditions by administering the novel solid forms.

Crystalline Tacedinaline Form A

Figure 1A:
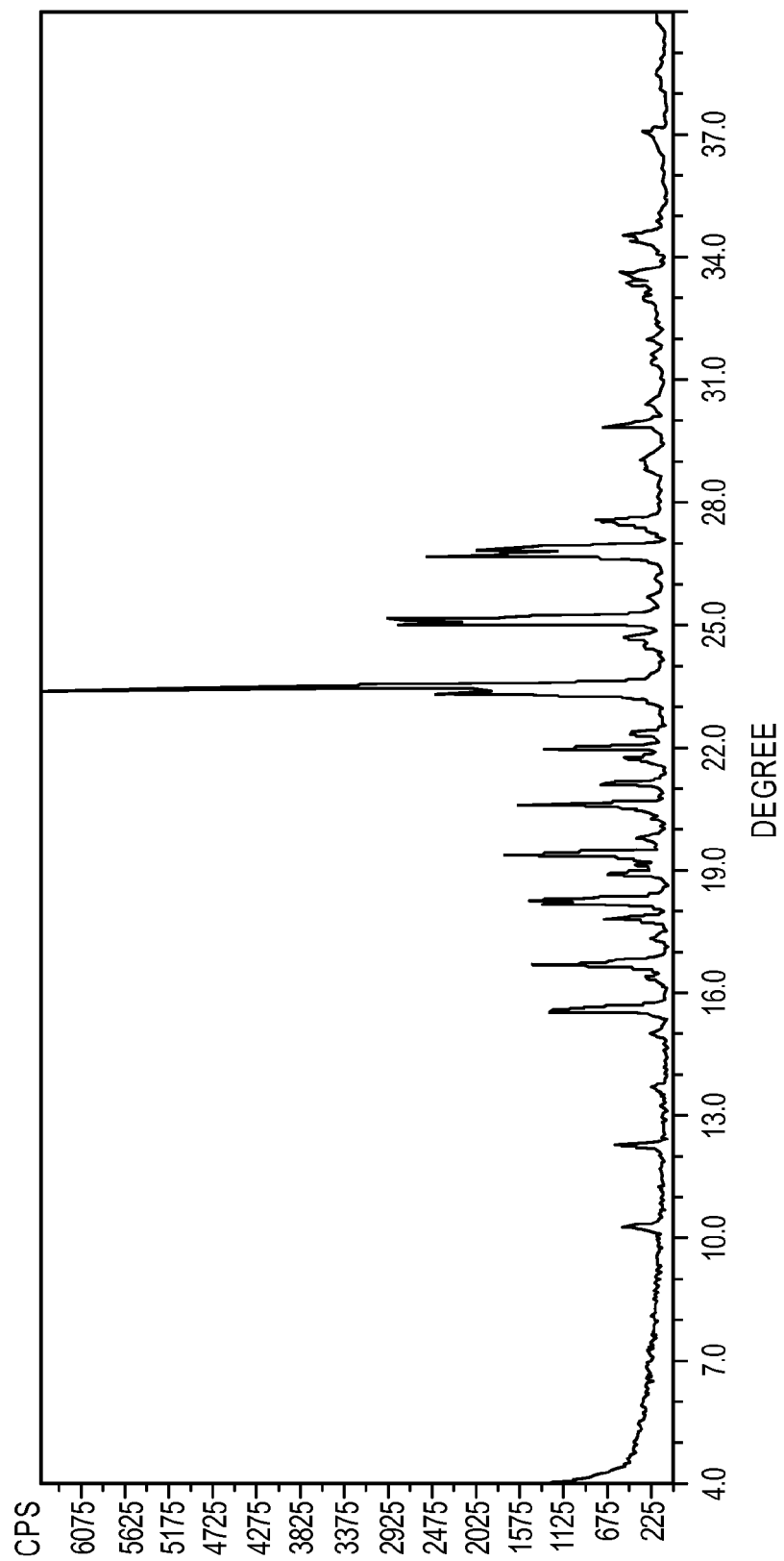
FIGS. 1A and 1B show exemplary XRPD patterns of crystalline tacedinaline Form A.
Figure 1B:
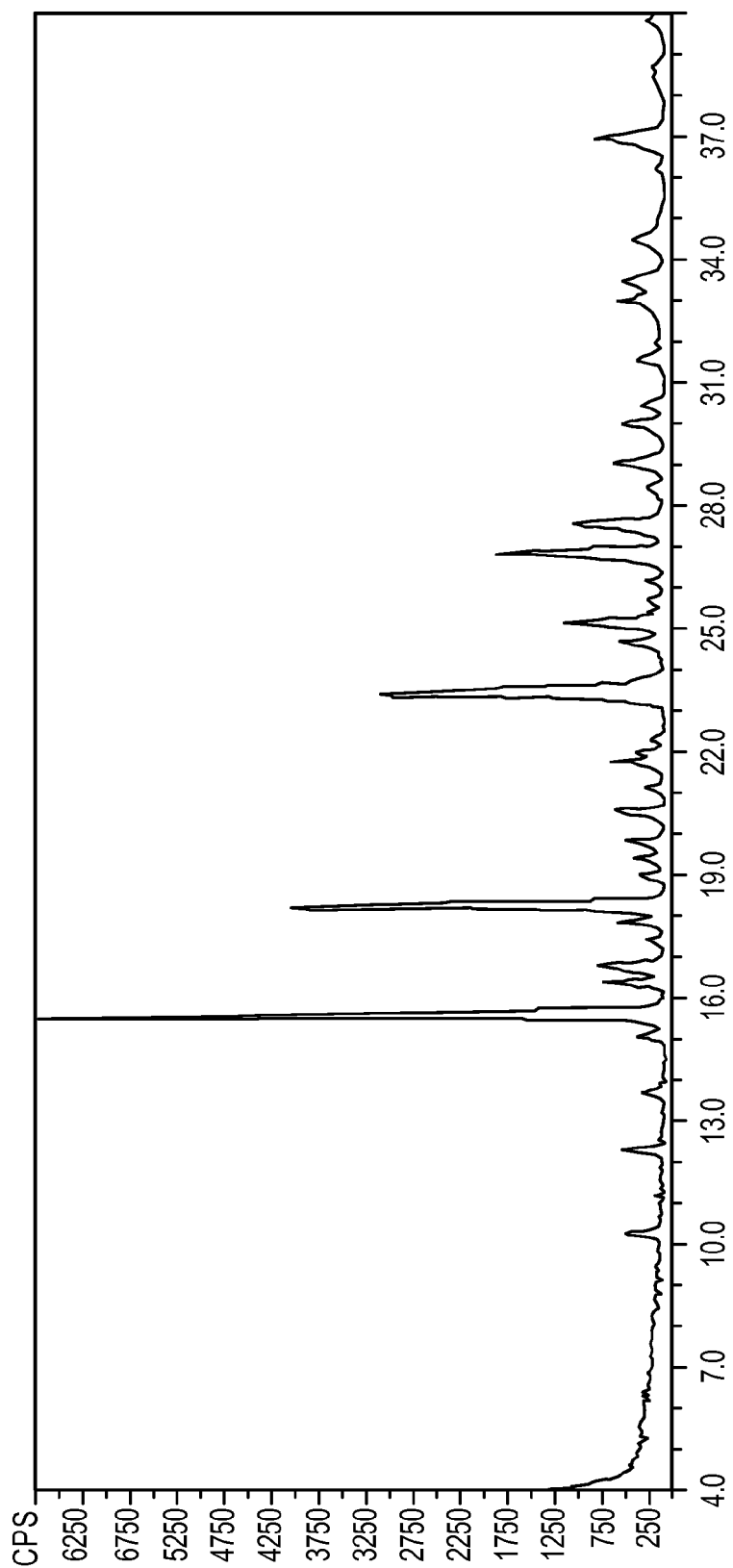
Figure 2:
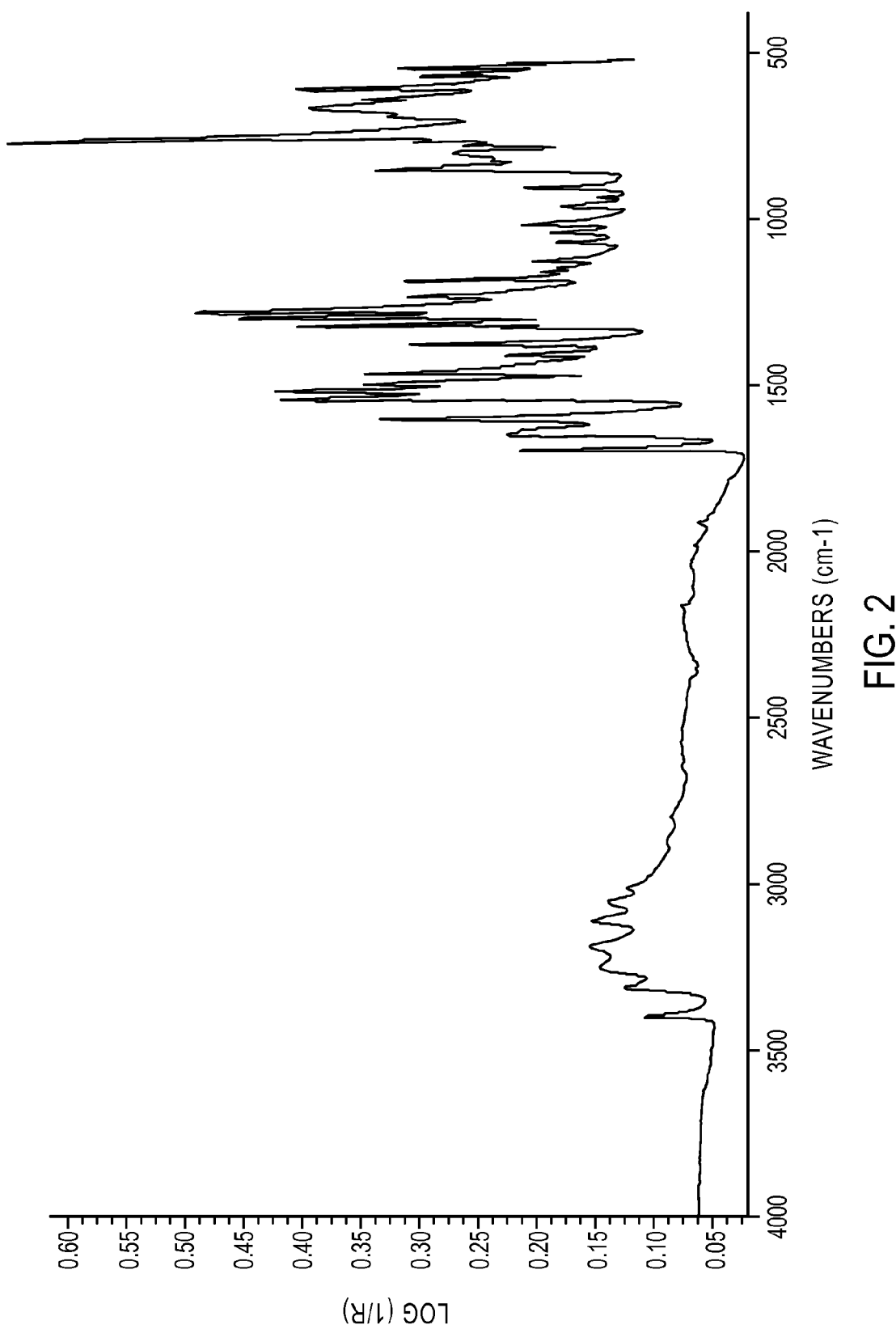
FIG. 2 shows an exemplary IR spectrum of an embodiment of crystalline tacedinaline Form A.

Crystalline tacedinaline Form A was obtained in a crystalline solid form that is characterized by a unique XRPD pattern substantially as shown in FIGS. 1A and 1B, and a unique IR spectrum substantially as shown in FIG. 2. Crystalline tacedinaline Form A was found to be an anhydrate, as suggested by the representative TGA plot in FIG. 3, exhibiting no weight loss prior to decomposition. The anhydrous nature of tacedinaline Form A was confirmed by the single crystal structure. Tacedinaline Form A has a melting temperature in the range of about 239-240° C., as found by visual determination, and exhibits a corresponding endothermic event at about 247° C., as shown by the representative DSC trace in FIG. 4. Subsequent to this endothermic event, tacedinaline Form A undergoes a thermally activated dehydrative intramolecular cyclization to form N-(4-(1-H-benzo[d]imidazol-2-yl)acetamide, which exhibits a characteristic endothermic event at about 310° C.

An exemplary listing of representative XRPD peaks of an embodiment of tacedinaline Form A can be found in Table 1. An exemplary listing of representative IR peaks of an embodiment of tacedinaline Form A can be found in Table 2.

Crystalline tacedinaline Form A exhibits improved properties relative to other forms of tacedinaline, including that disclosed in the art (Form C). For example, Form A has improved thermal stability relative to tacedinaline Form C, which contains methanol and may be undesirable in various embodiments. Additionally, Form A is more thermodynamically stable under certain conditions relative to Forms B and D, as shown in Examples 11 and 12.

TABLE 1

| Form A |
| --- |
| Degrees 2θ |
| 10.28 |
| 12.31 |
| 13.70 |
| 15.69 |
| 16.44 |
| 17.90 |
| 18.36 |
| 19.04 |
| 19.45 |
| 19.90 |
| 23.55 |
| 24.78 |
| 25.25 |
| 26.95 |
| 27.67 |

TABLE 2

| Form A |
| --- |
| Reciprocal cm |
| 3396.2 |
| 3310.3 |
| 3247.5 |
| 3185.8 |
| 3108.0 |
| 3048.5 |
| 1690.9 |
| 1642.1 |
| 1594.2 |
| 1528.3 |
| 1504.2 |
| 1485.6 |
| 1456.5 |
| 1404.3 |
| 1370.4 |
| 1308.6 |
| 1283.6 |
| 1265.0 |
| 1224.6 |
| 1177.5 |
| 1123.5 |
| 1069.5 |
| 1037.3 |
| 1016.1 |
| 1009.5 |
| 904.3 |
| 848.1 |
| 796.7 |
| 745.9 |
| 656.9 |
| 601.3 |

Crystalline Tacedinaline Form B

Figure 7A:
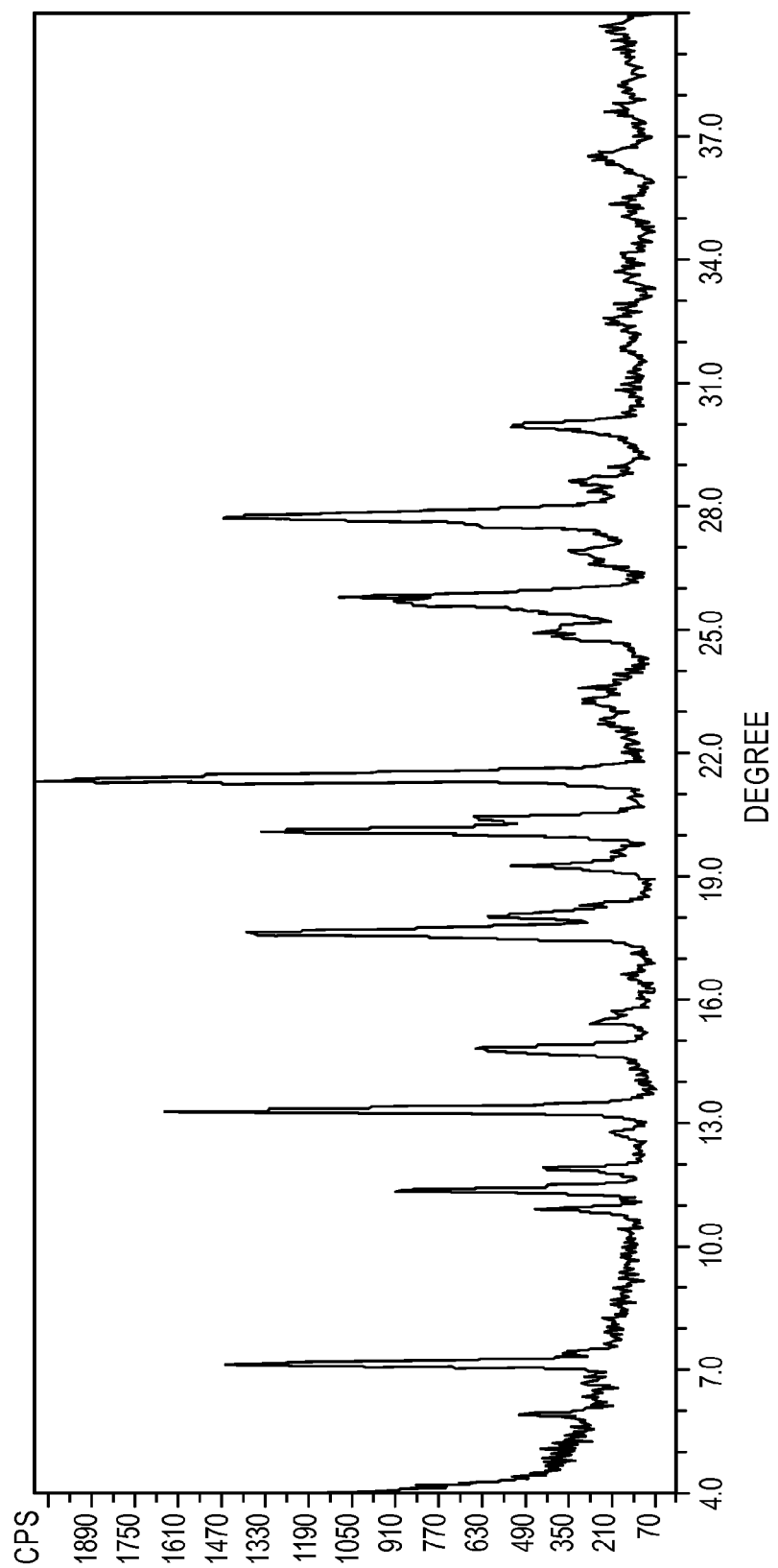
FIGS. 7A and 7B show exemplary XRPD patterns of crystalline tacedinaline Form B.
Figure 7B:
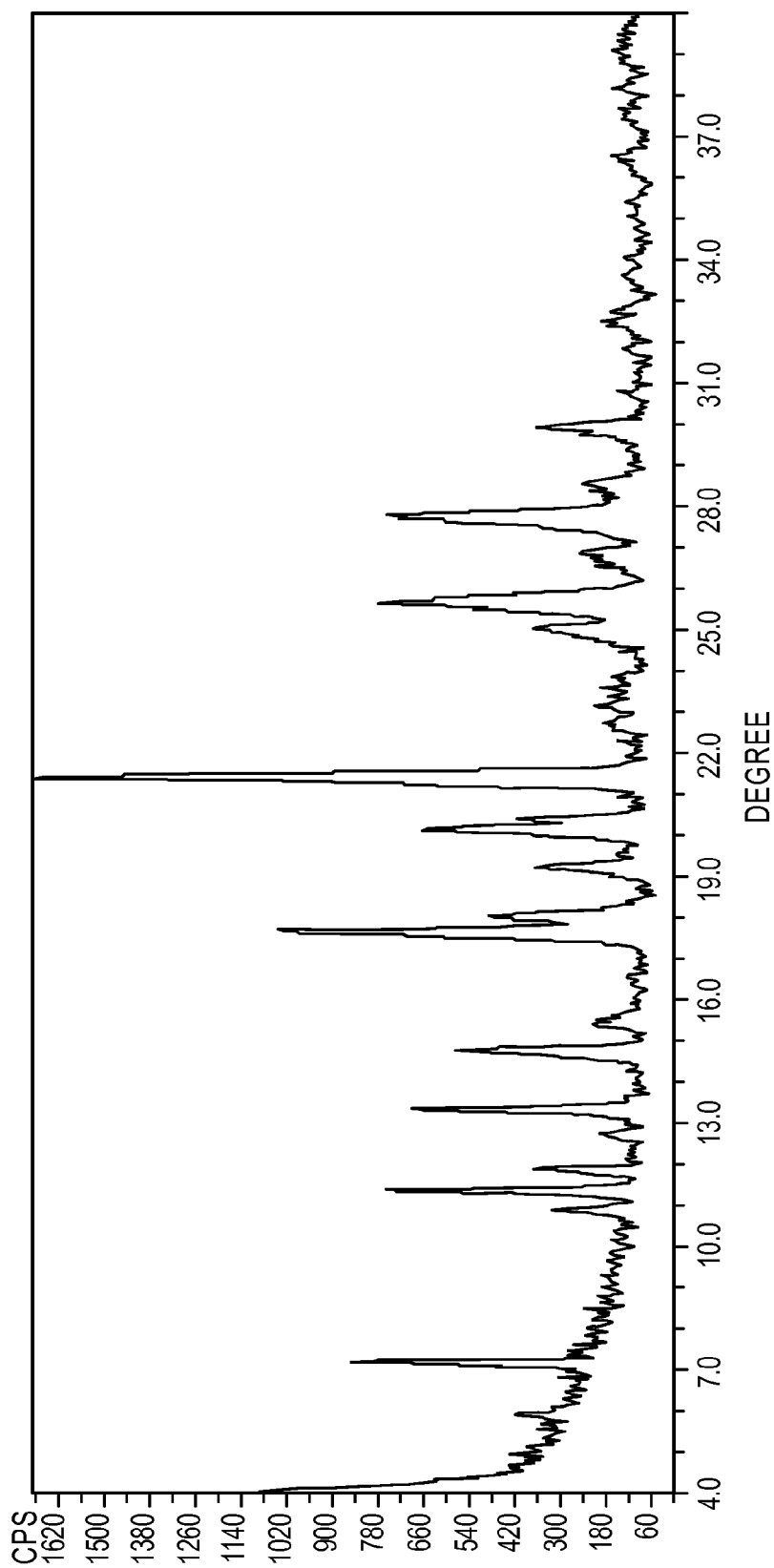
Figure 8:
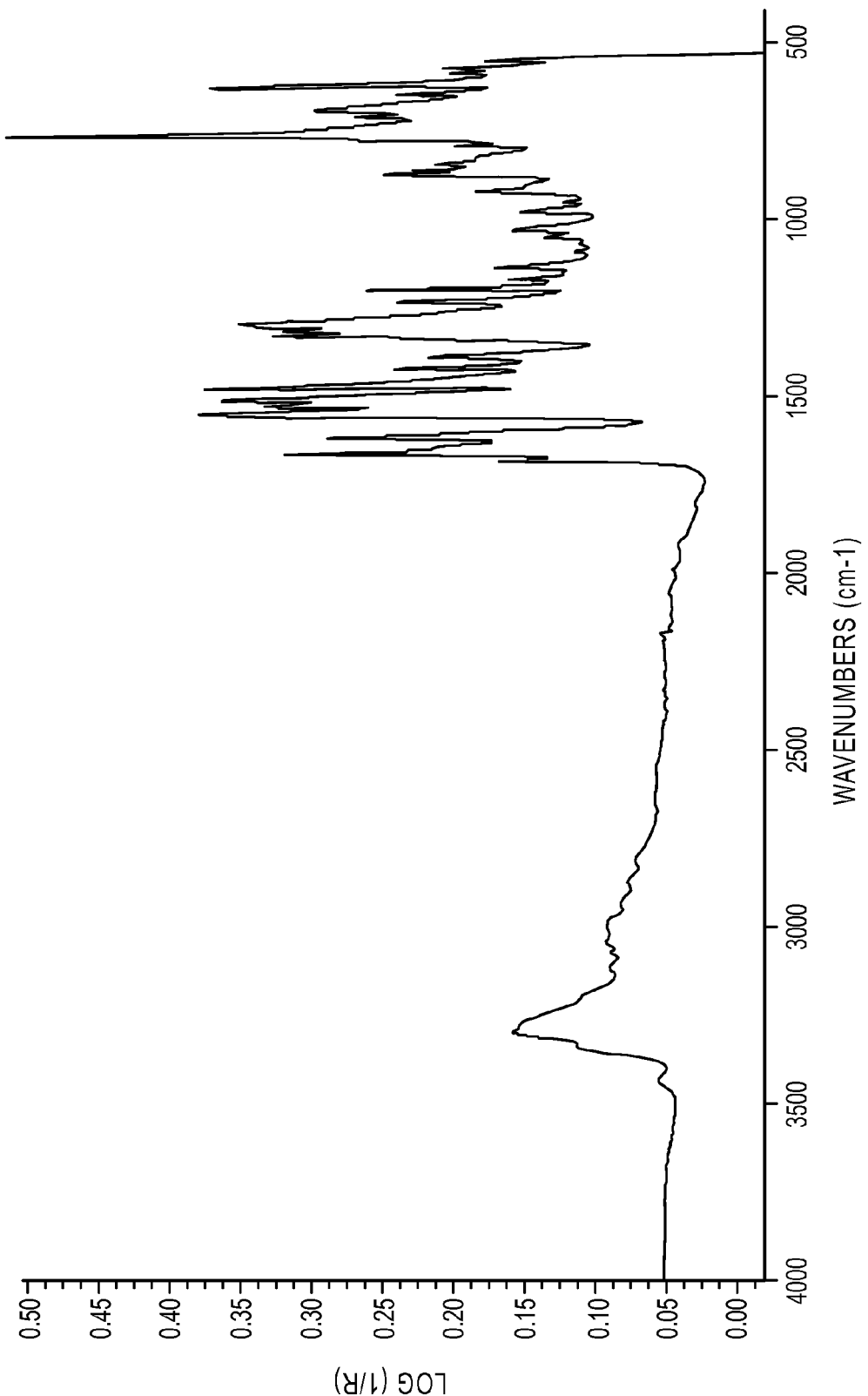
FIG. 8 shows an exemplary IR spectrum of an embodiment of crystalline tacedinaline Form B.

Crystalline tacedinaline Form B was obtained in a crystalline solid form that is characterized by a unique XRPD pattern substantially as shown in FIGS. 7A and 7B, and an IR spectrum substantially as shown in FIG. 8. Crystalline tacedinaline Form B was found to be an anhydrate, as suggested by the representative TGA plot in FIG. 9 that exhibits no weight loss prior to decomposition. Tacedinaline Form B has a melting temperature in the range of about 236-238° C., as found by visual determination, and exhibits a corresponding endothermic event at about 241° C., as shown by the representative DSC trace in FIG. 10. Subsequent to this endothermic event, tacedinaline Form B undergoes a thermally activated dehydrative intramolecular cyclization to form N-(4-(1-H-benzo[d]imidazol-2-yl)acetamide, which exhibits a characteristic endothermic event at about 310° C.

An exemplary listing of representative XRPD peaks of an embodiment of tacedinaline Form B can be found in Table 3. An exemplary listing of representative IR peaks of an embodiment of tacedinaline Form B can be found in Table 4.

Crystalline tacedinaline Form B exhibits improved properties relative to the form of tacedinaline disclosed in the art (Form C). For example, Form B has improved thermal stability relative to tacedinaline Form C. In addition, Form B does not contain methanol, which may be undesirable in various embodiments. Further, the solubility of Form B in water is superior to that of Forms A and D.

TABLE 3

| Form B<br>Degrees 2θ |
| --- |
| 5.96 |
| 7.22 |
| 10.94 |
| 11.41 |
| 11.93 |
| 13.40 |
| 14.80 |
| 17.75 |
| 18.09 |
| 21.53 |
| 27.89 |

TABLE 4

| Form B<br>Reciprocal cm |
| --- |
| 3432.1 |
| 3291.1 |
| 1668.5 |
| 1645.0 |
| 1599.6 |
| 1527.0 |
| 1506.0 |
| 1489.0 |
| 1455.7 |
| 1404.7 |
| 1371.1 |
| 1307.6 |
| 1294.9 |
| 1217.6 |
| 1181.3 |
| 1154.9 |
| 1122.9 |
| 1038.3 |
| 1017.3 |
| 964.4 |
| 905.2 |

TABLE 4-continued

| Form B<br>Reciprocal cm |
| --- |
| 856.2 |
| 845.4 |
| 827.5 |
| 778.1 |
| 738.5 |
| 693.3 |
| 674.6 |
| 631.6 |
| 605.5 |

Crystalline Tacedinaline Form D

Figure 26:
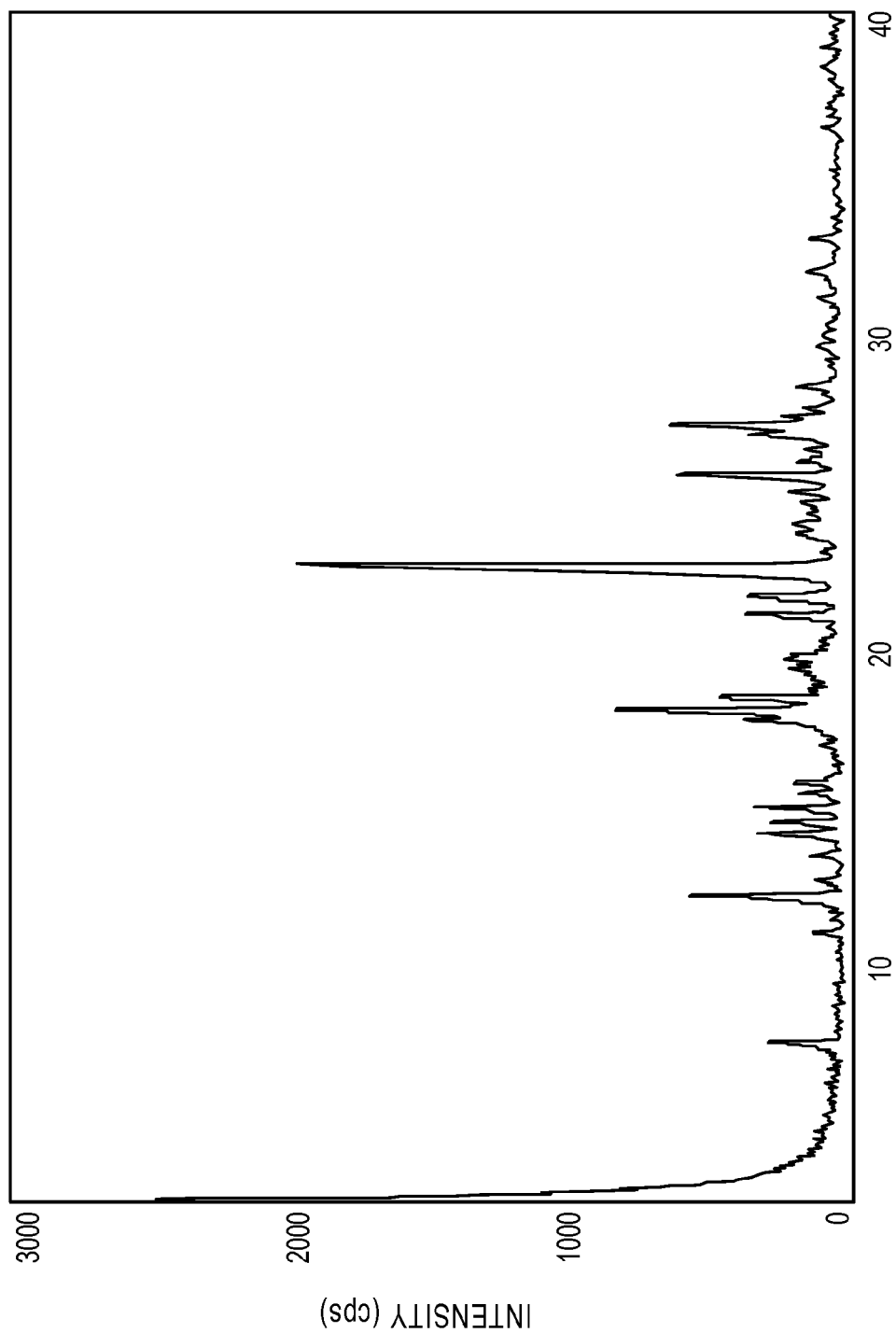
FIG. 26 shows an exemplary XRPD pattern of crystalline tacedinaline Form D.
Figure 27:
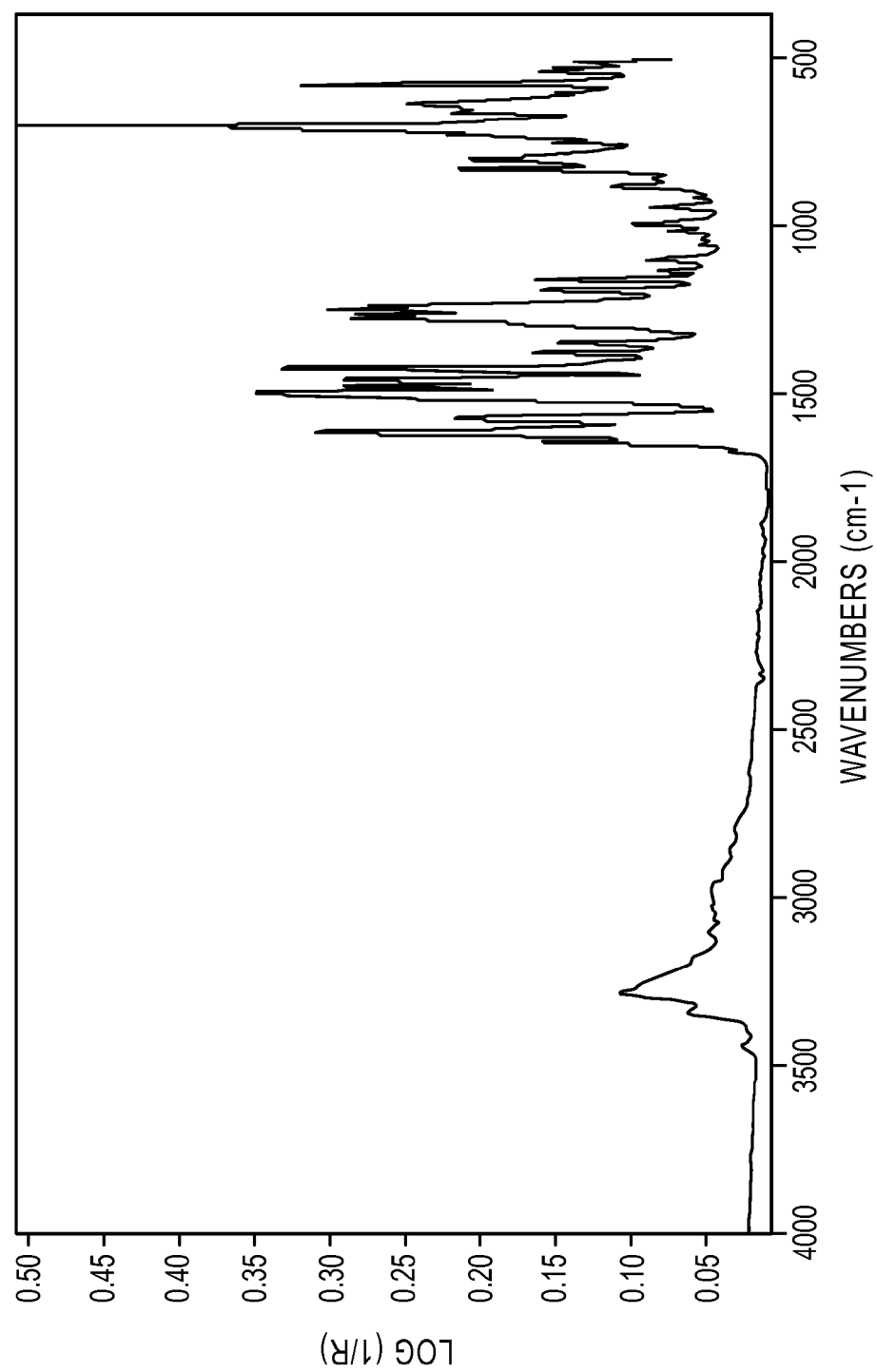
FIG. 27 shows an exemplary IR spectrum of an embodiment of crystalline tacedinaline Form D.
Figure 39A:
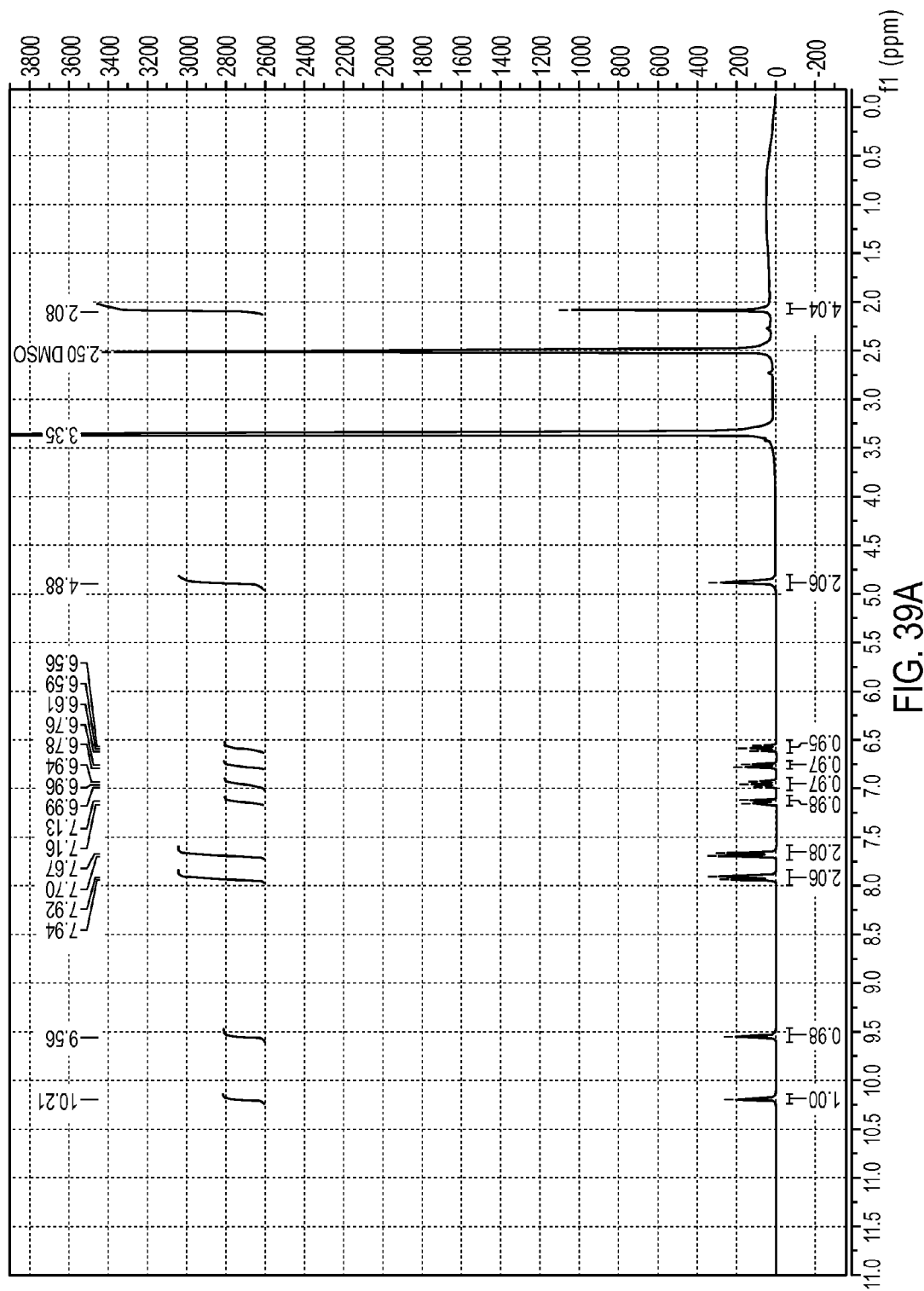
FIGS. 39A-39C show an exemplary ¹H-NMR spectrum of an embodiment of crystalline tacedinaline Form D.
Figure 39B:
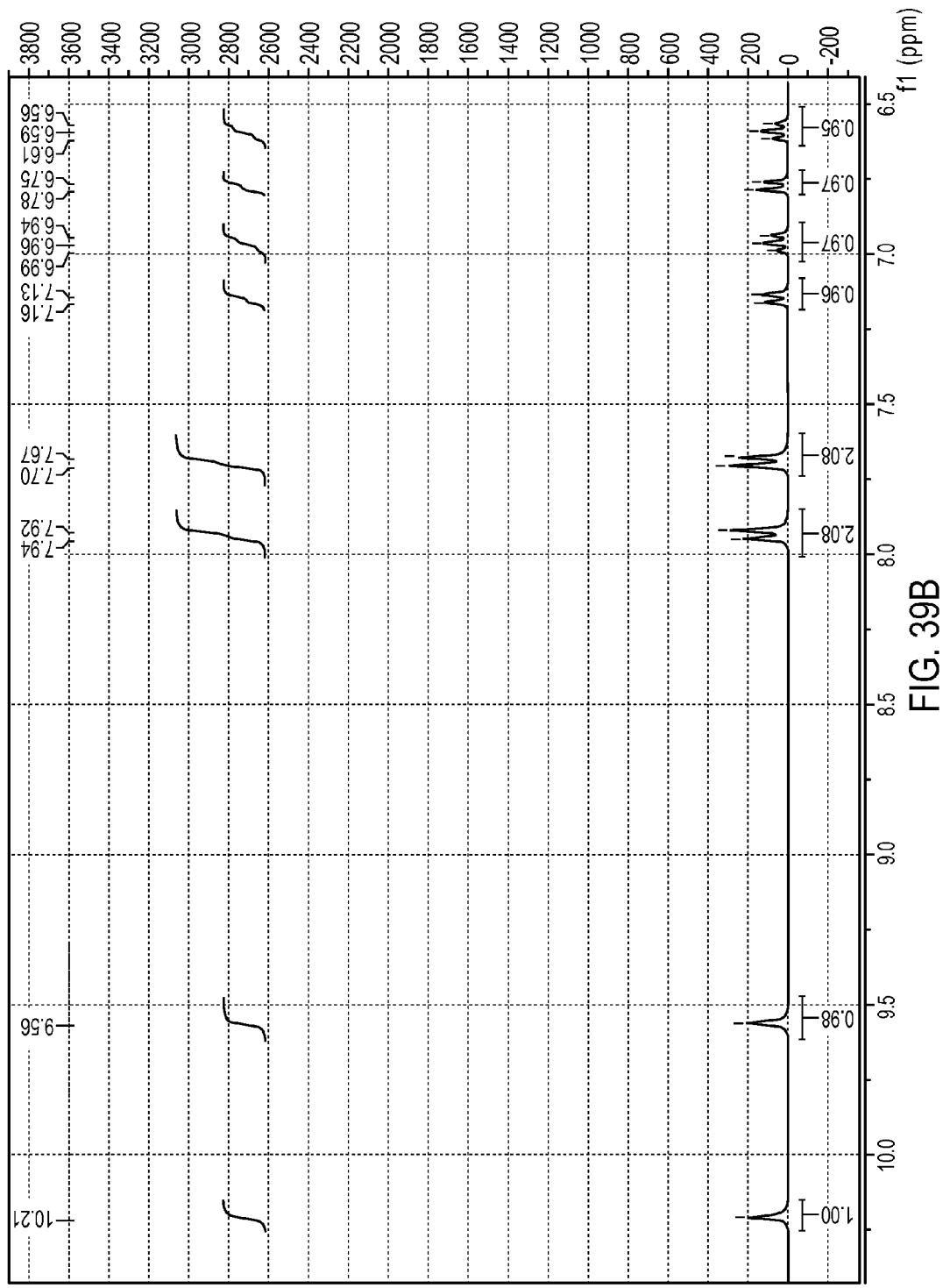
Figure 39C:
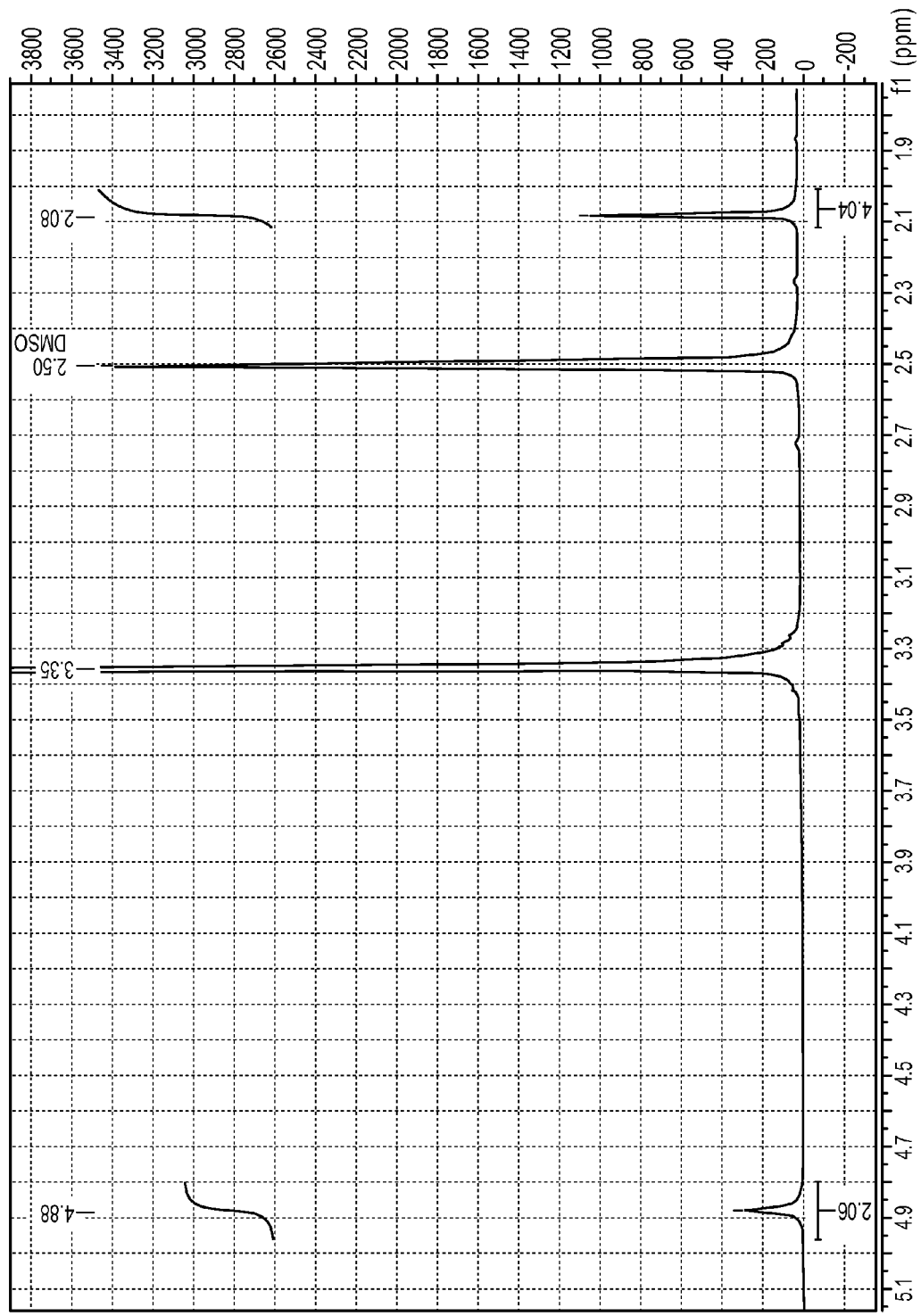
Figure 40A:
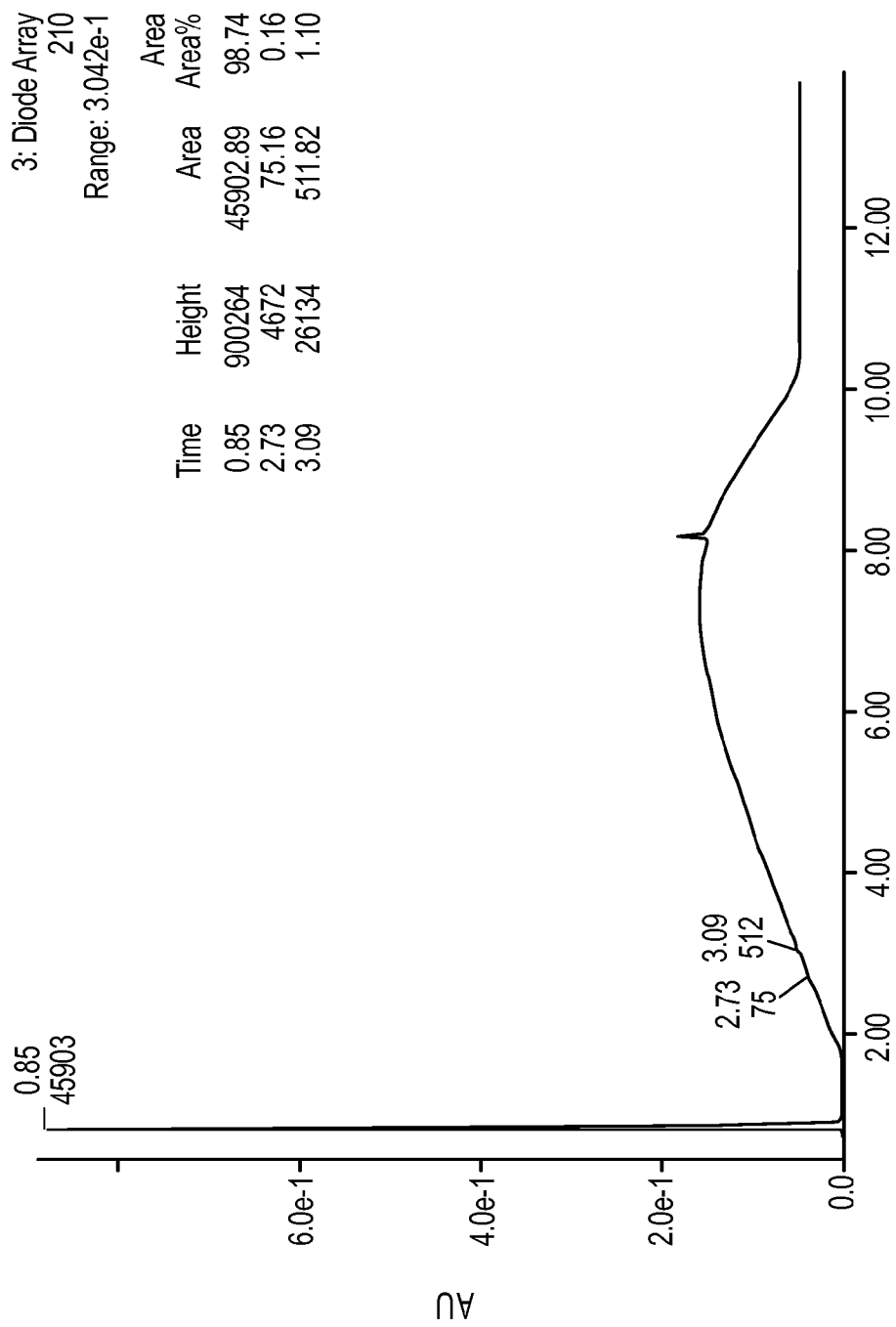
FIGS. 40A-40C show exemplary UPLC/MS data for an embodiment of crystalline tacedinaline Form D.
Figure 40B:
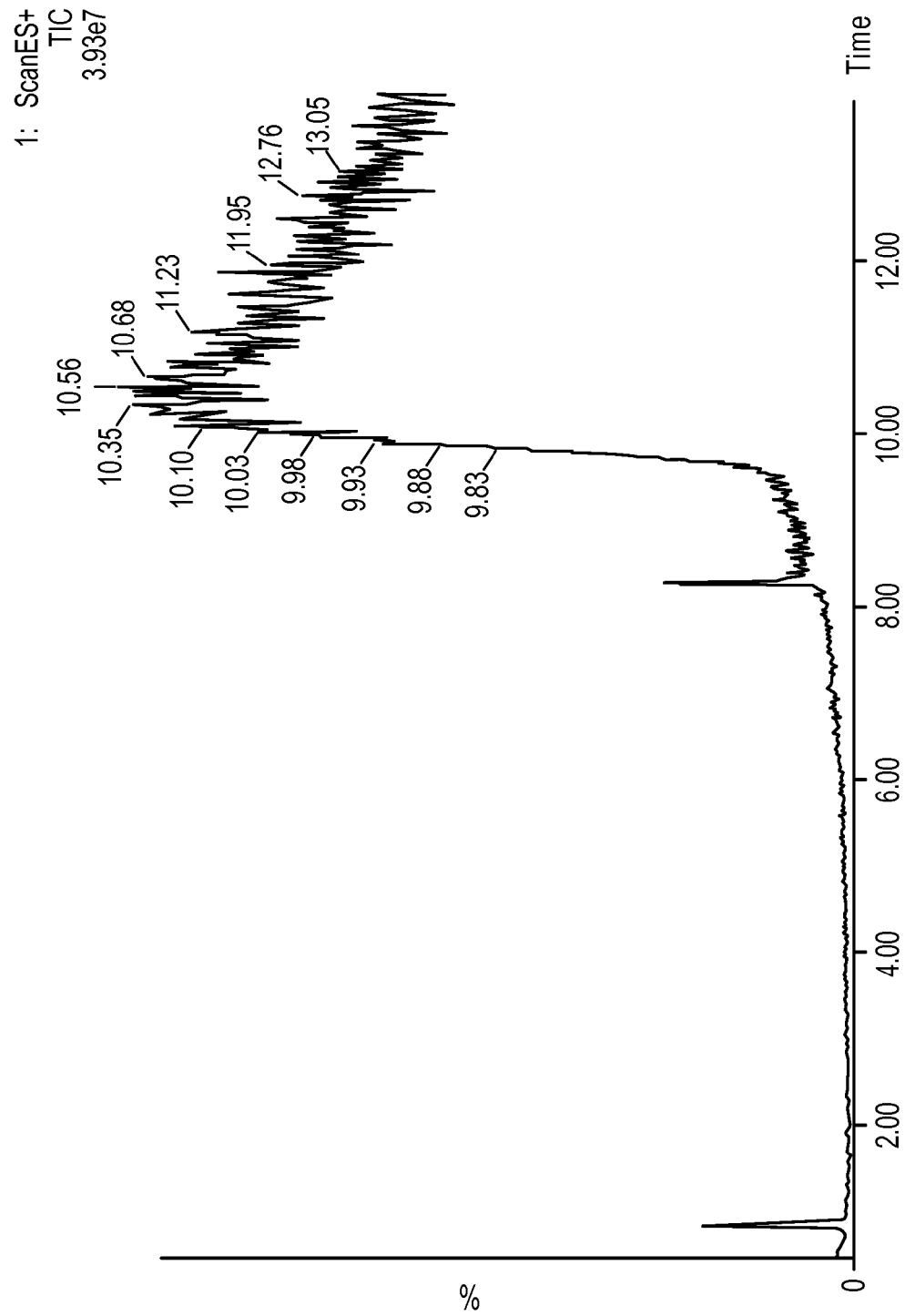
Figure 40C:
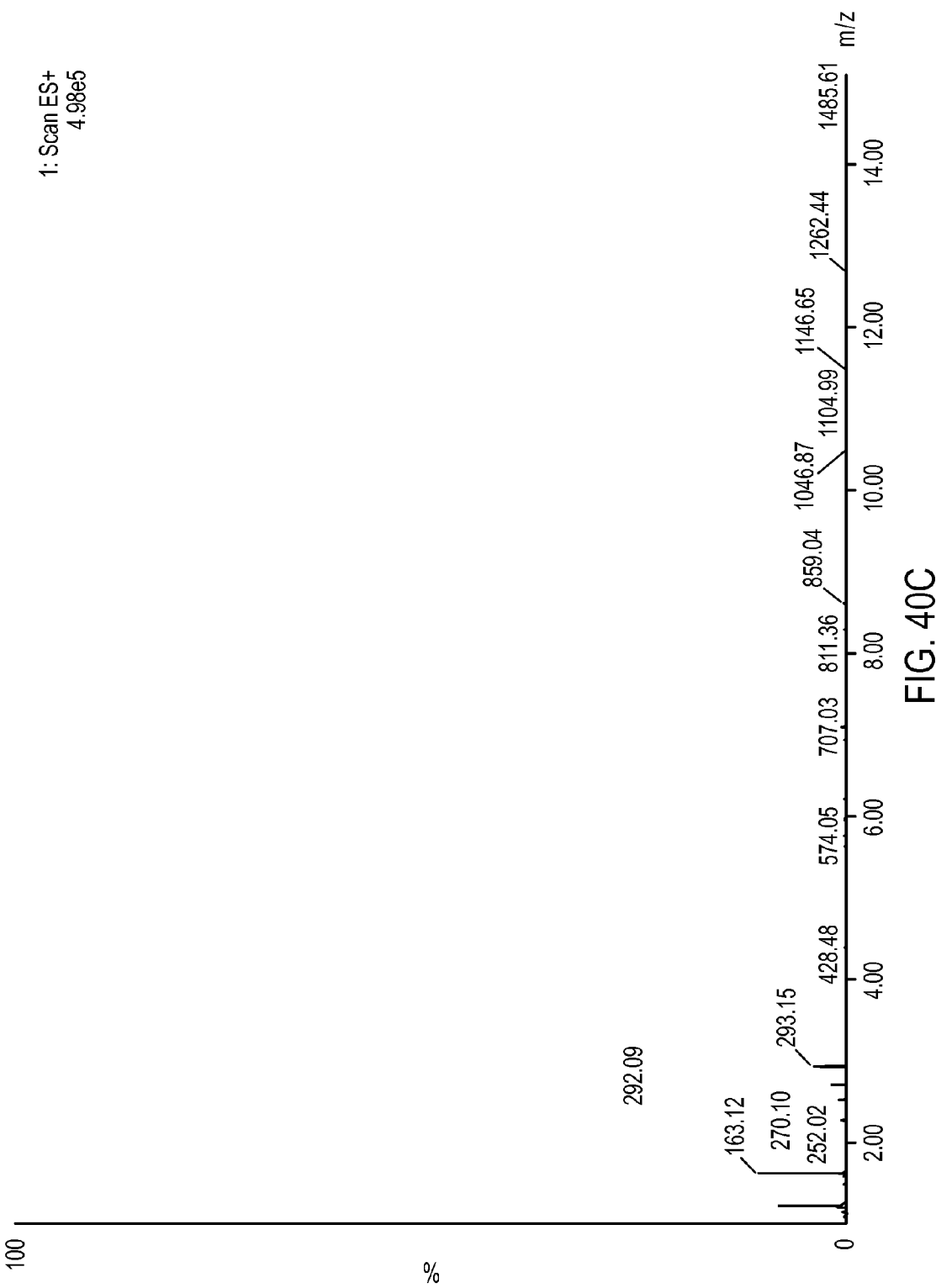

Crystalline tacedinaline Form D was obtained in a crystalline solid form that is characterized by a unique XRPD pattern substantially as shown in FIG. 26, and an IR spectrum substantially as shown in FIG. 27, the $^1$H-NMR as shown in FIGS. 39A-39C, and the UPLC/MS as shown in FIGS. 40A-40C. Tacedinaline Form D was found to be an anhydrate, as suggested by the representative TGA plot in FIG. 28 that exhibits no weight loss prior to decomposition. The anhydrous nature of Form D was confirmed by the single crystal structure. Form D has a melting temperature in the range of about 240-244° C., as found by visual determination, and exhibits a corresponding endothermic event at about 238° C., as shown by the representative DSC trace in FIG. 29. Subsequent to this endothermic event, tacedinaline Form D undergoes a thermally activated dehydrative intramolecular cyclization to form N-(4-(1-H-benzo[d]imidazol-2-yl)acetamide, which exhibits a characteristic endothermic event at about 310° C.

An exemplary listing of representative XRPD peaks of an embodiment of tacedinaline Form D can be found in Table 5. An exemplary listing of representative IR peaks of an embodiment of tacedinaline Form D can be found in Table 6.

Crystalline tacedinaline Form D exhibits improved properties relative to other forms of tacedinaline, including that disclosed in the art (Form C). For example, Form D has improved thermal stability relative to tacedinaline Form C. In addition, Form D does not contain methanol, which may be undesirable in various embodiments. Further, Form D is more thermodynamically stable under certain conditions relative to Form B, as shown in Examples 10A and 12.

TABLE 5

| Form D<br>Degrees 2θ |
| --- |
| 7.31 |
| 11.96 |
| 13.97 |
| 14.35 |
| 14.81 |
| 17.87 |
| 18.31 |
| 21.54 |
| 22.35 |
| 25.34 |

TABLE 6

| Form D Reciprocal cm |
|---|
| 3443.4 |
| 3447.1 |
| 3290.7 |
| 1666.4 |
| 1645.7 |
| 1602.8 |
| 1530.5 |
| 1507.4 |
| 1488.9 |
| 1455.7 |
| 1404.8 |
| 1371.4 |
| 1307.9 |
| 1297.7 |
| 1282.4 |
| 1271.6 |
| 1218.5 |
| 1184.0 |
| 1155.2 |
| 1124.0 |
| 1039.1 |
| 1017.5 |
| 964.8 |
| 904.4 |
| 858.0 |
| 845.7 |
| 830.5 |
| 777.5 |
| 759.0 |
| 738.2 |
| 669.8 |
| 605.3 |

Crystalline Tacedinaline TFA Salt

Figure 33:
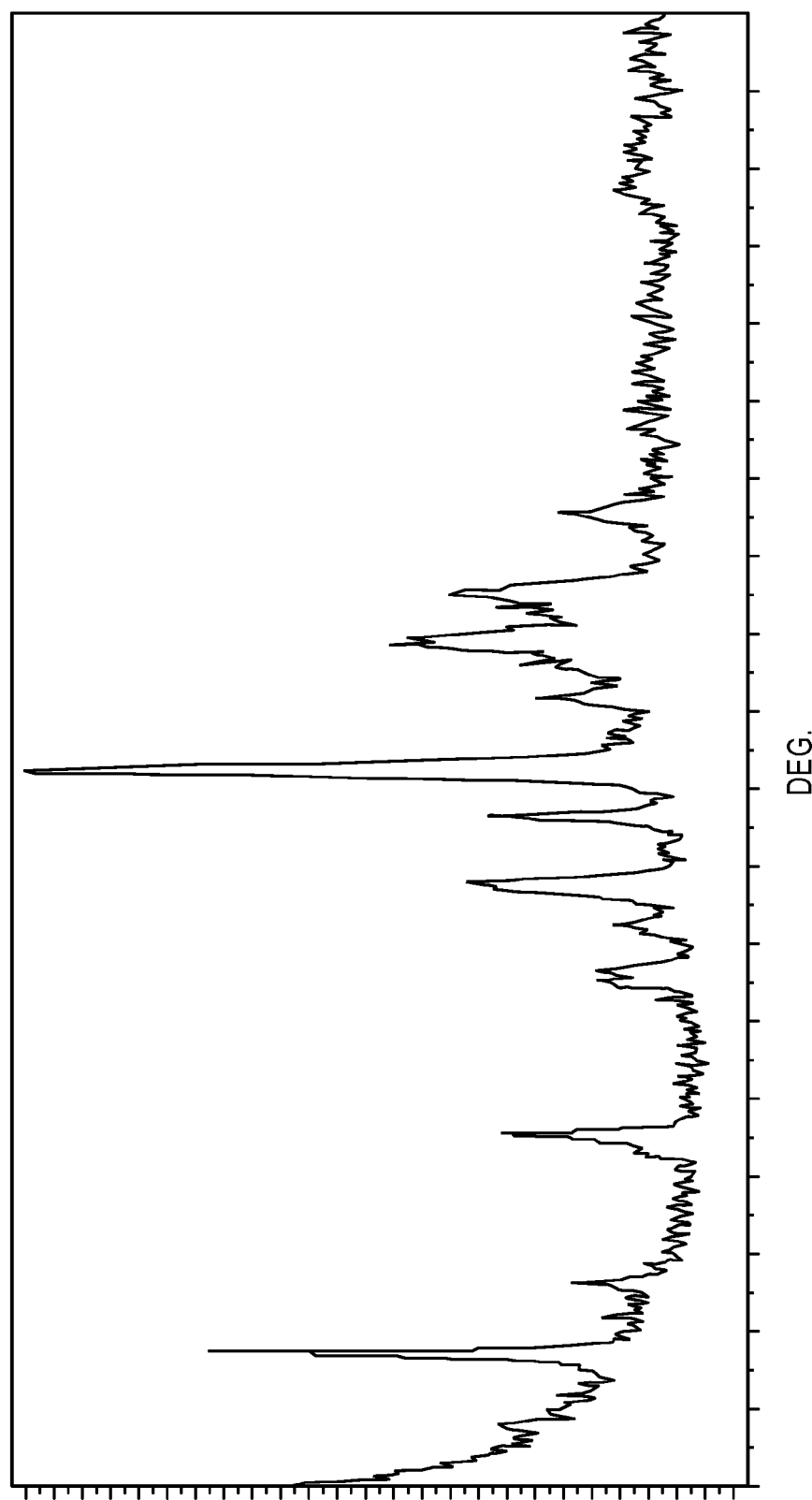
FIG. 33 shows an exemplary XRPD pattern of an embodiment of crystalline tacedinaline TFA salt.
Figure 34:
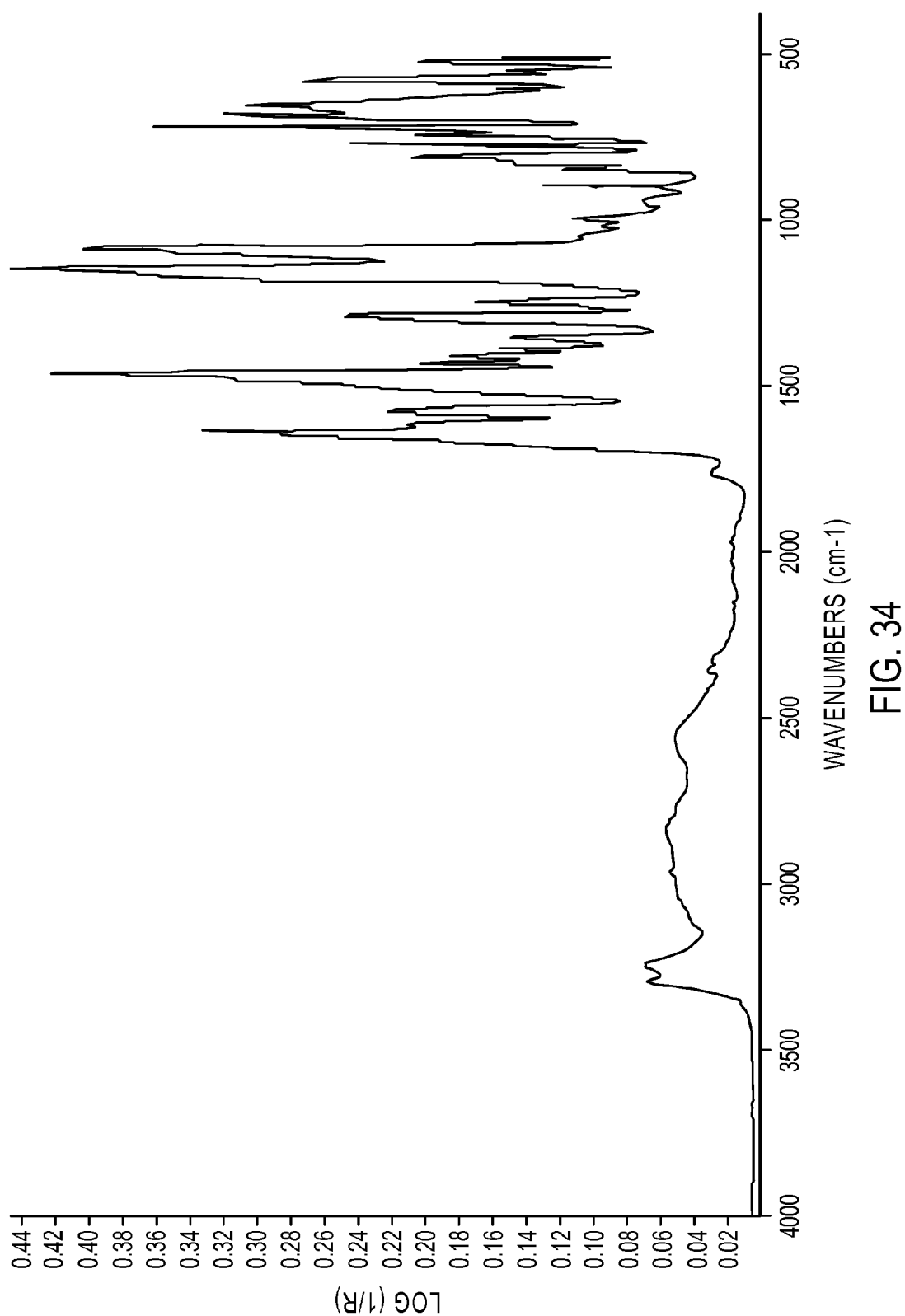
FIG. 34 shows an exemplary IR spectrum of an embodiment of crystalline tacedinaline TFA salt.
Figure 35:
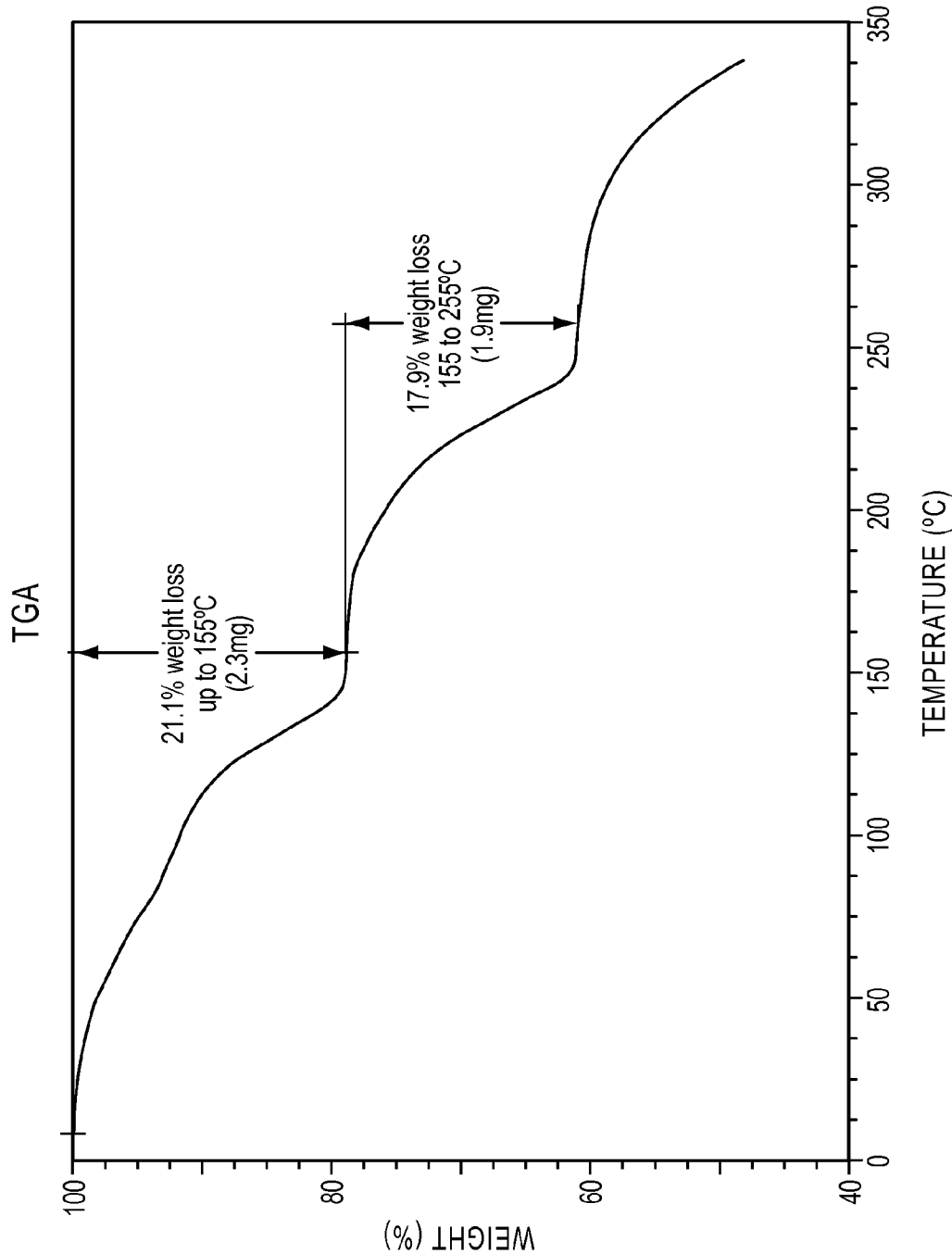
FIG. 35 shows an exemplary TGA profile of an embodiment of crystalline tacedinaline TFA salt.
Figure 36:
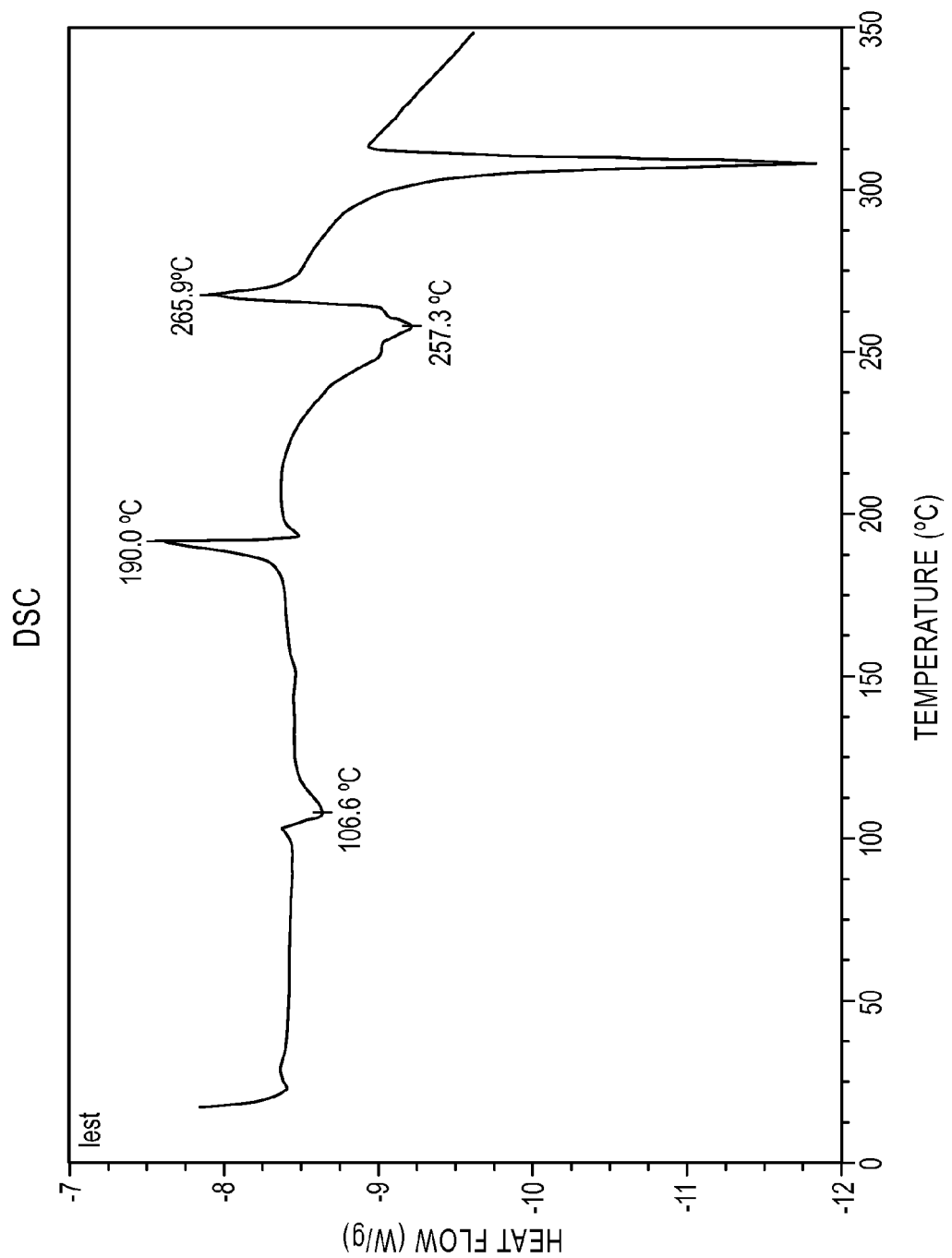
FIG. 36 shows an exemplary DSC thermogram of an embodiment of crystalline tacedinaline TFA salt.
Figure 37:
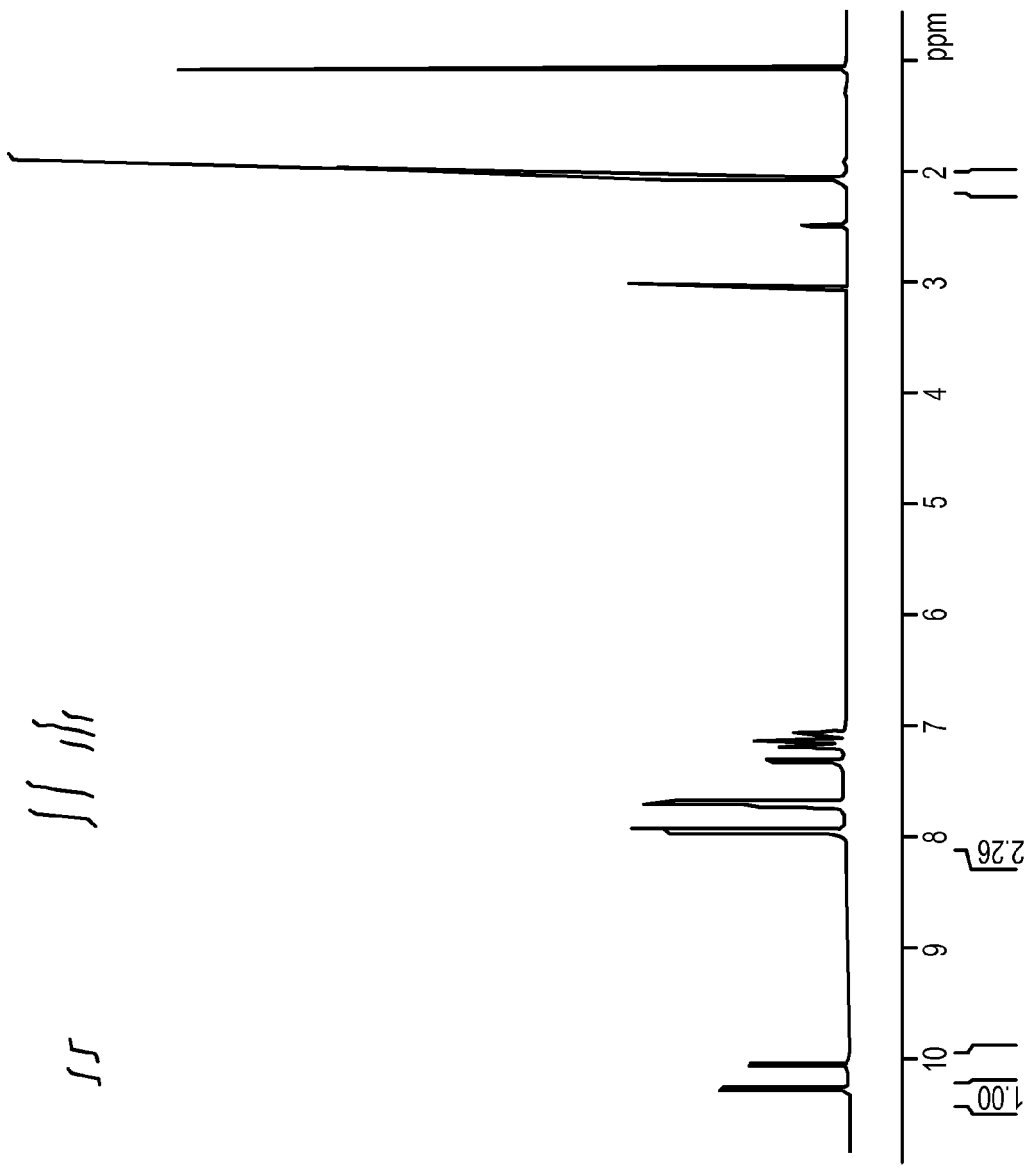
FIG. 37 shows an exemplary ¹H-NMR spectrum of an embodiment of crystalline tacedinaline TFA salt.
Figure 38A:
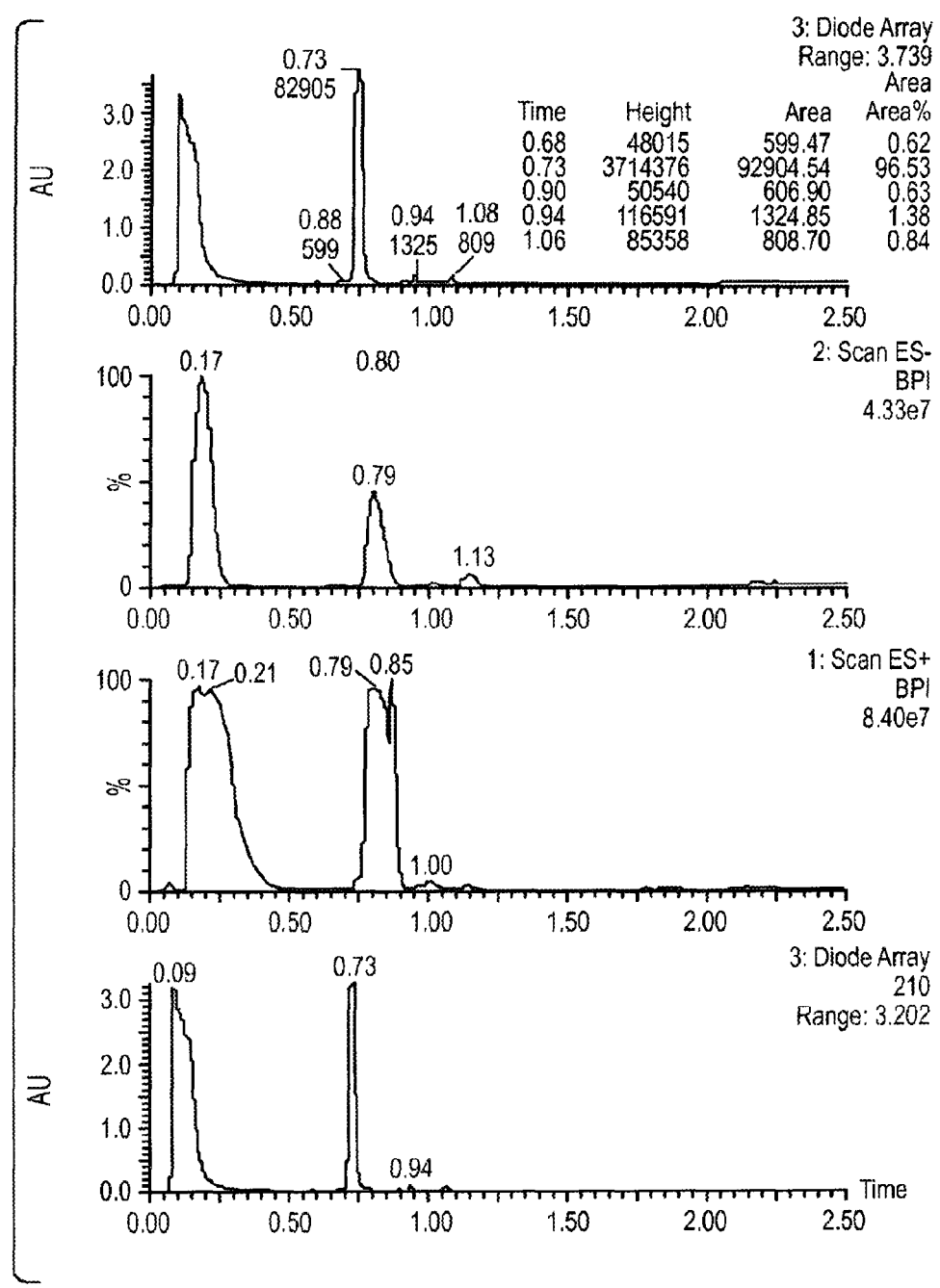
FIGS. 38A-38B show exemplary LC/MS data for an embodiment of crystalline tacedinaline TFA salt.
Figure 38B:
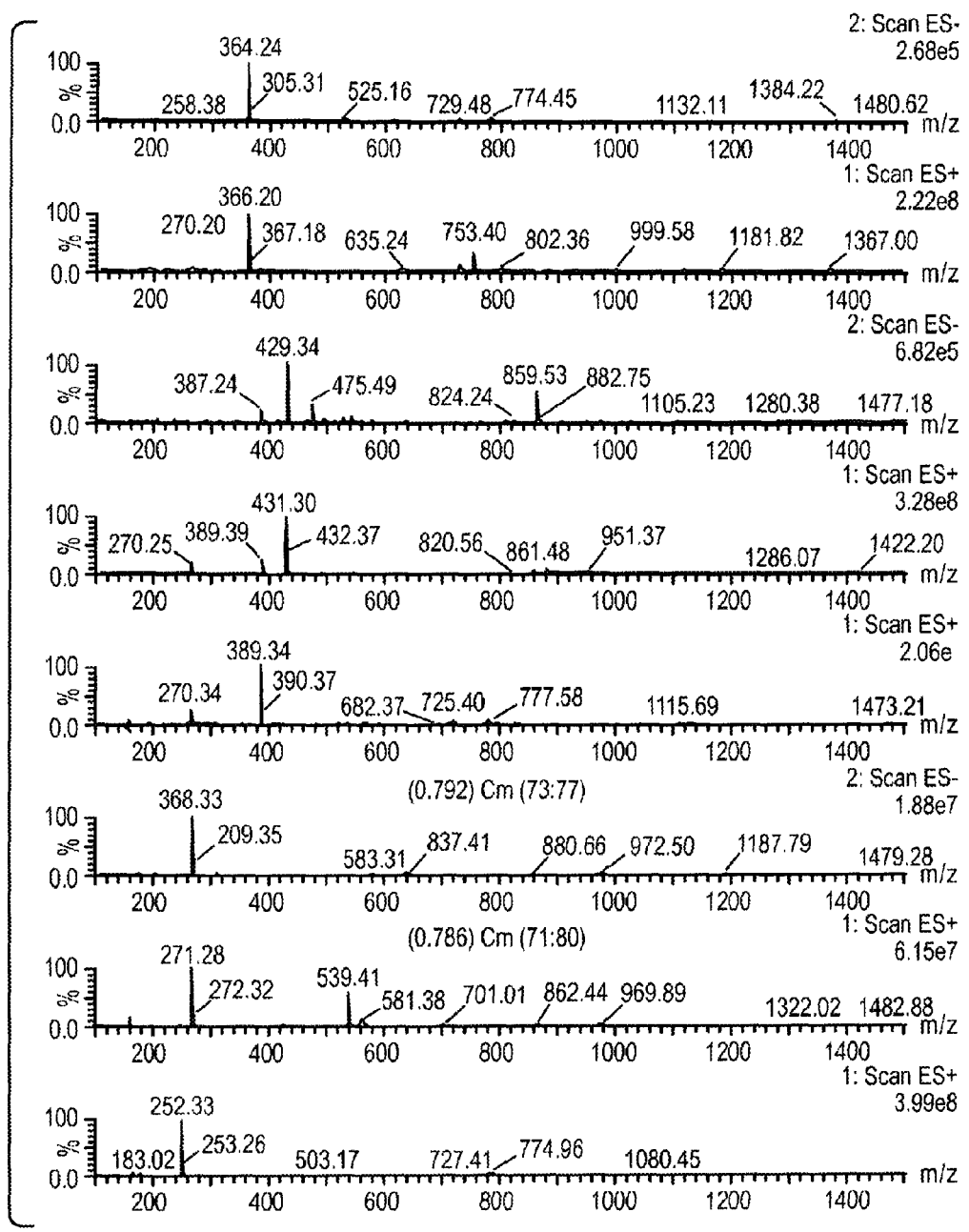

A novel tacedinaline TFA (trifluroacetate) salt was obtained in a crystalline solid form, characterized by a unique XRPD pattern as shown in FIG. 33. Representative TGA plot can be found in FIG. 35, and representative DSC can be found in FIG. 36. Subsequent to the endothermic event at about 257° C., as can be seen in the DSC trace, it appears that the novel crystalline tacedinaline TFA salt undergoes a thermally activated dehydrative intramolecular cyclization to form N-(4-(1-H-benzo[d]imidazol-2-yl)acetamide, which exhibits a characteristic endothermic event at about 310° C.

An exemplary listing of representative XRPD peaks of an embodiment of the crystalline tacedinaline TFA salt can be found in Table 7. An exemplary listing of representative IR peaks of an embodiment of the crystalline tacedinaline TFA salt can be found in Table 8.

In at least one embodiment, the use of trifluroacetic acid provides optimal reaction conditions and yields for the deprotection of the BOC intermediate (see Example 15, below). The isolation of the resulting trifluoroacetate salt allowed for decreased residual TFA, reduced reaction volumes during the neutralization reaction, increased reaction yields, shorter reaction times, and/or higher purity of the resulting free base.

An exemplary listing of representative XRPD peaks of an embodiment of crystalline tacedinaline TFA salt can be found in Table 7. An exemplary listing of representative IR peaks of an embodiment of crystalline tacedinaline TFA salt can be found in Table 8.

TABLE 7

| TFA Salt Degrees 2θ |
|---|
| 5.47 |
| 11.12 |
| 17.54 |
| 19.30 |
| 20.47 |

TABLE 8

| TFA salt Reciprocal cm |
|---|
| 3304.0 |
| 3255.8 |
| 1777.0 |
| 1668.0 |
| 1641.0 |
| 1600.6 |
| 1498.8 |
| 1452.8 |
| 1431.0 |
| 1407.2 |
| 1372.5 |
| 1316.7 |
| 1268.3 |
| 1182.2 |
| 1122.1 |
| 1037.5 |
| 1020.0 |
| 866.8 |
| 839.1 |
| 797.1 |
| 769.0 |
| 750.3 |
| 717.1 |
| 687.4 |
| 632.0 |
| 606.9 |
| 549.2 |

Amorphous Tacedinaline

Figure 30:
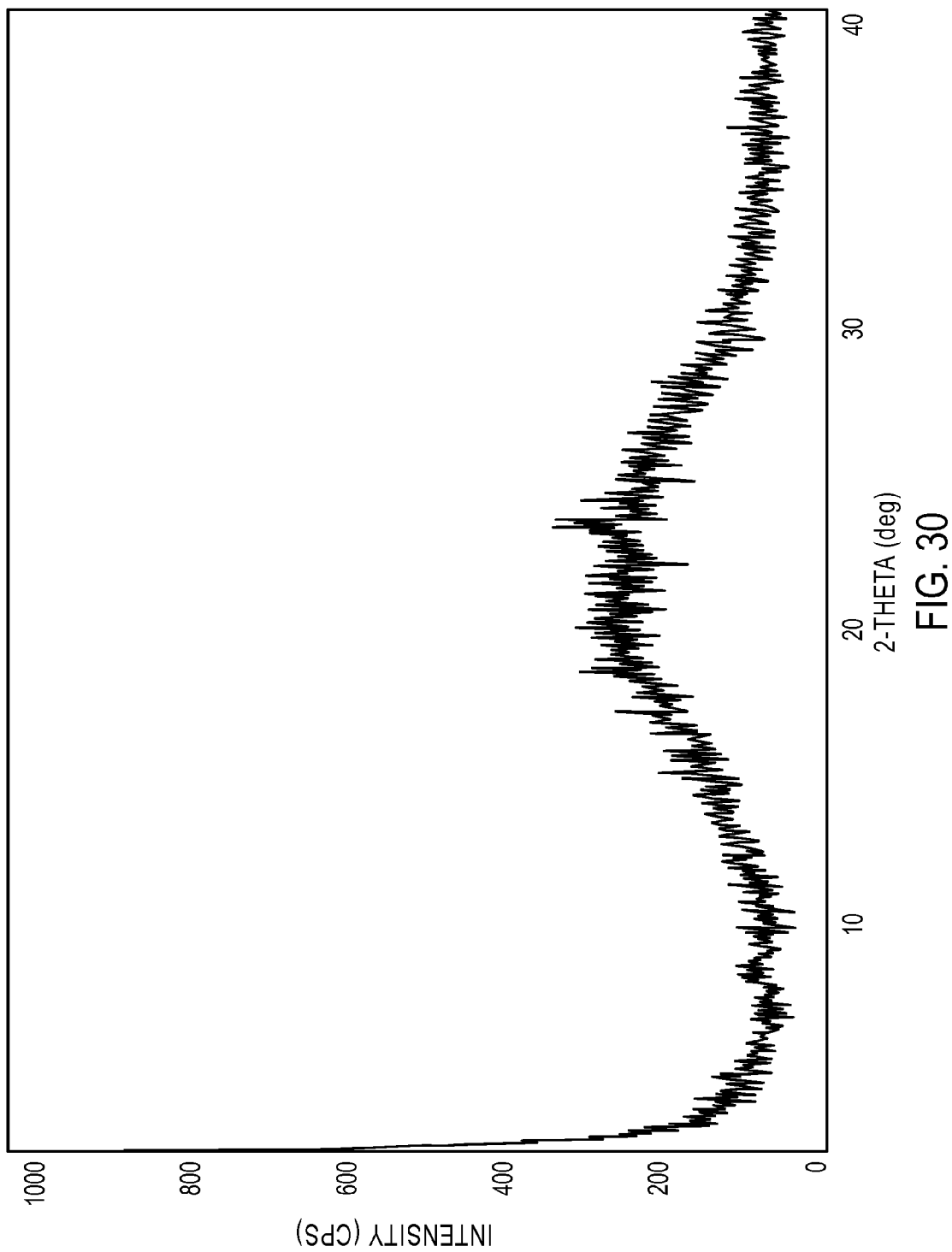
FIG. 30 shows an exemplary XRPD pattern of an embodiment of a mixture of amorphous tacedinaline and N-(4-(1-H-benzo[d]imidazol-2-yl)acetamide.
Figure 42:
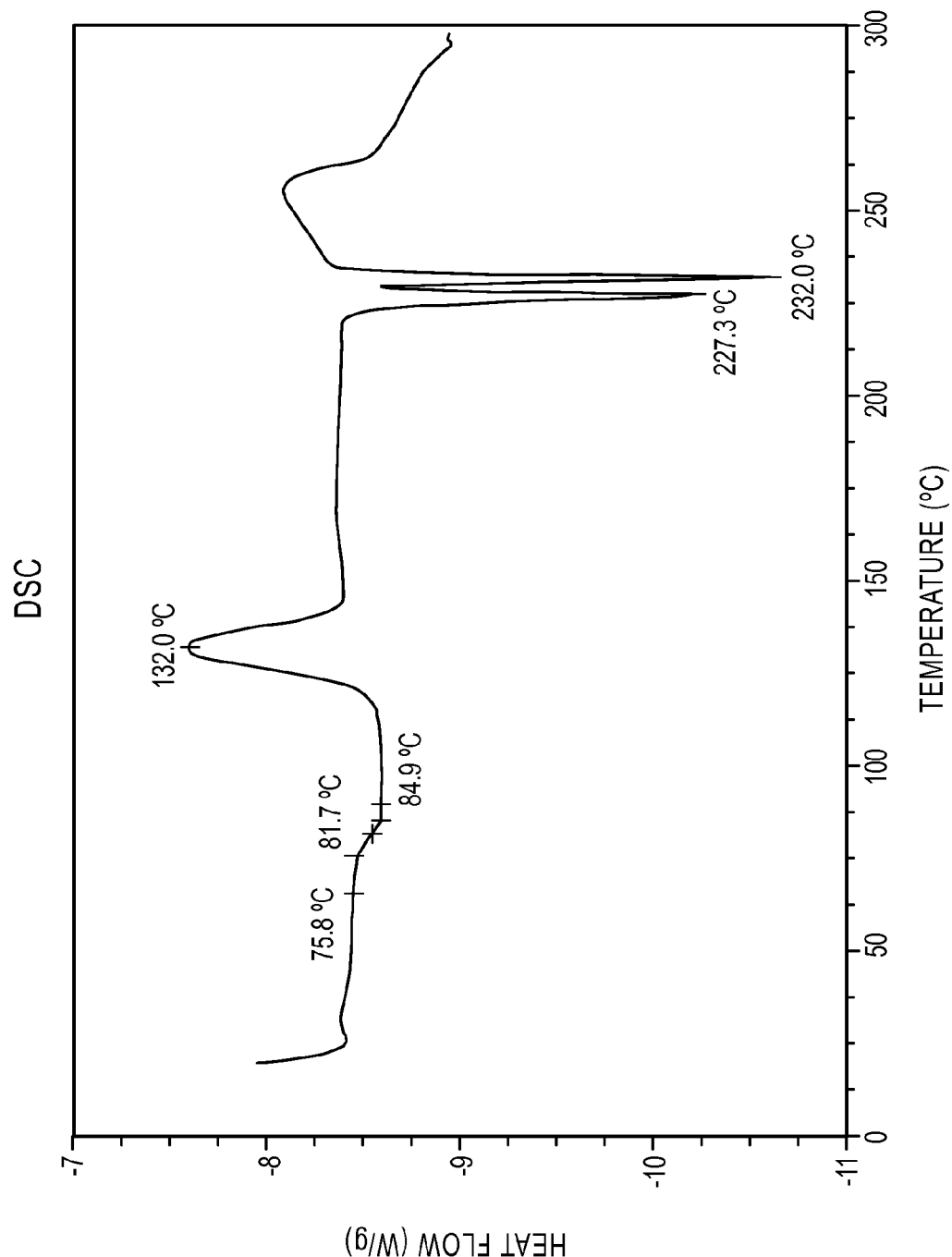
FIG. 42 shows an exemplary DSC thermogram of an embodiment of a mixture of amorphous tacedinaline and N-(4-(1-H-benzo[d]imidazol-2-yl)acetamide, and FIG. 32B shows LC/MS data for N-(4-(1-H-benzo[d]imidazol-2-yl)acetamide.

Amorphous tacedinaline was obtained in a solid form as a mixture with N-(4-(1-H-benzo[d]imidazol-2-yl)acetamide, and is characterized by an XRPD pattern having a classic "amorphous halo", as shown in FIG. 30. The amorphous tacedinaline mixture has a glass transition temperature at about 82° C., exhibits an endothermic event at about 132° C., and two endothermic events at about 227° C. and 232° C., as shown by the representative DSC trace in FIG. 42.

Figure 25:
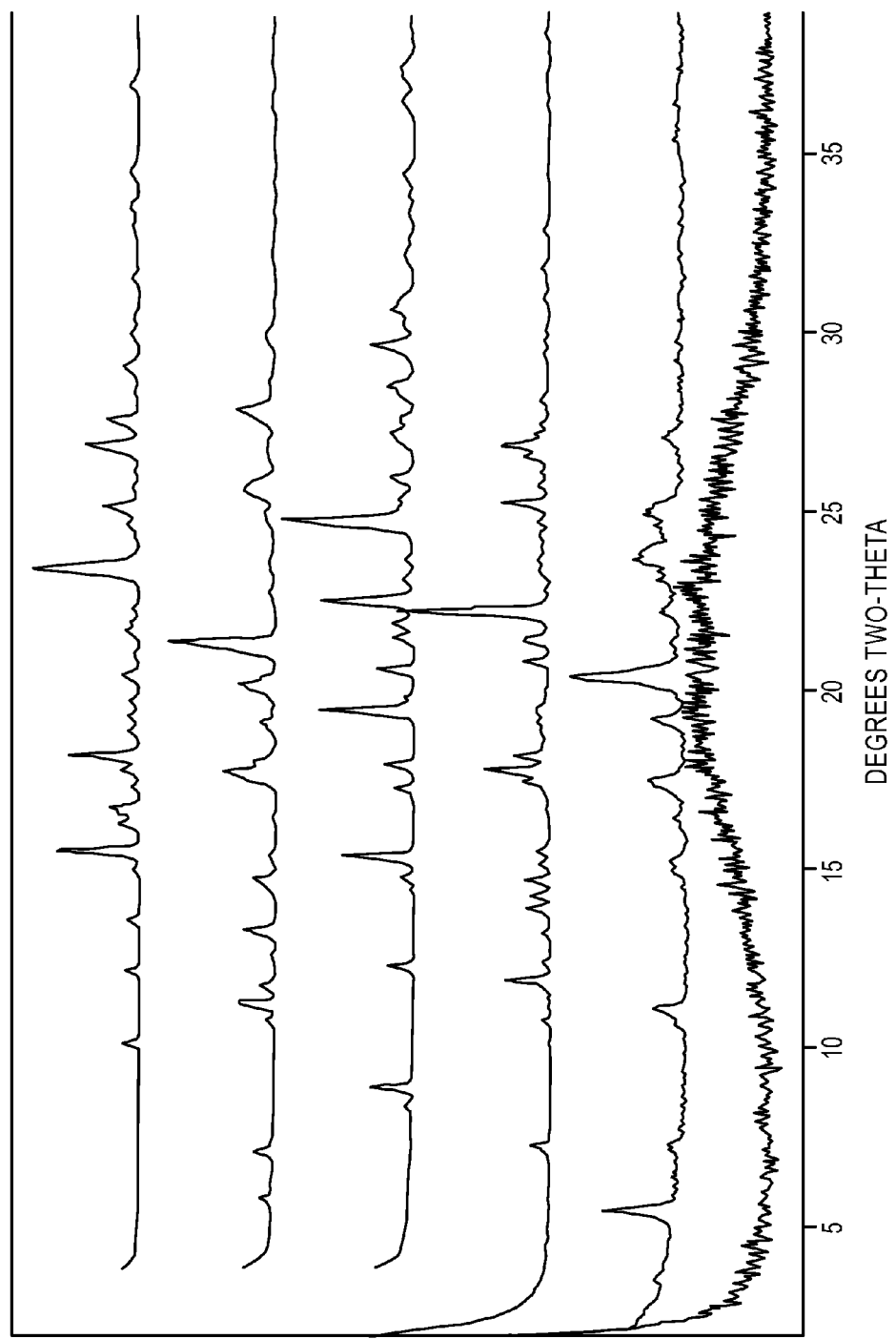
FIG. 25 shows a comparison of exemplary XRPD patterns for crystalline tacedinaline Forms A, B, C, and D, crystalline tacedinaline TFA salt, and amorphous tacedinaline (top to bottom).

As can be seen from the differences in XRPD patterns in FIG. 25, crystalline tacedinaline Forms A, B, C, and D, and the novel crystalline tacedinaline TFA salt, each exhibit unique crystallographic properties, and each represents a distinct crystal form of the compound. As can also be seen from FIG. 25, the amorphous mixture exhibits a broad, featureless diffraction pattern, as is typical of a non-crystalline form.

The invention in various exemplary embodiments relates to pure or substantially pure crystalline tacedinaline Form A, crystalline tacedinaline Form B, crystalline tacedinaline Form D, the novel crystalline tacedinaline TFA salt form, or amorphous tacedinaline. By way of example, in one embodiment, the invention may relate to a batch or lot of tacedinaline which is 50% or more, such as 60% or more, 75% or more, 90% or more, 95% or more, 98% or more, or 99% or more, crystalline tacedinaline Form A, crystalline tacedinaline Form B, crystalline tacedinaline Form D, the novel crystalline tacedinaline TFA salt form, or amorphous tacedinaline. In further exemplary embodiments, the invention relates to pharmaceutical compositions and/or formulations comprising pure or substantially pure crystalline tacedinaline Form A, crystalline tacedinaline Form B, crystalline tacedinaline Form D, the novel crystalline tacedinaline TFA salt form, or amorphous tacedinaline.

In further embodiments, the invention relates to crystalline tacedinaline Form A, crystalline tacedinaline Form B, crystalline tacedinaline Form D, the novel crystalline tacedinaline TFA salt form, and/or amorphous tacedinaline in a mixture, such as a mixture of crystalline tacedinaline Forms A, B, and/or D, the novel crystalline tacedinaline TFA salt form, and/or amorphous tacedinaline, or in a mixture comprising additional known or as yet unknown solid forms of tacedinaline. By way of example only, the mixture may comprise one or more of crystalline tacedinaline Forms A, B, and D, the novel crystalline tacedinaline TFA salt form, and/or amorphous tacedinaline in combination with Form C.

Pharmaceutical Compositions and Methods of Treatment

The novel solid forms of tacedinaline of the invention possess substantially the same pharmacological activity as the known form of tacedinaline, and are therefore useful in methods of treating, alleviating, and/or preventing various conditions including, for example, neoplastic diseases, memory loss, and cognitive function disorders/impairments. Neoplastic diseases include, for example, cancers such as prostate, breast, colon, and brain, including without limitation glioblastoma.

Exemplary cognitive function disorders that may be treated, alleviated, and/or prevented according to various embodiments of the invention include, but are not limited to, those disclosed in WO 2011/053876 A1, incorporated herein by reference in its entirety. By way of example only, cognitive function disorders/impairments that may be treated, alleviated, and/or prevented include those associated with Alzheimer's disease, Huntington's disease, seizure-induced memory loss, schizophrenia, Rubinstein-Taybi syndrome, Rett syndrome, Fragile X, Lewy body dementia, vascular dementia, attention deficit hyperactivity disorder (ADHD), dyslexia, bipolar disorder, anxiety disorders, conditioned fear response, panic disorders, obsessive compulsive disorders, post-traumatic stress disorder, phobias, social anxiety disorders, substance dependence recovery, and social, cognitive, and learning disorders associated with autism, traumatic head injury, or attention deficit disorder (ADD).

By use of the term "treating" or "alleviating" herein, it is meant decreasing the symptoms, markers, and/or any negative effects of a condition in any appreciable degree in a patient who currently has the condition. By use of the term "preventing" it is meant preventing entirely or preventing to some extent, such as, for example, by inhibiting all together or delaying the onset or lessening the degree to which a patient develops a condition.

In further embodiments of the invention are provided methods of improving cognitive function in a normal subject. As used herein, a "normal subject" is a subject that has not been diagnosed with a disorder associated with impaired cognitive function. Improving cognitive function includes promoting cognitive function in a subject so that the subject more closely resembles or exceeds the function of an age-matched normal, unimpaired subject.

Further exemplary embodiments of the invention relate to methods of promoting fear extinction in a subject.

The methods of the invention described herein may be accomplished by administering to a subject a therapeutically effective amount of tacedinaline comprising crystalline tacedinaline Form A, crystalline tacedinaline Form B, crystalline tacedinaline Form D, the novel crystalline tacedinaline TFA salt form, and/or amorphous tacedinaline. As used herein, a "therapeutically effective amount" refers to an amount of a therapeutic agent sufficient to treat, alleviate, and/or prevent a condition by administration of a composition of the invention. That amount is any amount sufficient to exhibit a detectable therapeutic and/or preventative and/or ameliorative effect, and can be determined by routine experimentation by those of skill in the art. The effect may include treatment, alleviation, and/or prevention of any of the disorders or conditions listed herein, for example, as well as symptoms associated therewith. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; and the rate of excretion of tacedinaline; the duration of the treatment; any drugs used in combination with or coincidental to the treatment; and other such factors well known in the medical arts.

The invention in various exemplary embodiments relates to pharmaceutical compositions and formulations comprising crystalline tacedinaline Form A, tacedinaline Form B, tacedinaline Form D, the novel crystalline tacedinaline TFA salt form, and/or amorphous tacedinaline, in any amount. Thus, for example, the invention in various embodiments relates to pharmaceutical compositions and formulations comprising even one or a few crystals of tacedinaline Form A, tacedinaline Form B, and/or tacedinaline Form D, the novel crystalline tacedinaline TFA salt form, and/or one or a few particles of amorphous tacedinaline. As a further example, the pharmaceutical compositions and formulations may comprise crystalline tacedinaline Form A, Form B, and/or Form D, the novel crystalline tacedinaline TFA salt form, and/or amorphous tacedinaline, in an amount sufficient to be detected by analytical methods known in the art, such as, for example, IR, XRPD, Raman spectroscopy, and the like.

In further exemplary embodiments, the invention relates to pharmaceutical compositions and formulations comprising a therapeutically effective amount of tacedinaline comprising any amount of crystalline tacedinaline Form A, tacedinaline Form B, and/or tacedinaline Form D, the novel crystalline tacedinaline TFA salt form, and/or amorphous tacedinaline. As such, the amount of any one of, or a combination of, crystalline tacedinaline Form A, tacedinaline Form B, and/or tacedinaline Form D, the novel crystalline tacedinaline TFA salt form, and/or amorphous tacedinaline, may not themselves be present in a therapeutically effective amount in various exemplary pharmaceutical compositions and formulations. However, as contemplated herein, as long as some amount of at least one of crystalline tacedinaline Forms A, B, and/or D, the novel crystalline tacedinaline TFA salt form, and/or amorphous tacedinaline, is present, the pharmaceutical composition and/or formulation is within the scope of the invention.

A pharmaceutical composition of the invention may be in any pharmaceutical form which contains any amount of crystalline tacedinaline Forms A, B, and/or D, the novel crystalline tacedinaline TFA salt form, and/or amorphous tacedinaline, as described herein. For example, the pharmaceutical compositions of the invention may be formulated in unit dosage form for ease of administration and uniformity of dosage. A "unit dosage form" refers to a physically discrete unit of therapeutic agent appropriate for the patient to be treated. In one exemplary embodiment, the pharmaceutical composition of the invention is a solid unit dosage form that maintains the solid form of at least some amount of crystalline tacedinaline Forms A, B, and/or D, the novel crystalline tacedinaline TFA salt form, and/or amorphous tacedinaline. Unit dosage forms include, but are not limited to, those disclosed in WO 2011/053876 A1.

Solid unit dosage forms useful for oral administration according to the invention include, for example, capsules, tablets, pills, powders, and granules. The active ingredient may optionally be administered in a formulation that provides quick release, sustained release or delayed release after administration to the patient. In such solid unit dosage forms, the active compound may be mixed with at least one inert, pharmaceutically acceptable carrier, such as sodium citrate or dibasic calcium phosphate, or any other pharmaceutically acceptable carrier known in the art. The choice of the pharmaceutically acceptable carrier depends upon the pharmaceutical form and the desired method of administration to be used. For a pharmaceutical composition of the invention, that is one having crystalline tacedinaline Forms A, B, and/or D, the novel crystalline tacedinaline TFA salt form, and/or amorphous tacedinaline, a carrier should be chosen that maintains the solid form of at least some amount of at least one of crystalline tacedinaline Forms A, B, and/or D, the novel crystalline tacedinaline TFA salt form, and/or the amorphous form. In other words, the carrier should not substantially alter the solid form of the entire quantity of crystalline tacedinaline Forms A, B, and/or D, the novel crystalline tacedinaline TFA salt form, and/or amorphous tacedinaline, present. Nor should the carrier be otherwise incompatible with tacedinaline itself, or with crystalline tacedinaline Forms A, B, and D, the novel crystalline tacedinaline TFA salt form, and/or amorphous tacedinaline, as described herein, such as by producing any undesirable biological effect or otherwise interacting in a deleterious manner with any other component(s) of the pharmaceutical composition.

The solid unit dosage form may also include one or more other component typically used in formulating pharmaceutical dosage forms, as well known in the art, such as, for example: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar, calcium carbonate, potato or tapioca starch, alginic acid, certain silicates, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, and sodium lauryl sulfate. The solid unit dosage forms may also comprise buffering agents. They may optionally contain opacifying agents and can also be of a composition that they release the active ingredient(s) only, or preferentially, in a certain part of the intestinal tract, optionally, in a delayed manner. Other components useful in the unit dosage forms according to the invention include, but are not limited to, those disclosed in WO 2011/053876 A1. Remington's Pharmaceutical Sciences, Sixteenth Edition, E. W. Martin (Mack Publishing Co., Easton, Pa., 1980) discloses various carriers used in formulating pharmaceutical techniques for the preparation thereof. Solid unit dosage forms of pharmaceutical compositions of the invention can also be prepared with coatings and shells such as enteric coatings and other coatings well known in the pharmaceutical formulating art.

Solid unit dosage forms comprising the amorphous form of tacedinaline described herein may also comprise stabilizing excipients. Because crystalline forms are often more thermodynamically stable than amorphous forms, there is a driving force toward crystallization of the amorphous state, and thus a need to stabilize the formulation. Such stabilizing excipients may include, but are not limited to, polymers, celluloses, and organic acids. Exemplary stabilizing excipients include polyvinylpyrrolidone (PVP), hydroxypropyl cellulose (HPC), hydroxypropylmethyl cellulose (HPMC), hydroxypropyl methacrylamide (HMPA), polyethylene glycols (PEGs), and citric acid, to name a few.

It is well known that pharmaceutical excipients, such as carriers, fillers, binders, and the like, typically found in solid unit dosage forms, may make detection of a particular solid form of a compound, such as crystalline tacedinaline Forms A, B, and/or D, the novel crystalline tacedinaline TFA salt form, and/or amorphous tacedinaline, difficult. This may be due, for example, to interference in analytical techniques such as XRPD or IR. However, one of skill in the art, using techniques known in the art, should generally be able to determine whether a particular solid form is present.

Any of crystalline tacedinaline Forms A, B, and/or D, the novel crystalline tacedinaline TFA salt form, and/or amorphous tacedinaline, may also be used in, or used in preparation of, non-solid formulations, such as, for example, a solution, an injectable or inhalable formulation, or a patch. Such non-solid formulations are known in the art. In a non-solid formulation, the crystalline and/or amorphous form may, in various embodiments, not be maintained. For example, the crystalline and/or amorphous form may be dissolved in a liquid carrier. The crystalline and/or amorphous forms of the invention may provide advantages of handling stability and purity to the process of making such formulations.

In a further exemplary embodiment, the crystalline tacedinaline Forms A, B, and/or D, the novel crystalline tacedinaline TFA salt form, and/or amorphous tacedinaline, may be administered in a suspension.

In addition, any of crystalline tacedinaline Forms A, B, and/or D, the novel crystalline tacedinaline TFA salt form, and/or amorphous tacedinaline may be used as a starting material or intermediate in a process of preparing a different solid form of tacedinaline, or by converting one solid form to another. Additionally, in further embodiments contemplated herein, any of crystalline tacedinaline Forms A, B, and/or D, the novel crystalline tacedinaline TFA salt form, and/or amorphous tacedinaline, may be used in the preparation of solid formulations that do or do not ultimately contain any of crystalline tacedinaline Forms A, B, and/or D, the novel crystalline tacedinaline TFA salt form, and/or amorphous tacedinaline (for example, by conversion of one or more of crystalline tacedinaline Forms A, B, and/or D, the novel crystalline tacedinaline TFA salt form, and/or amorphous tacedinaline, to some other solid form). As used herein, the term "converting" with regard to converting one form to another is intended to include any step or condition that changes the solid form of the compound, such as, for example, a process that uses a particular form as an intermediate; a formulating step that causes intentional or unintended conversion, such as direct compression or wet granulation; exposure to heat and/or humidity; etc. By way of example only, the crystalline tacedinaline TFA salt form described herein may be used in a process for preparing crystalline tacedinaline Forms A and/or B, for example as an intermediate product.

The invention in various embodiments also relates to the treatment, prevention, and/or alleviation of neoplastic diseases, memory loss, and cognitive function disorders/impairments, comprising administering to a subject crystalline tacedinaline Forms A, B, and/or D, the novel crystalline tacedinaline TFA salt form, and/or amorphous tacedinaline, or a pharmaceutical composition comprising crystalline tacedinaline Forms A, B, and/or D, the novel crystalline tacedinaline TFA salt form, and/or amorphous tacedinaline. In further embodiments, methods of improving cognitive function in a normal subject and/or methods of promoting fear extinction in a subject comprising administering to a subject crystalline tacedinaline Forms A, B, and/or D, the novel crystalline tacedinaline TFA salt form, and/or amorphous tacedinaline, or a pharmaceutical composition comprising crystalline tacedinaline Forms A, B, and/or D, the novel crystalline tacedinaline TFA salt form, and/or amorphous tacedinaline, are disclosed. In various embodiments, a pharmaceutical composition administered comprises an effective amount of tacedinaline comprising crystalline tacedinaline Forms A, B, and/or D, the novel crystalline tacedinaline TFA salt form, and/or amorphous tacedinaline. These solid forms and pharmaceutical compositions containing them may, according to various embodiments, be administered using any amount, any form of pharmaceutical composition, and any route of administration effective for the desired treatment.

The crystalline tacedinaline Forms A, B, and/or D, the novel crystalline tacedinaline TFA salt form, and/or amorphous tacedinaline, according to the invention may be administered by any route known, such as, for example, orally, transdermally, intravenously, cutaneously, subcutaneously, nasally, intramuscularly, intraperitoneally, intracranially, and intracerebroventricularly.

In certain exemplary embodiments, the tacedinaline comprising crystalline tacedinaline Forms A, B, and/or D, the novel crystalline tacedinaline TFA salt form, and/or amorphous tacedinaline, may be administered at dosage levels of greater than about 0.001 mg/kg, such as greater than about 0.01 mg/kg or greater than about 0.1 mg/kg. For example, the dosage level may be from about 0.001 mg/kg to about 50 mg/kg, such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can also be administered to a subject. In one exemplary embodiment, a dosage of up to about 0.4 mg/kg, once a day for at least 2 consecutive days, such as for 14 consecutive days, may be administered.

In another exemplary embodiment, administration could be on an intermittent schedule. By way of example only, a dosage of up to about 0.1 mg/kg once a day for up to 56 consecutive days may be administered followed by a dosing holiday, and then an additional dosing schedule.

Further, administration less frequently than daily, such as, for example, every other day, may be chosen. In additional exemplary embodiments, administration with at least 2 days between doses may be chosen. By way of example only, dosing may be every third day, bi-weekly, or weekly. For example, a dosage of up to about 0.8 mg/kg every other day, may be given. As another example, a single, acute dose may be administered. By way of example a one-time dose of up to about 50 mg/kg may be administered, such as about 10 mg/kg, or about 2.2 mg/kg.

As discussed above, the amount required for treatment of a particular patient will depend upon a variety of factors well known in the medical arts, and may vary depending on, for example, the condition being treated. And, as also discussed, the pharmaceutical composition comprising the crystalline tacedinaline Forms A, B, and/or D, the novel crystalline tacedinaline TFA salt form, and/or amorphous tacedinaline, may be administered as a unit dosage form.

In further embodiments, the subject to which the crystalline tacedinaline Forms A, B, and/or D, the novel crystalline tacedinaline TFA salt form, and/or amorphous tacedinaline, is administered may undergo additional therapies in combination therewith. The combination therapies may be any therapy appropriate for the disease or disorder being treated. For example, the combination therapy may include behavioral therapy and/or additional pharmaceutical compounds. Exemplary behavioral therapies and additional pharmaceutical compounds that may be useful in combination therapies contemplated herein may include, but are not limited to, those disclosed in WO 2011/053876 A1.

In various embodiments, the pharmaceutical compositions or formulations comprising crystalline tacedinaline Forms A, B, and/or D, the novel crystalline tacedinaline TFA salt form, and/or amorphous tacedinaline, may be assembled into therapeutic, diagnostic, or research kits to facilitate their use in a particular application. Such a kit may comprise, for example, a housing, an effective amount of tacedinaline comprising crystalline tacedinaline Forms A, B, and/or D, the novel crystalline tacedinaline TFA salt form, and/or amorphous tacedinaline, formulated for oral, transdermal, intraveneous, cutaneous, subcutaneous, nasal, intramuscular, intraperitoneal, intracranial, and intracerebroventricular administration, and instructions for administering the tacedinaline to a subject in need thereof. Exemplary kits that may be useful include, but are not limited to, those disclosed in WO 2011/053876 A1.

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

The use of the terms "the," "a," "an," or other singular terms, is meant to include plural embodiments as well, and vice versa. In addition, it should be understood that all numbers herein are modified by "about," whether or not so stated.

Moreover, it should be understood that various features and/or characteristics of differing embodiments herein may be combined with one another. It is therefore to be understood that numerous modifications may be made to the illustrative embodiments without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

EXAMPLES

Example 1

Preparation and Characterization of a Mixture of Crystalline Tacedinaline Forms B and D

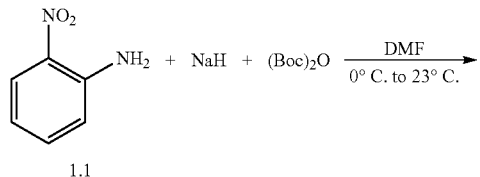

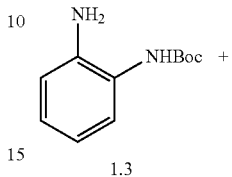

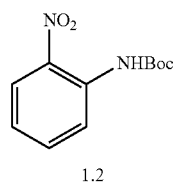

2-Nitroaniline 1.1 (10.0 g, 72.4 mmol, 1.0 eq.) was dissolved in dry DMF (100 mL) and cooled to 0° C. Subsequently, 60% NaH (1.91 g, 80.0 mmol, 1.1 eq.) was added slowly to the reaction mixture under an argon atmosphere. After 30 minutes, di-tert-butyl dicarbonate (17.3 g, 80.0 mmol, 1.1 eq.) dissolved in dry DMF (50 mL) was added slowly to the reaction mixture at that temperature. The reaction mixture was slowly brought to 23° C. and further stirred for 5 hours. After completion, the reaction mixture was poured into ice water and the precipitated solid was filtered, washed with water (3×100 mL), and dried. The material was dissolved in EtOAc/hexanes and passed through short silica gel column. The filtrate was concentrated in vacuo to provide tert-butyl-2-nitro phenylcarbamate 1.2 as a pale yellow solid. Yield 1.2=9.3 g (54%).

$^1$H NMR (500 Hz, d$^6$-DMSO) δ 9.58 (s, 1H), 7.95 (d, J=7.5 Hz, 1H), 7.66 (app d, J=3.5 Hz, 2H), 7.32-7.26 (m, 1H), 1.45 (s, 9H)

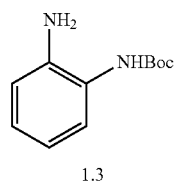

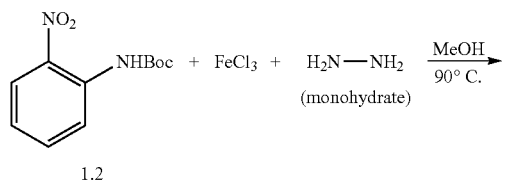

tert-Butyl-2-nitrophenylcarbamate 1.2 (9.0 g, 37.8 mmol, 1.0 eq.), iron (III) chloride (0.4 g, 2.3 mmol, 0.06 eq.), hydrazine monohydrate (51.0 g, 1592 mmol, 42 eq.) and MeOH (150 mL) were combined and heated to 90° C. After vigorously stirring for 2-3 hours, the reaction mixture was filtered hot through celite and washed with EtOAc. The solvents were removed under reduced pressure. This crude residue was diluted with cold water. The resultant solid was filtered and washed with hexane to afford tert-butyl 2-aminophenyl carbamate 1.3 as an off-white solid. Yield 1.3=7 g (90%).

$^1$H NMR (500 Hz, d$^6$-DMSO) δ 8.25 (s, 1H), 7.16 (d, J=7.5 Hz, 1H), 6.83 (t, J=7.5 Hz, 1H), 6.66 (d, J=7.5 Hz, 1H), 6.52 (t, J=7.5 Hz, 1H), 4.80 (s, 2H), 1.45 (s, 9H); MS (ESI+): m/z 231 [M+Na]$^+$.

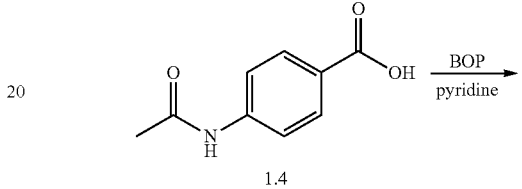

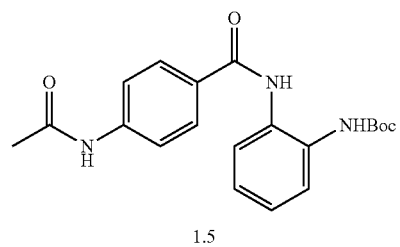

tert-Butyl 2-aminophenyl carbamate 1.3 (3.0 g, 14.4 mmol, 1 eq.), 4-acetamido benzoic acid 1.4 (2.8 g, 15.8 mmol, 1.1 equiv.), and (benzotriazol-1-yloxy)tris (dimethylamino) phosphonium hexafluorophosphate (7.6 g, 17.3 mmol, 1.2 eq.) were dissolved in pyridine (20 mL). After stirring at 23° C. for 48 hours, the reaction mixture was added to water and stirred. The resultant precipitated solid was filtered, washed with water, washed with ether, and dried under vacuum to provide tert-butyl (2-(4-acetamidobenzamido)phenyl)carbamate 1.5. Yield 1.5=4.8 g (90%).

$^1$H NMR (500 Hz, d$^6$-DMSO) δ 10.23 (s, 1H), 9.73 (bs, 1H), 8.66 (bs, 1H), 7.90 (d, J=8.5 Hz, 2H), 7.72 (d, J=9 Hz, 2H), 7.53 (t, J=8.5 Hz, 2H), 7.22-7.12 (m, 2H), 2.09 (s, 3H), 1.45 (s, 9H); MS (ESI+): m/z 392 [M+Na]$^+$.

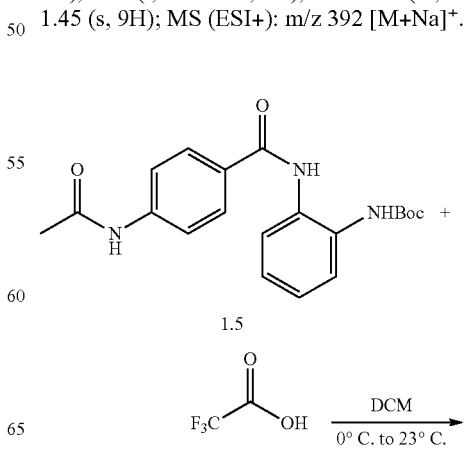

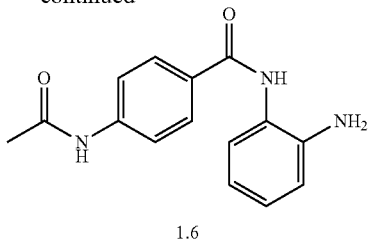

1.6

To a 0° C. solution of tert-butyl (2-(4-acetamidobenzamido)phenyl) carbamate 1.5 (3.5 g, 9.5 mmol) in dry dichloromethane (55 mL) was added trifluoroacetic acid (22 mL) dropwise. The mixture was allowed to slowly warm to 23° C. for 2 hours until the reaction was complete. The solvents were removed in vacuo. The reaction mixture was diluted with water and the pH was adjusted to ~8 with a saturated aqueous solution of sodium bicarbonate. The resulting precipitate was filtered, washed with water and ether, and dried under vacuum to afford 4-acetamido-N-(2-aminophenyl)benzamide 1.6 as an off-white solid. Yield 1.6=2.4 g (96%).

$^1$H NMR (500 Hz, d$^6$-DMSO) δ 10.18 (s, 1H), 9.54 (s, 1H), 7.93 (d, J=8.5 Hz, 2H), 7.69 (d, J=8.5 Hz, 2H), 7.15 (d, J=7.5 Hz, 1H), 6.96 (t, J=7.5 Hz, 1H), 6.78 (d, J=7.5 Hz, 1H), 6.59 (t, J=7.5 Hz, 1H), 4.88 (s, 2H), 2.08 (s, 3H). MS (ESI+): m/z 269.9 [M+H]$^+$.

Figure 13:
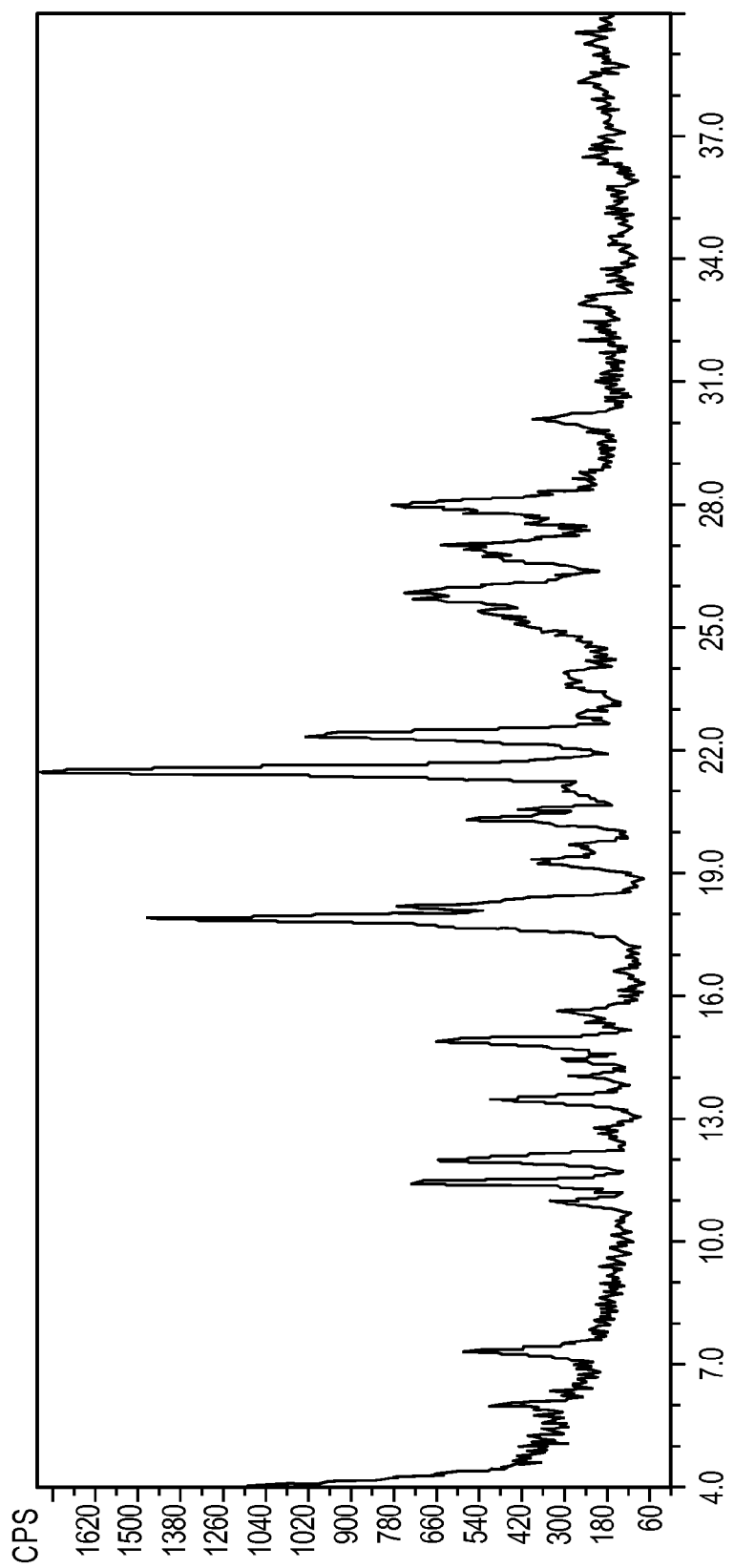
FIG. 13 shows an exemplary XRPD pattern of an embodiment of a mixture of crystalline tacedinaline Forms B and D.
Figure 14:
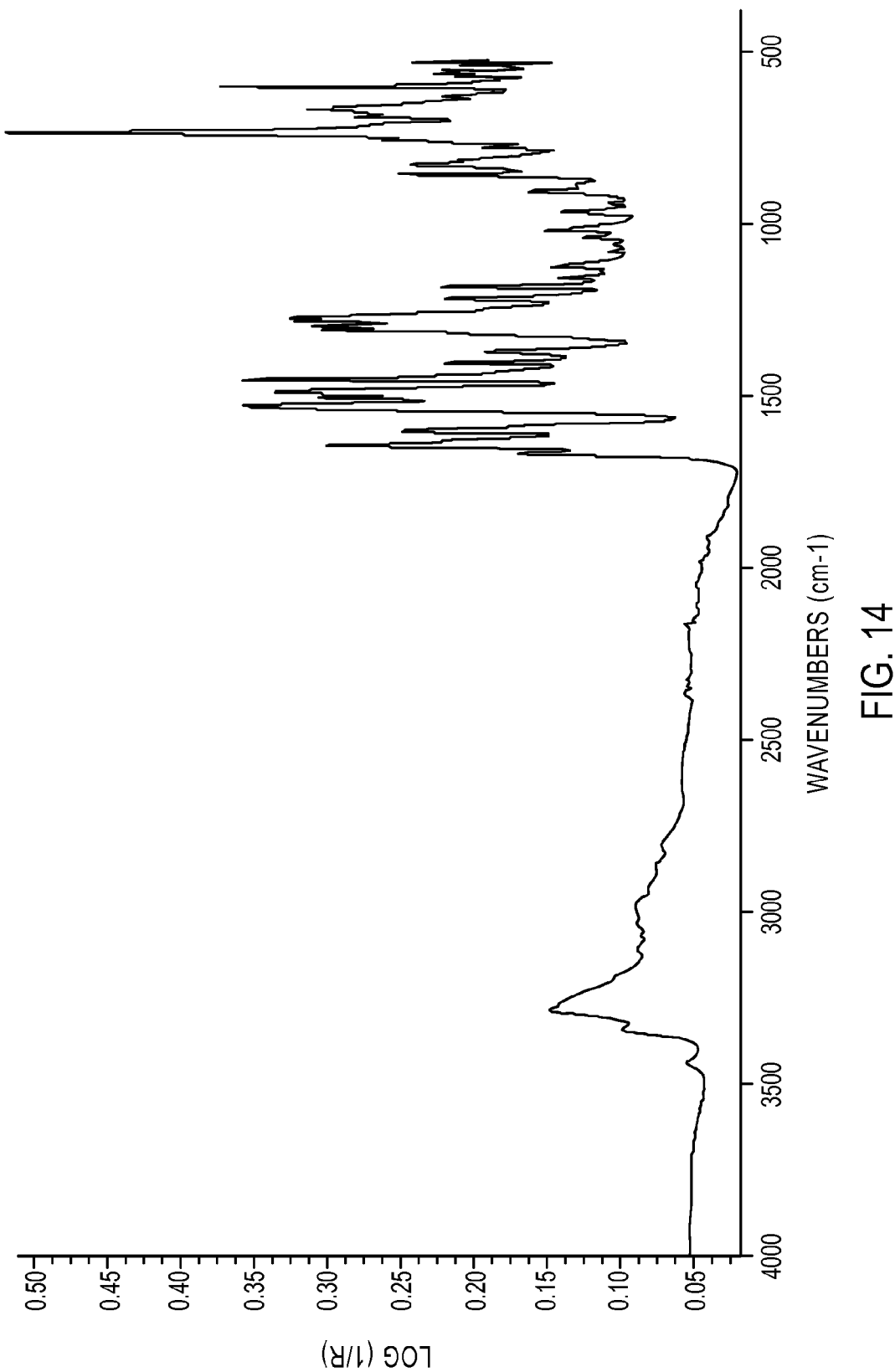
FIG. 14 shows an exemplary IR spectrum of an embodiment of a mixture of crystalline tacedinaline Forms B and D.
Figure 15:
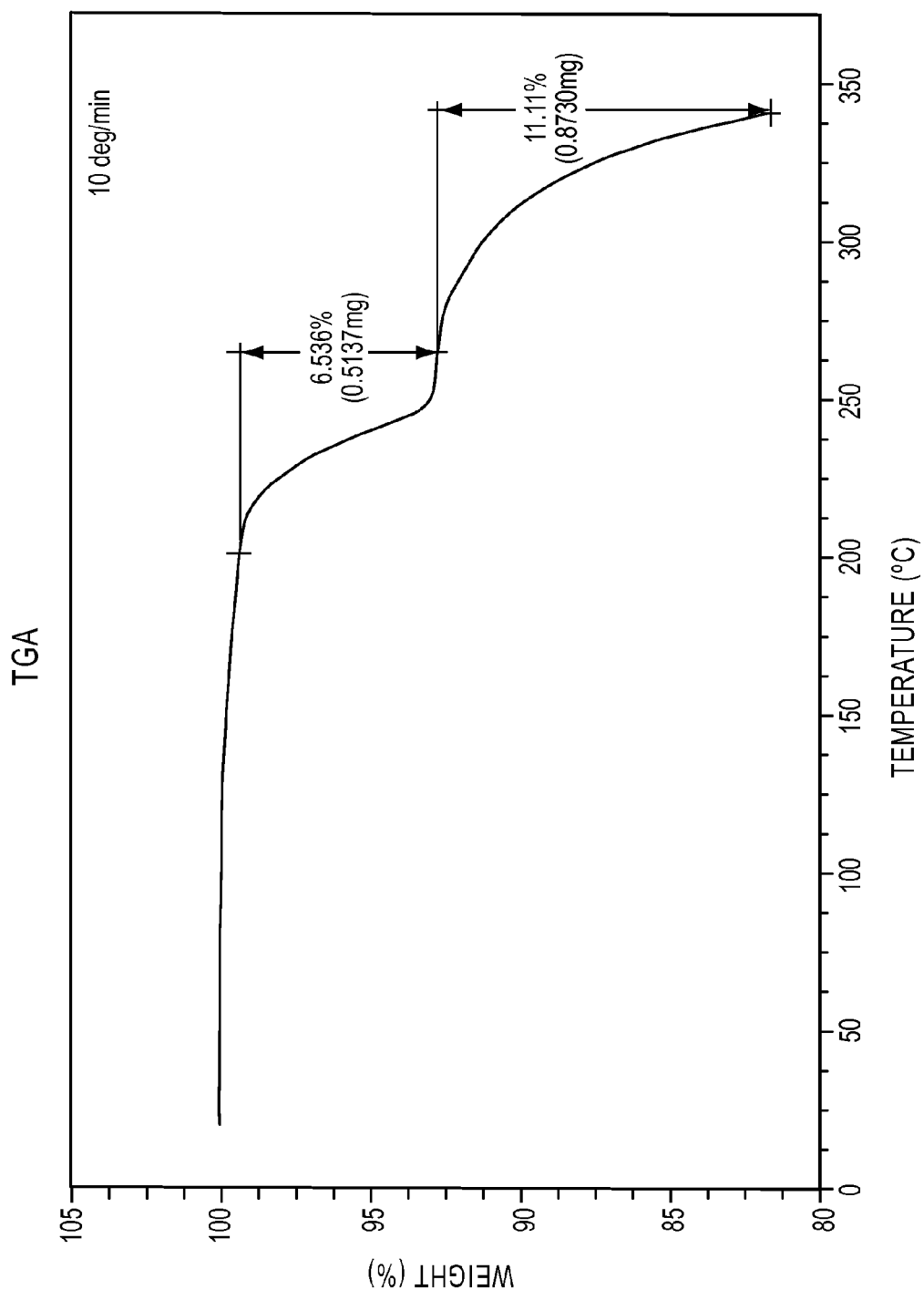
FIG. 15 shows an exemplary TGA profile of an embodiment of a mixture of crystalline tacedinaline Forms B and D.
Figure 16:
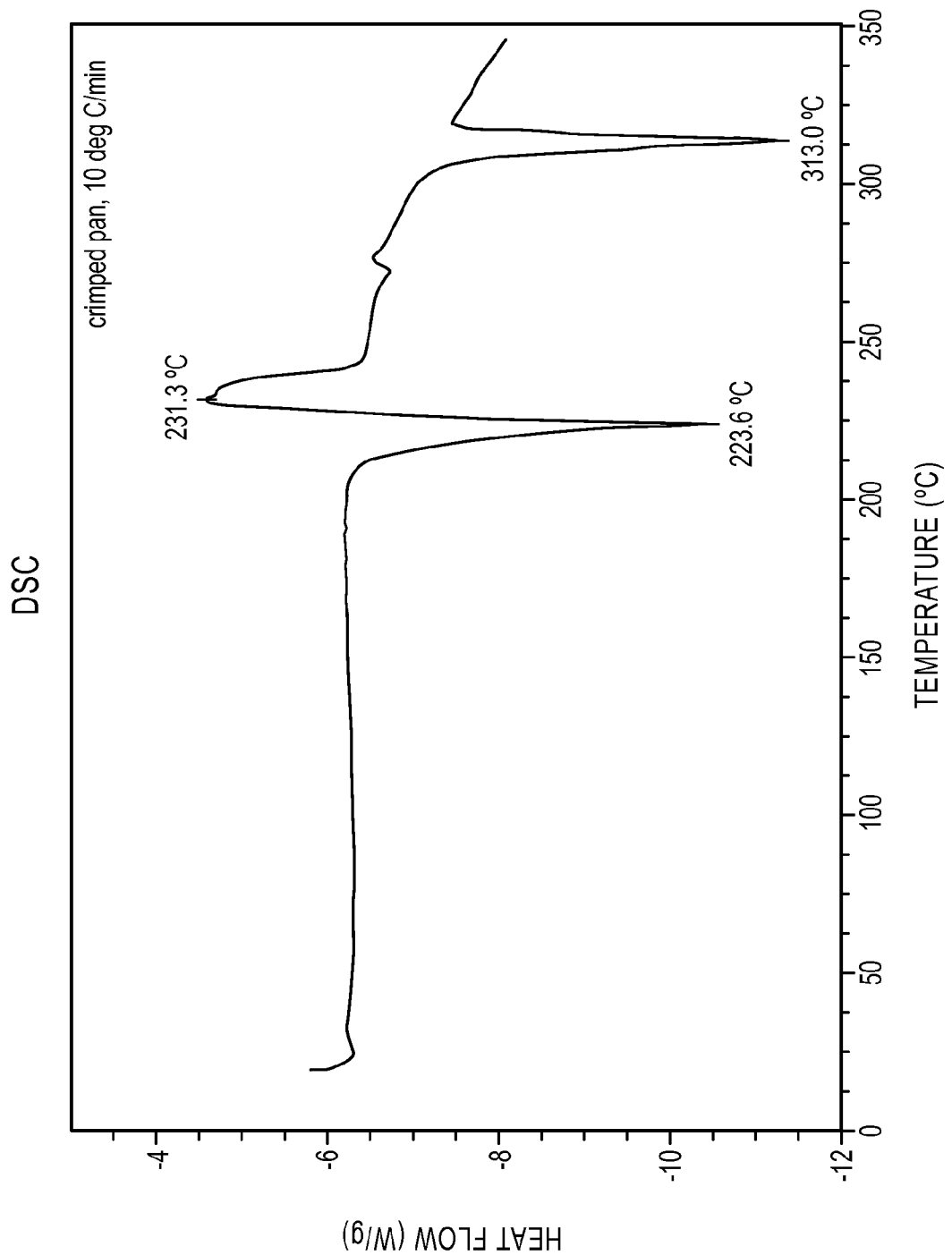
FIG. 16 shows an exemplary DSC thermogram of an embodiment of a mixture of crystalline tacedinaline Forms B and D.

Analytical data were obtained on the final product 1.6: the XRPD pattern was as shown in FIG. 13, the IR spectrum was substantially as shown in FIG. 14, the TGA profile was substantially as shown in FIG. 15, and the DSC trace was substantially as shown in FIG. 16.

The analytical data obtained on product 1.6 indicate that it is a mixture of crystalline tacedinaline Forms B and D.

Example 2

Preparation and Characterization of Crystalline Tacedinaline Form A

A mixture of 202.3 mg of the mixture of crystalline tacedinaline Forms B and D (1.6) from Example 1 and 15 mL of a 2:1 (volume:volume) solution of ethanol:water was brought to gentle reflux. Most of the solid dissolved. The mixture was filtered hot through filter paper. The filtrate, from which some solid had separated during the filtration, was reheated to gentle reflux and additional ethanol:water solution was added to bring the total volume back to about 15 mL. After all of the solid had dissolved, the mixture was removed from the hot plate, covered, and allowed to cool to ambient temperature. Crystals formed. The mixture was placed in the refrigerator for about 15 minutes and then filtered to give 125.6 mg of crystalline solid 2.1. A portion of that sample was ground using an agate mortar and pestle to give the final product, 2.2.

Figure 3:
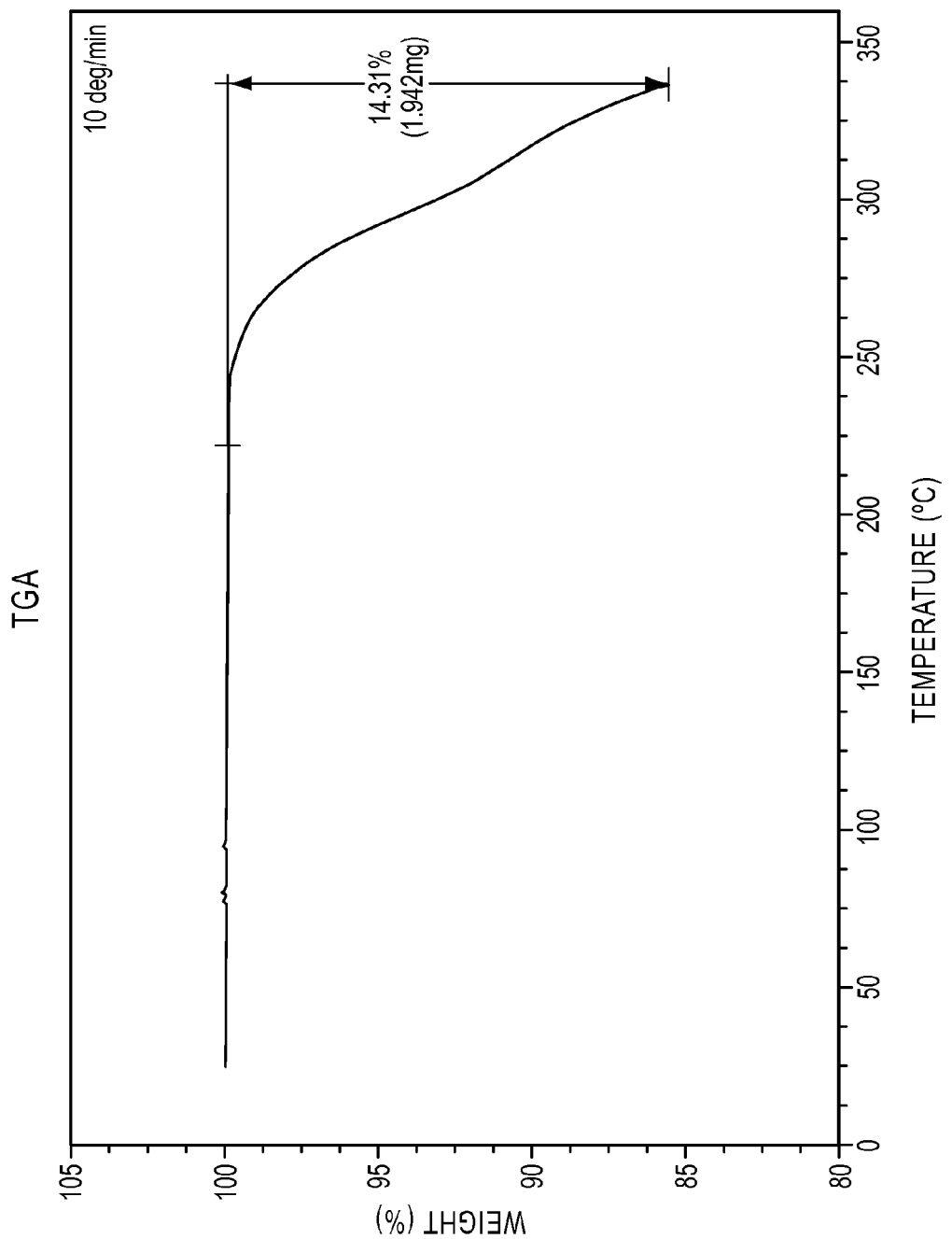
FIG. 3 shows an exemplary TGA profile of an embodiment of crystalline tacedinaline Form A.
Figure 4:
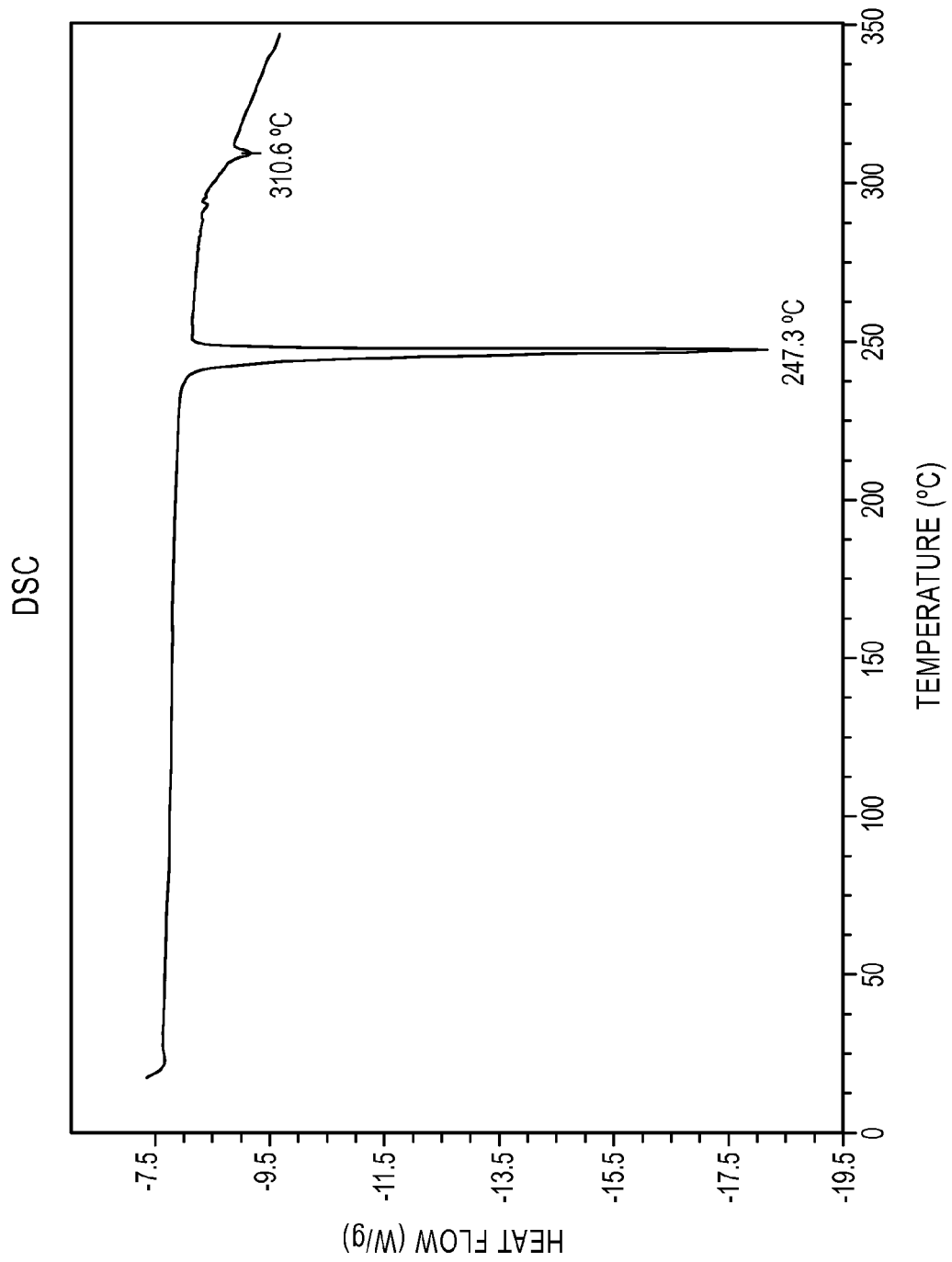
FIG. 4 shows an exemplary DSC thermogram of an embodiment of crystalline tacedinaline Form A.
Figure 5A:
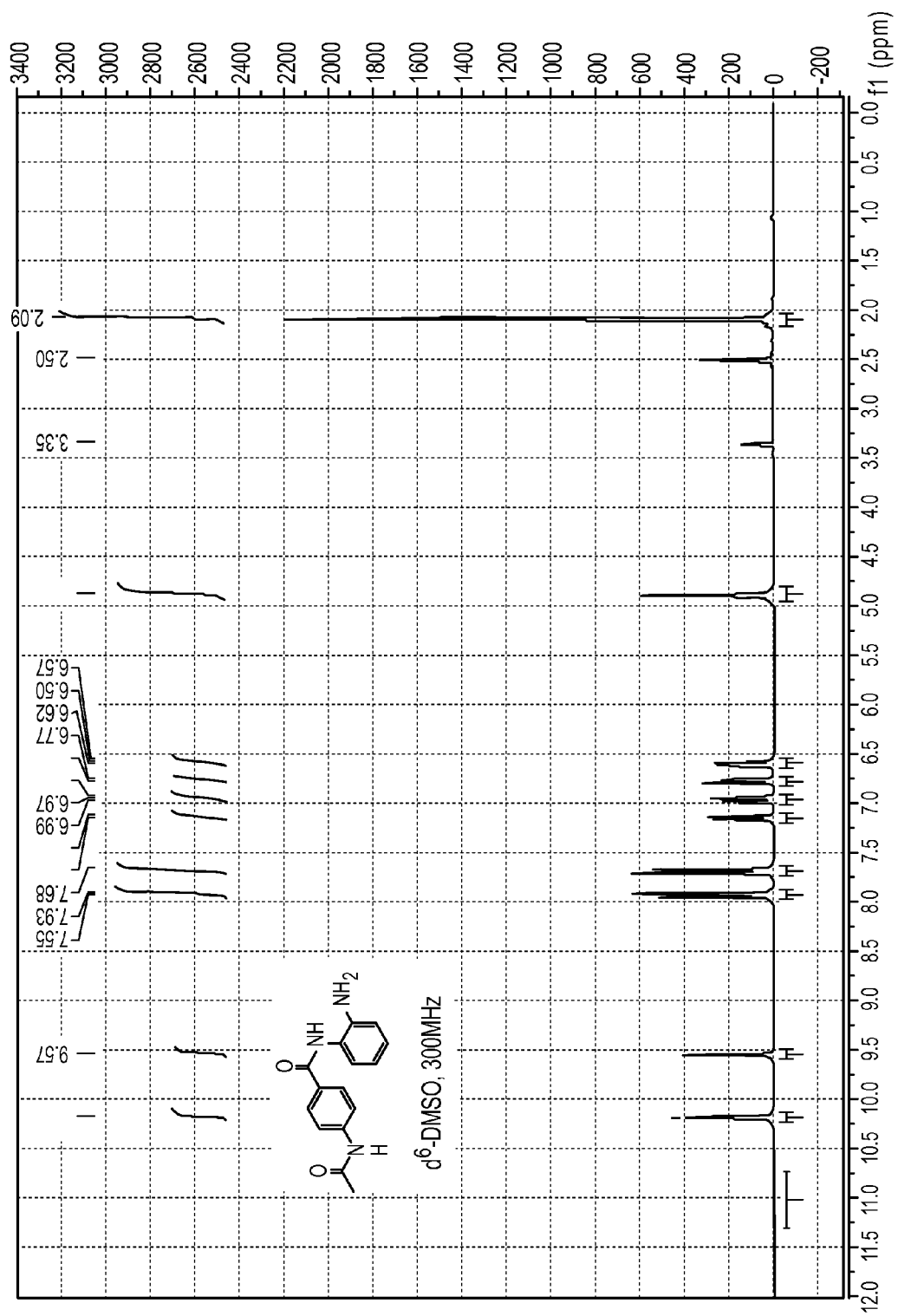
FIGS. 5A-5C show exemplary $^1$H-NMR spectra of an embodiment of crystalline tacedinaline Form A.
Figure 5B:
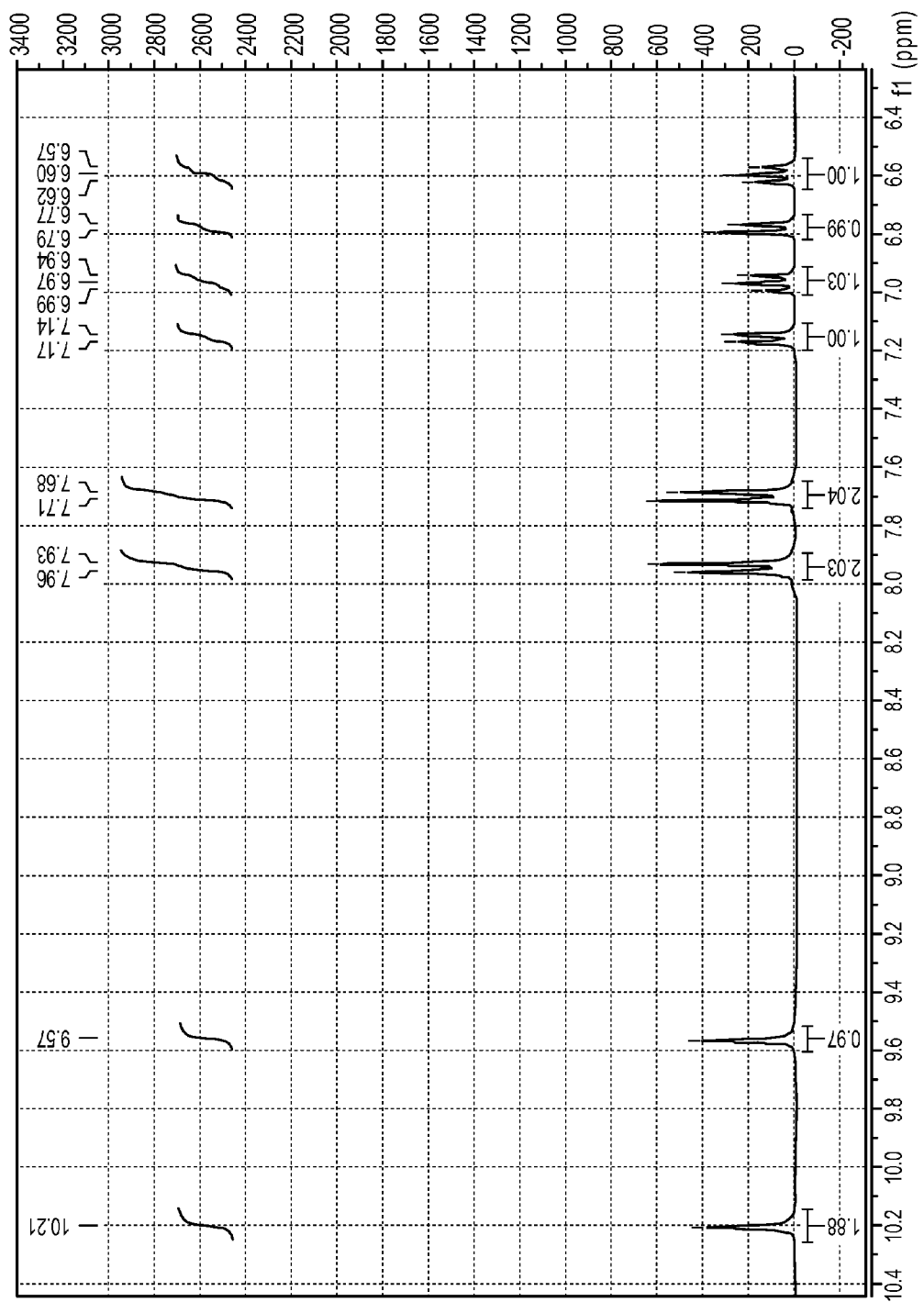
Figure 5C:
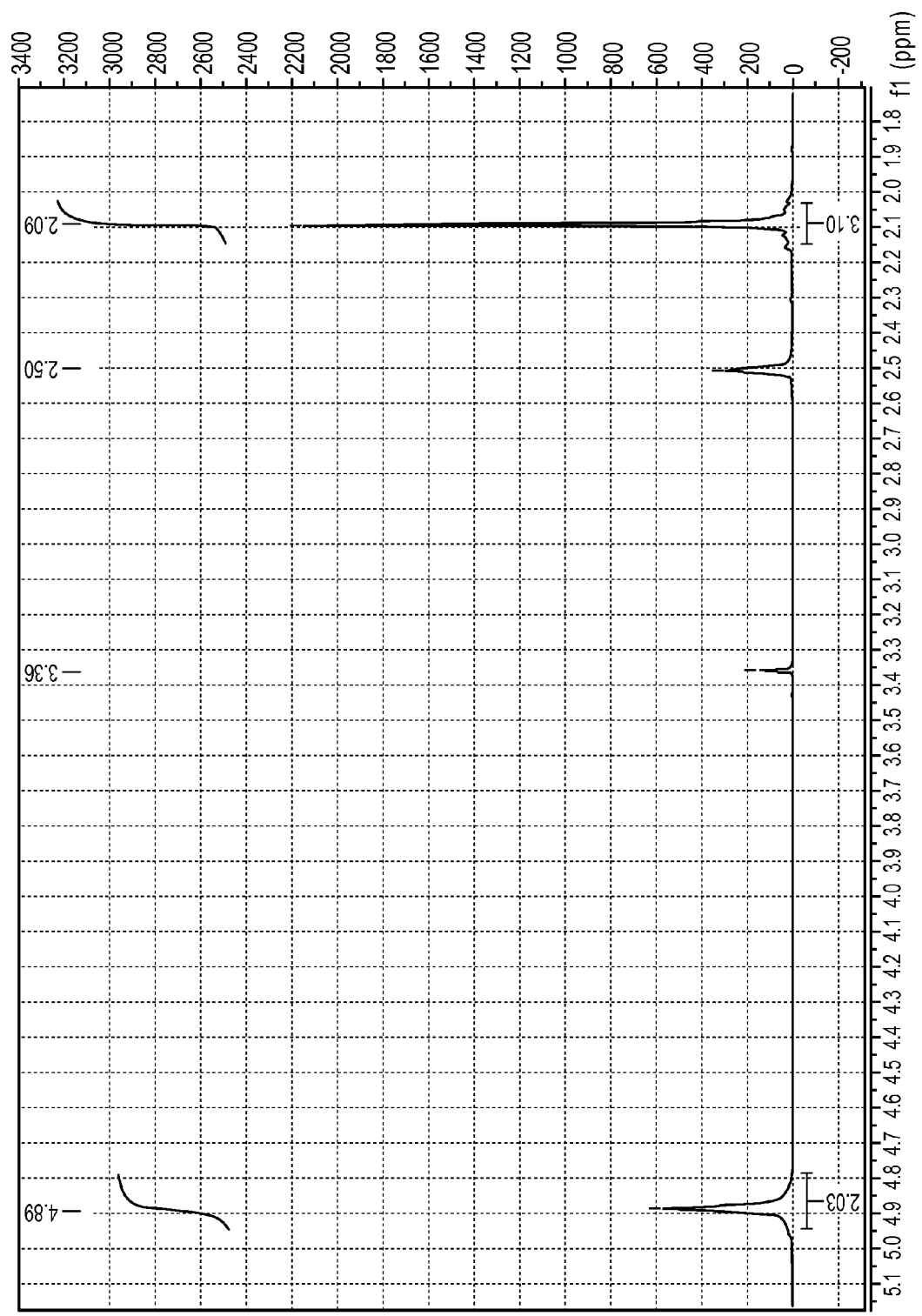
Figure 6A:
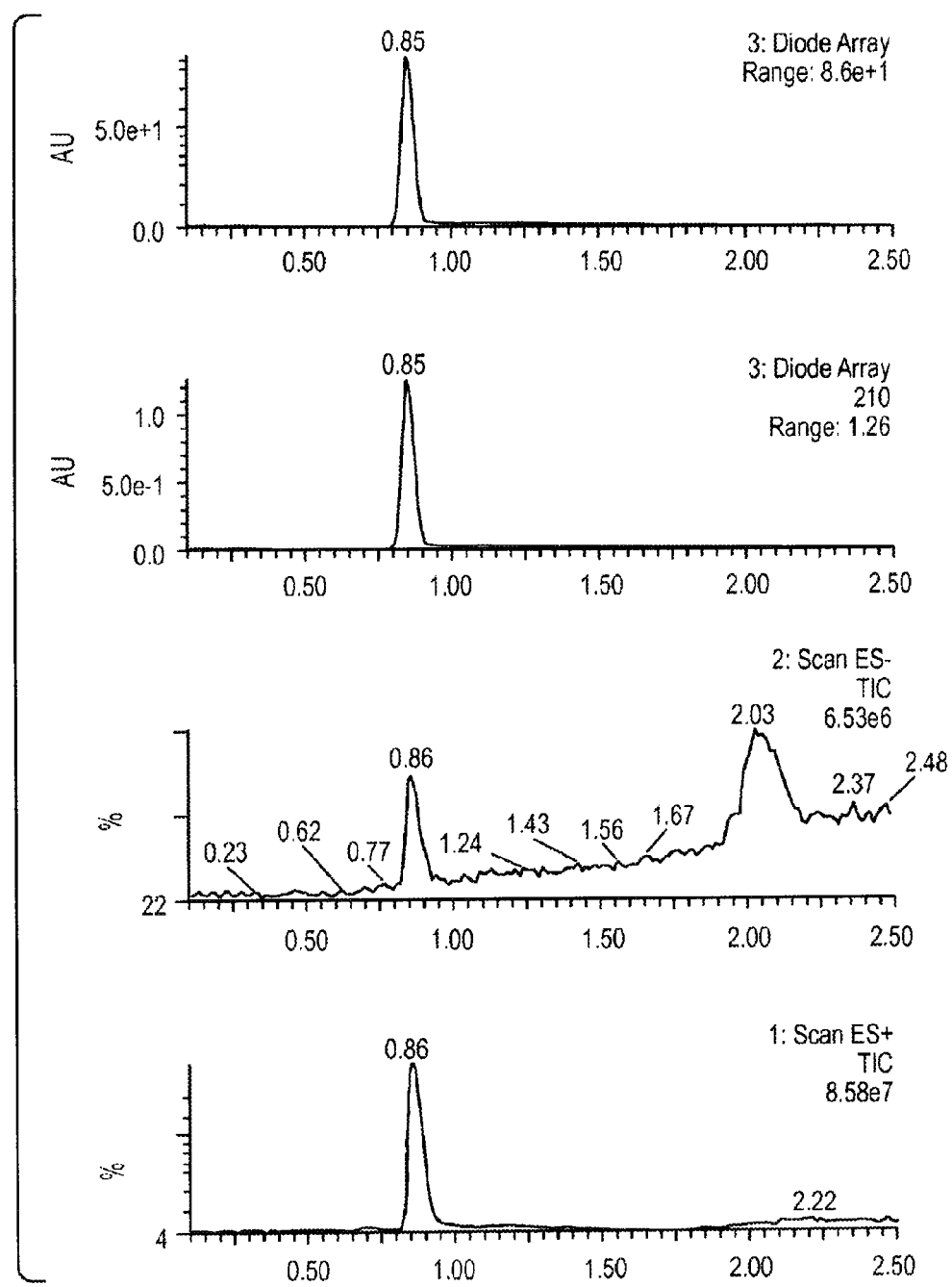
FIGS. 6A-6B show exemplary LC/MS data for an embodiment of crystalline tacedinaline Form A.
Figure 6B:
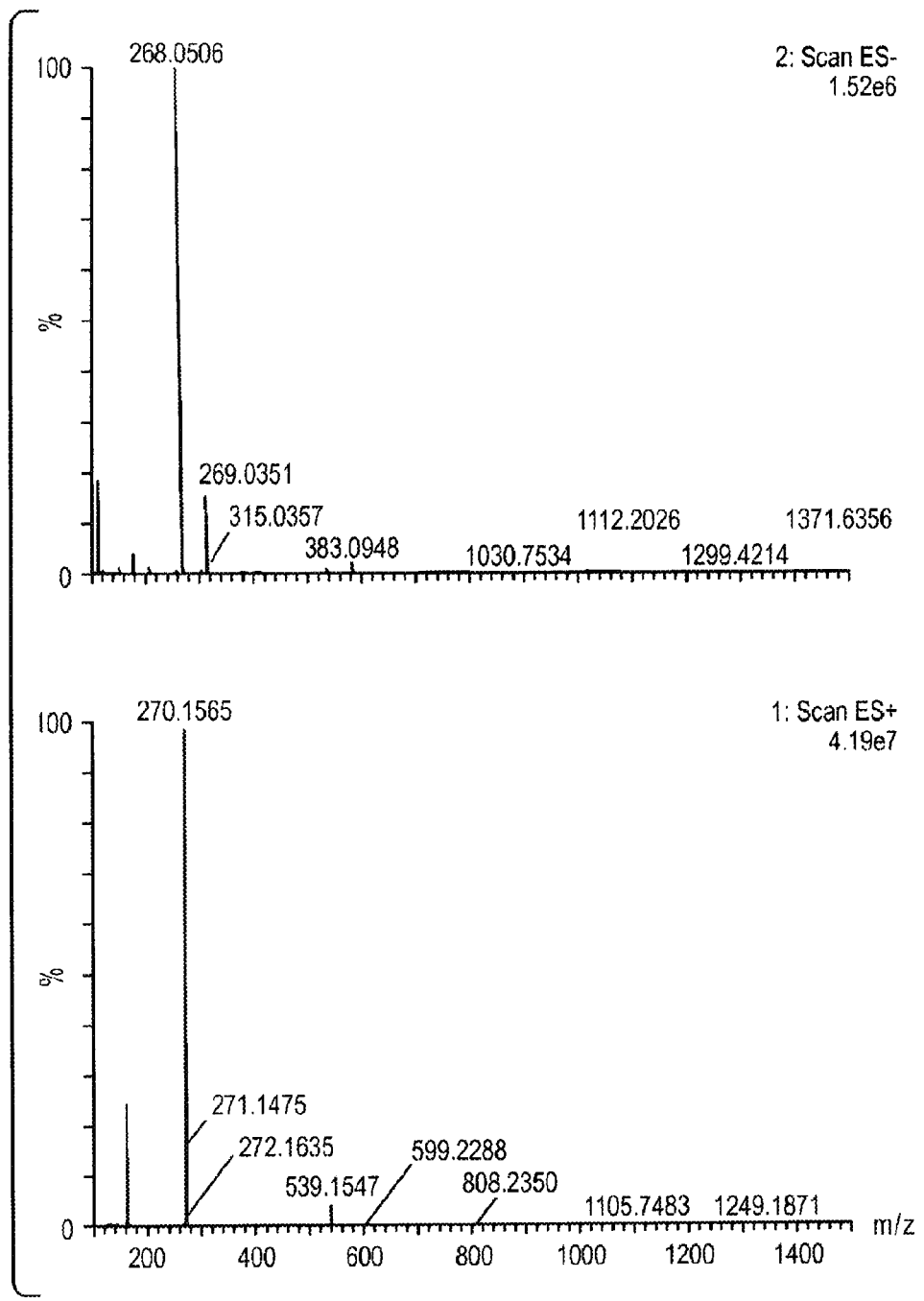

Analytical data were obtained on the final product 2.2: the XRPD pattern was as shown in FIG. 1A, the IR spectrum was as shown in FIG. 2, the TGA profile was as shown in FIG. 3, the DSC trace was as shown in FIG. 4, the $^1$H-NMR spectrum was as shown in FIGS. 5A-5C, and the LC/MS data was as shown in FIG. 6.

The analytical data obtained on product 2.2 indicate that it is crystalline tacedinaline Form A.

Example 3

Single Crystal X-ray Analysis of Crystalline Tacedinaline Form A

A single crystal suitable for x-ray diffraction analysis was selected from the product 2.1 of Example 2, above.

The crystallographic data collection and single crystal parameters for the tacedinaline Form A crystal are set forth in Table 9.

TABLE 9

| | |
|---|---|
| formula | C$_{15}$H$_{15}$N$_3$O$_2$ |
| formula weight | 269.31 |
| space group | P 1 21/c 1 (No. 14) |
| a (Å) | 6.5031(3) |
| b (Å) | 9.0907(4) |
| c (Å) | 22.6701(16) |
| β (degrees) | 95.010(7) |
| volume (Å$^3$) | 1335.08(13) |
| Z | 4 |
| d$_{calc}$ (g cm$^{-3}$) | 1.340 |
| crystal dimensions (mm) | 0.18 × 0.18 × 0.05 |
| temperature (K) | 150 |
| radiation (wavelength in Å) | Cu Kα (1.54184) |
| monochromator | graphite |
| linear abs coef (mm−1) | 0.706 |
| absorption correction applied | empirical$^a$ |
| transmission factors (min, max) | 0.83, 0.97 |
| diffractometer | Nonius Kappa CCD |
| h, k, l range | −7 to 7 −10 to 10 −25 to 26 |
| 2θ range (deg) | 13.67-132.87 |
| mosaicity (deg) | 2.97 |
| programs used | SHELXTL |
| F$_{000}$ | 568.0 |
| weighting | 1/[σ$^2$(Fo$^2$) + (0.0882P)$^2$ + 0.0000P] where P = (Fo$^2$ + 2Fc$^2$)/3 |
| data collected | 14576 |
| unique data | 1973 |
| R$_{int}$ | 0.063 |
| data used in refinement | 1973 |
| cutoff used in R-factor calculations | F$_o^2$ > 2.0s(F$_o^2$) |
| data with I > 2.0s(I) | 1201 |
| refined extinction coef | 0.0049 |
| number of variables | 199 |
| largest shift/esd in final cycle | 0.00 |
| R(F$_o$) | 0.060 |
| Rw(F$_o^2$) | 0.138 |
| goodness of fit | 1.059 |

$^a$Sheldrick, G. M., SADABS 1996, Gottingen, Germany.

Example 4

Preparation and Characterization of Crystalline Tacedinaline Form A

A slurry of 50.7 mg of the mixture of crystalline tacedinaline Forms B and D (1.6) from Example 1 and about 1 mL of a 4:1 (volume:volume) solution of acetonitrile:water was stirred at ambient temperature overnight. Filtration and vacuum drying of the filter cake (ambient temperature, diaphragm pump pressure, 1 hour) yielded 40.4 mg of white, crystalline solid.

Analytical data were obtained on the product: the XRPD pattern was as shown in FIG. 1B, the IR spectrum was substantially as shown in FIG. 2, the TGA profile was substantially as shown in FIG. 3, and the DSC trace was substantially as shown in FIG. 4.

The analytical data obtained on the product indicate that it is crystalline tacedinaline Form A.

Example 5A

Preparation and Characterization of Crystalline Tacedinaline Form B

A mixture of 100.5 mg of a mixture of crystalline tacedinaline Forms B and D (1.6) from Example 1 and 30 mL of acetone was brought to gentle reflux. All solids dissolved. The solution was filtered hot through filter paper. The clear filtrate was brought to gentle reflux and the volume reduced to about 10 mL by boiling. It was allowed to stand at room temperature overnight, then in the refrigerator and freezer for a short time. No crystallization occurred, so the solution was again brought to gentle reflux and reduced in volume to about 3 mL by boiling. It was allowed to cool to ambient temperature and crystallization occurred. After about one hour at ambient temperature it was placed in the refrigerator for about 30 minutes and filtered to give 14.3 mg of white, crystalline solid.

Figure 9:
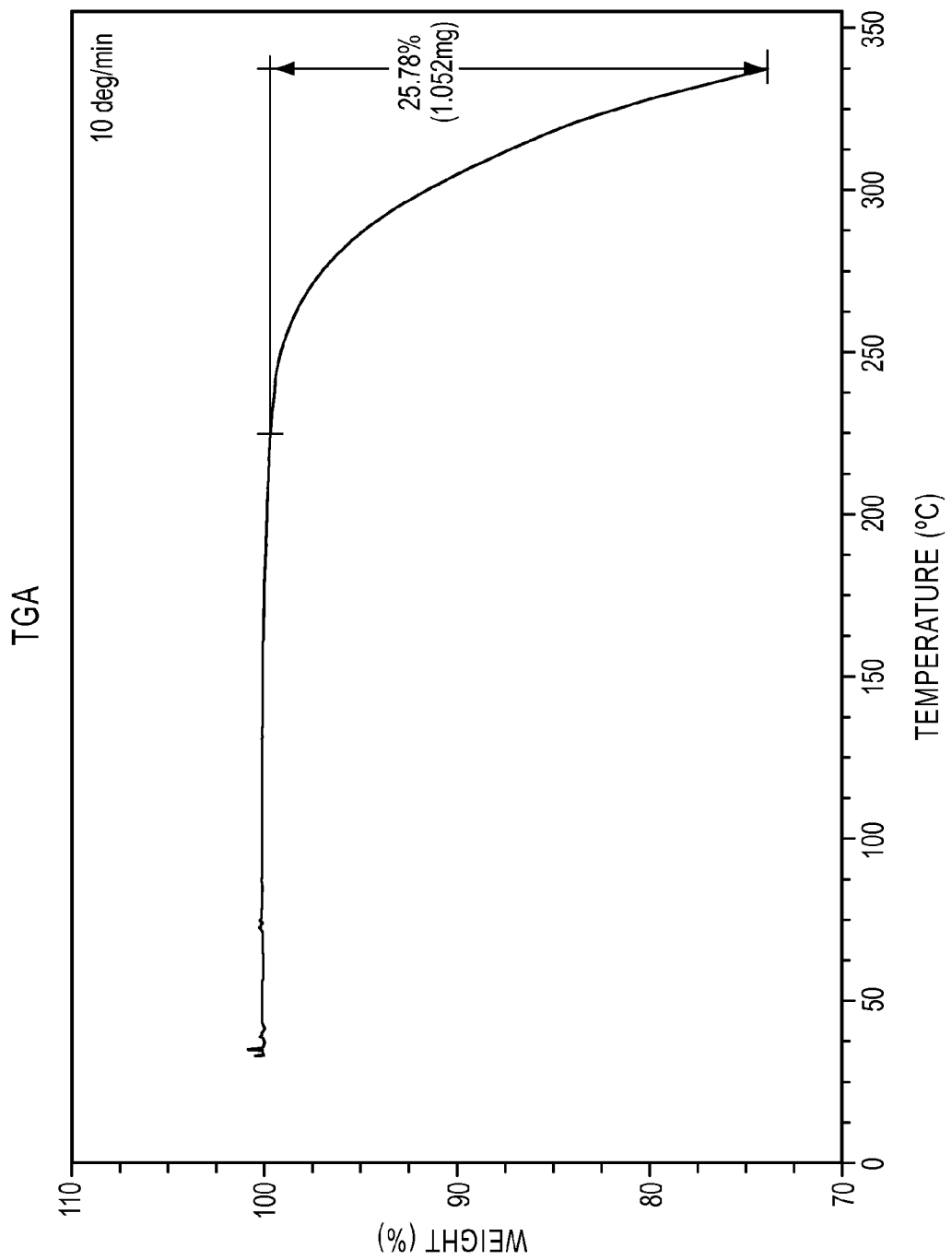
FIG. 9 shows an exemplary TGA profile of an embodiment of crystalline tacedinaline Form B.
Figure 10:
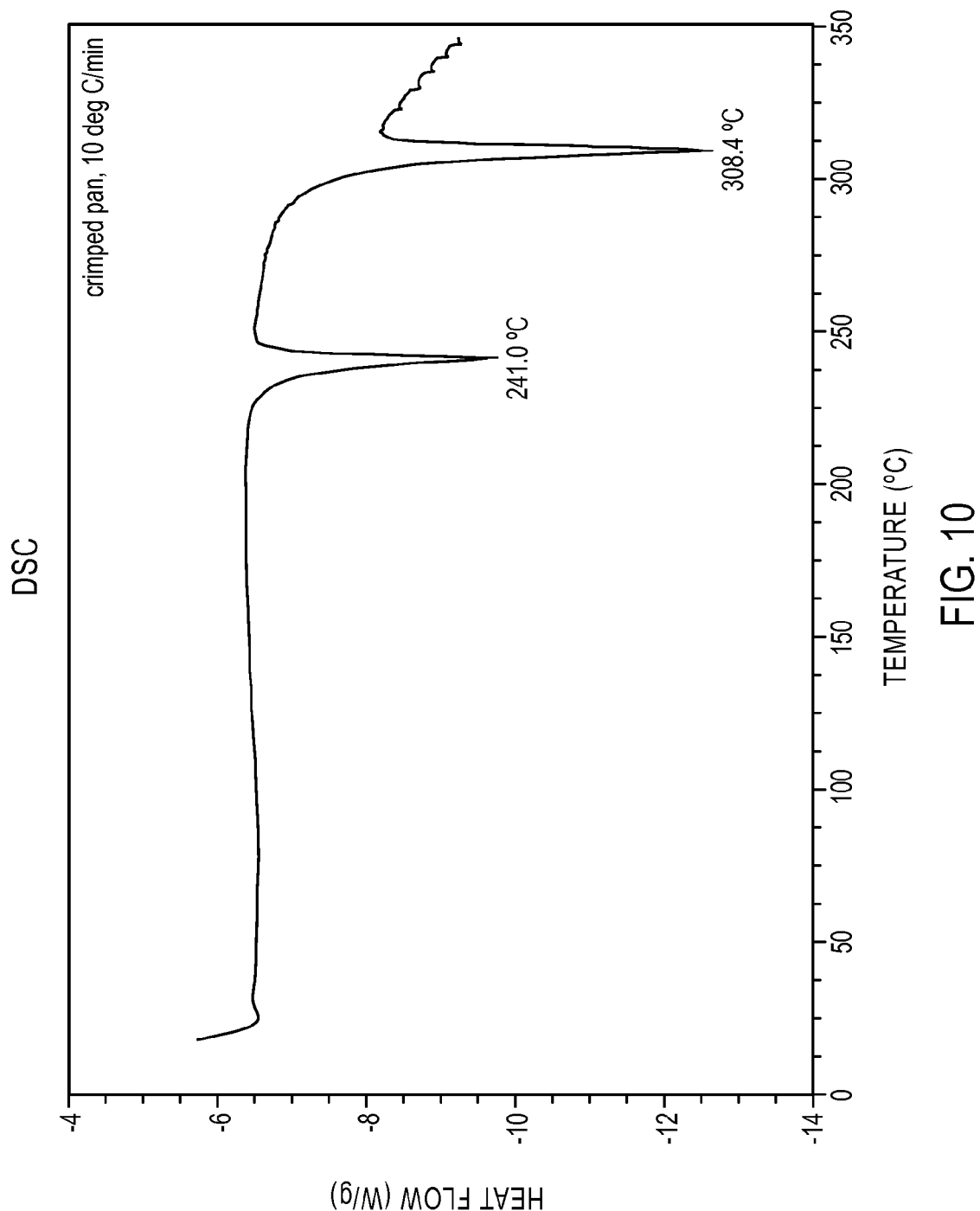
FIG. 10 shows an exemplary DSC thermogram of an embodiment of crystalline tacedinaline Form B.
Figure 11A:
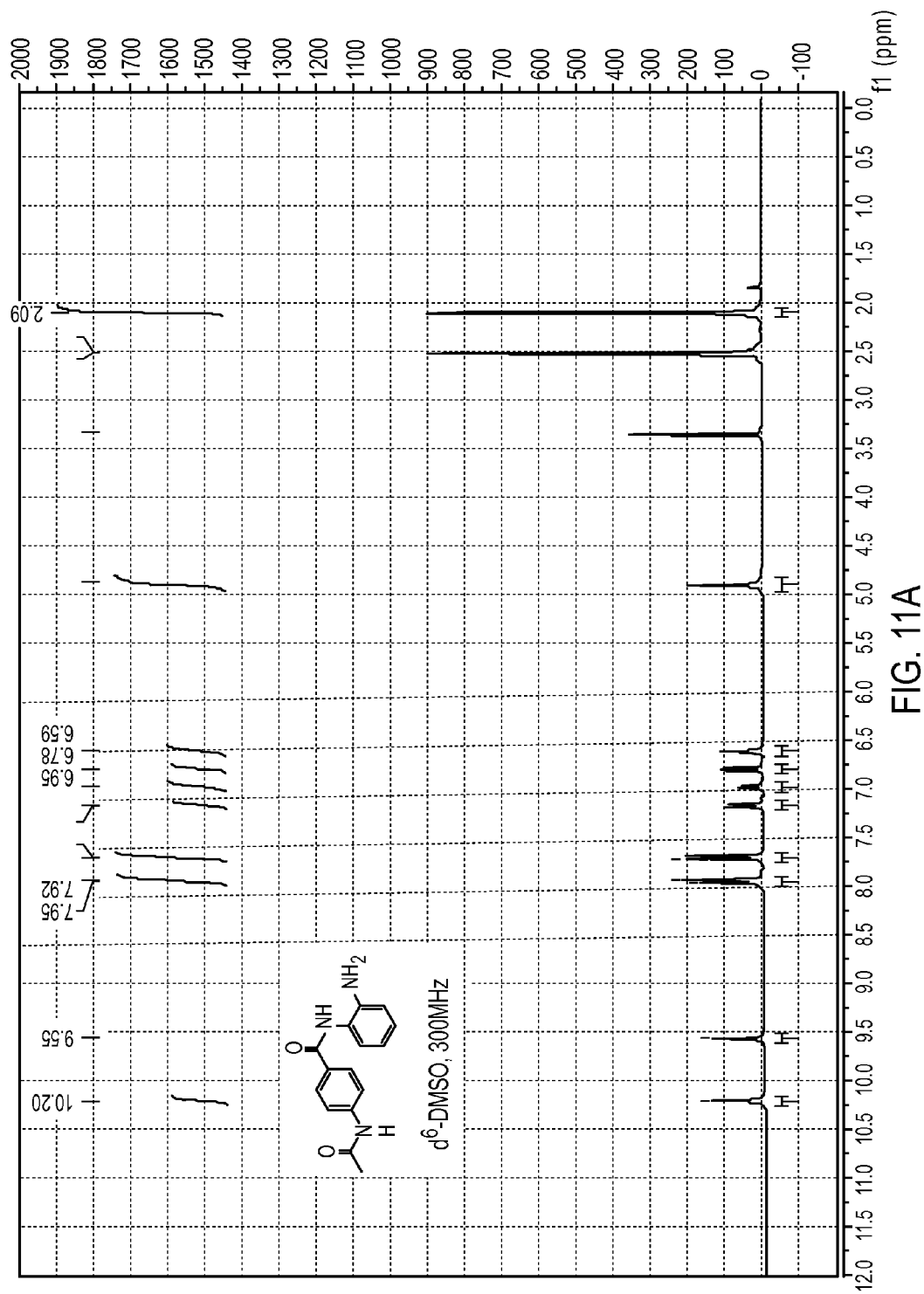
FIGS. 11A-11C show exemplary $^1$H-NMR spectra of an embodiment of crystalline tacedinaline Form B.
Figure 11B:
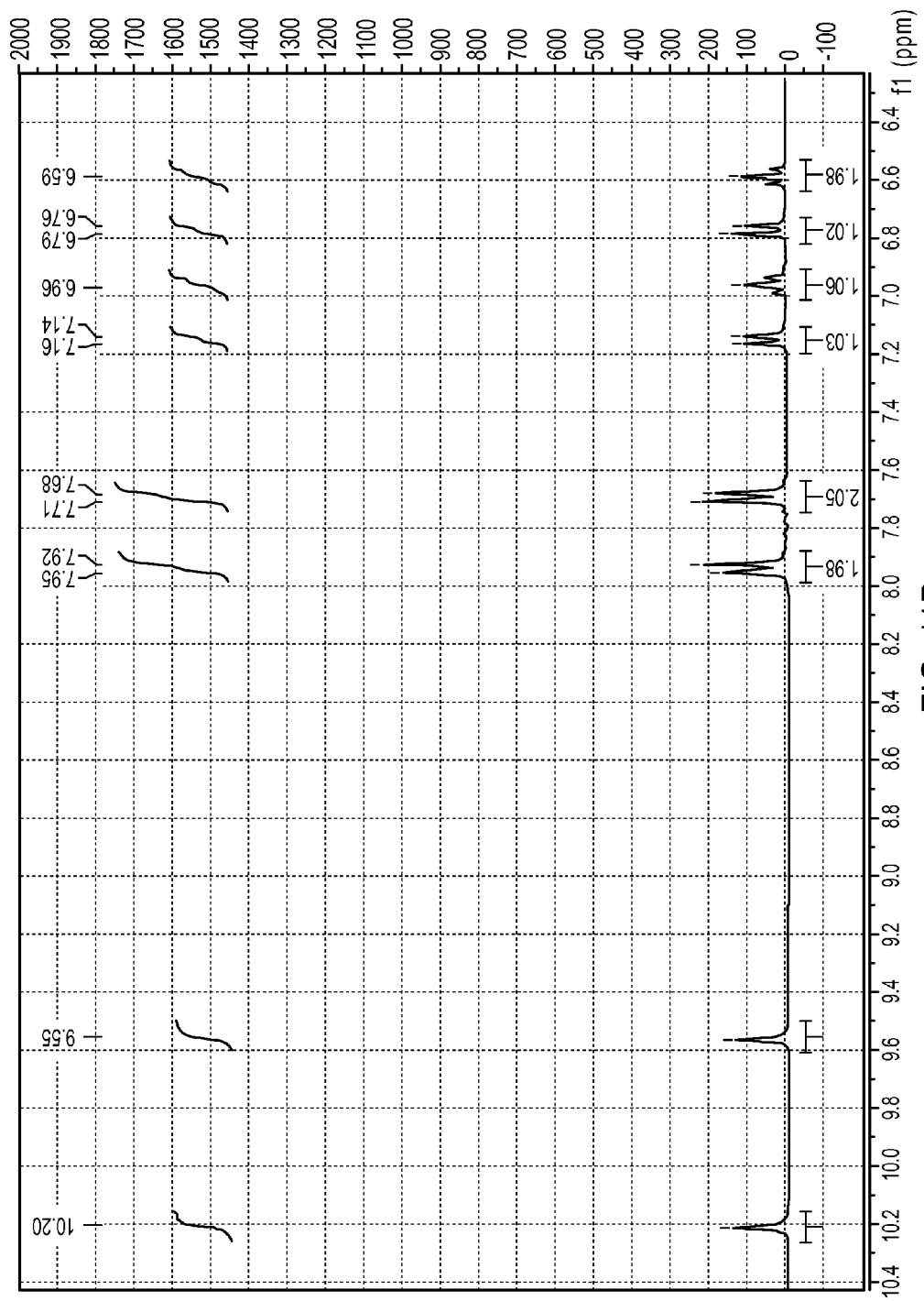
Figure 11C:
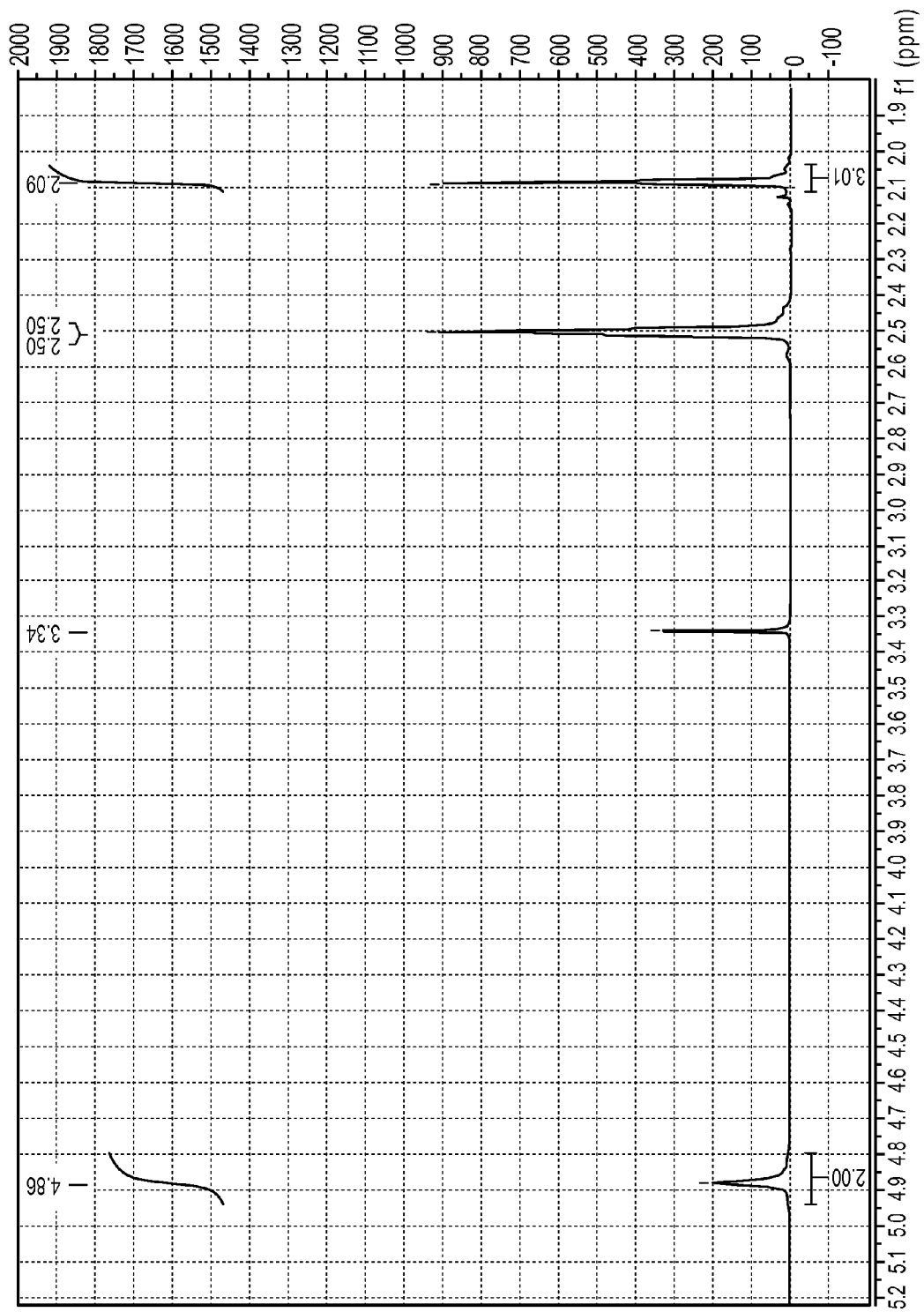
Figure 12A:
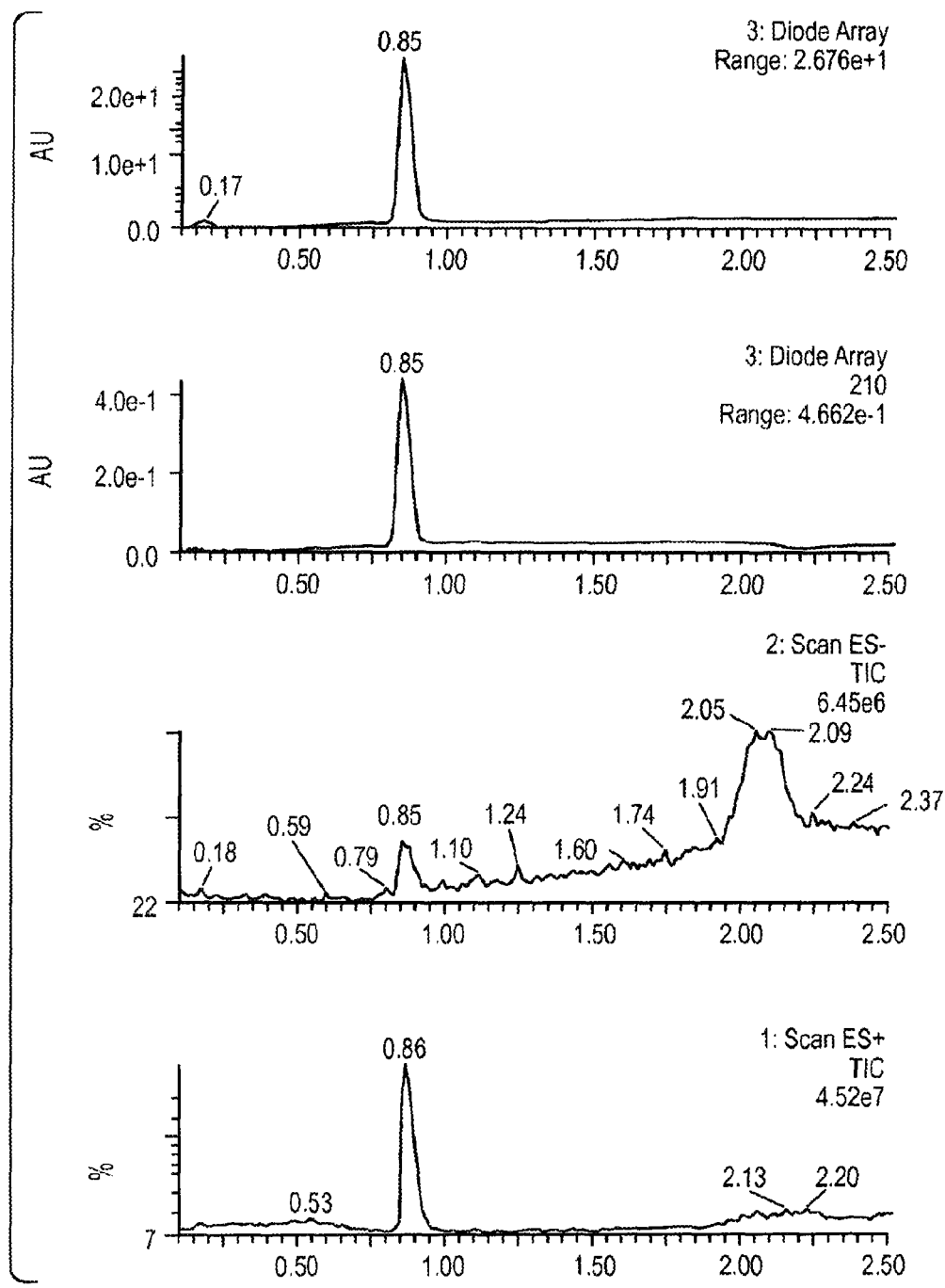
FIGS. 12A-12B show exemplary LC/MS data for an embodiment of crystalline tacedinaline Form B.
Figure 12B:
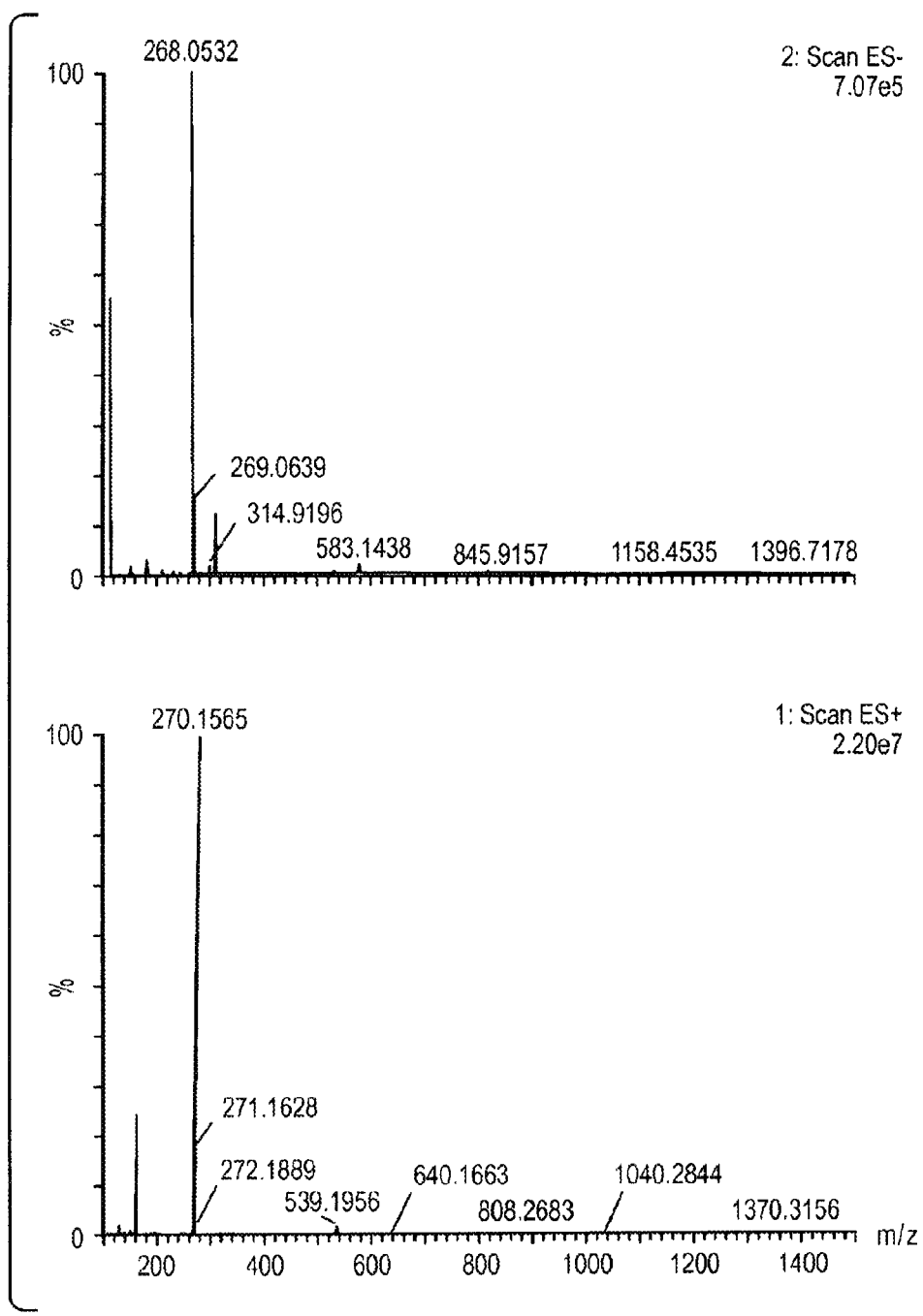

Analytical data were obtained on the product: the XRPD pattern was as shown in FIG. 7B, the IR spectrum was as shown in FIG. 8, the TGA profile was as shown in FIG. 9, the DSC trace was as shown in FIG. 10, the $^1$H-NMR spectrum was as shown in FIGS. 11A-11C, and the LC/MS data was as shown in FIG. 12.

The analytical data obtained on the product indicate that it is crystalline tacedinaline Form B.

Example 5B

Preparation and Characterization of Crystalline Tacedinaline Form B

A mixture of 204.0 mg of crystalline tacedinaline, which is a mixture of Forms B and D, and 15 mL of a 2:1 (volume:volume) solution of THF:ethanol was brought to gentle reflux. Most of the solid dissolved. The mixture was filtered hot through hardened filter paper and the filter cake was retained. The clear filtrate was reheated to gentle reflux and reduced in volume by boiling. Crystallization occurred at a volume of about 8 mL. When the volume was about 5 mL, the mixture was removed from the hot plate and allowed to cool to ambient temperature. It was then covered and placed in the refrigerator overnight. Filtration and drying of the filter cake (ambient temperature, diaphragm pump pressure, 90 minutes) gave 121.6 mg of crystalline solid.

Analytical data were obtained on the product: the XRPD pattern was substantially as shown in FIG. 7B, and the DSC trace was substantially as shown in FIG. 10.

The analytical data obtained on the product indicate that it is crystalline tacedinaline Form B.

Example 6

Preparation and Characterization of Crystalline Tacedinaline Form B

A mixture of 74.5 mg of the mixture of crystalline tacedinaline Form B and Form D (1.6) from Example 1 and 8 mL of acetone was heated to gentle reflux on a hot plate. After about 20 minutes, all solids had dissolved. The solution was filtered through a glass wool plug and again heated to gentle reflux on a hot plate in order to concentrate it. When the volume was about 6 mL the sample was removed from the hot plate and was observed to become cloudy as it cooled. The mixture was warmed again until it was clear, removed from the hot plate, seeded with a small amount of crystalline tacedinaline Form B, and placed in the refrigerator overnight. Vacuum filtration and drying of the filter cake under diaphragm pump pressure for about 15 minutes afforded 28.7 mg of crystalline product.

Analytical data were obtained on the product: the XRPD pattern was as shown in FIG. 7A, the IR spectrum was substantially as shown in FIG. 8, the TGA profile was substantially as shown in FIG. 9, and the DSC trace was substantially as shown in FIG. 10.

The analytical data obtained on the product indicate that it is crystalline tacedinaline Form B.

Example 7

Preparation and Characterization of Crystalline Tacedinaline Form C

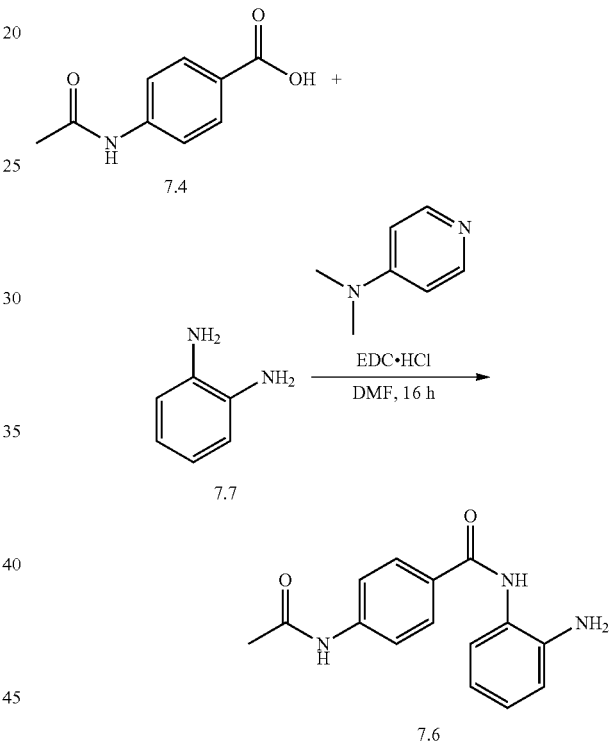

To the extent possible, the procedure set forth in Thomas, M. et al., *Bioorganic & Medicinal Chemistry* 2008, 16, 8109-8116, was followed as described herein. To a stirred solution of 4-acetamido benzoic acid 7.4 (2.5 g, 13.95 mmol, 1.0 eq.) in N,N-dimethylformamide (50 mL) was added o-phenyldiamine 7.7 (4.53 g, 41.9 mmol, 3.0 eq.), followed by N-(3-dimethylaminopropyl)-N'-ethylcarbodiimide hydrochloride (3.48 g, 18.14 mmol, 1.3 eq.) and catalytic 4-(dimethylamino)pyridine (0.18 g, 1.47 mmol, 0.1 eq.). The reaction mixture was stirred at room temperature for 16 hours. The solvents were removed under reduced pressure at 58° C. The crude residue was diluted with dichloromethane (100 mL) and kept in the refrigerator overnight. The resulting precipitate was filtered, washed with hot dichloromethane (100 mL), and dried under vacuum to afford 4-acetamido-N-(2-aminophenyl)benzamide 7.6 as an off-white solid. Yield 7.6=2.48 g (66%).

XRPD data was obtained and the crude product was determined to be a mixture of Forms B and D. The visual melting point was obtained and was about 236° C., although it is noted that the procedure in the above mentioned paper reports a melting point of about 216° C.

In a manner similar to that described in WO 2009/076234, paragraph [64], the crude product 7.6 (0.5 g) was dissolved in 50 mL of hot (70° C.) MeOH:THF (1:1 v/v). The solution was stored at room temperature for 24 hours. The resulting white crystals were filtered to provide 0.27 g of crystalline product.

Figure 19:
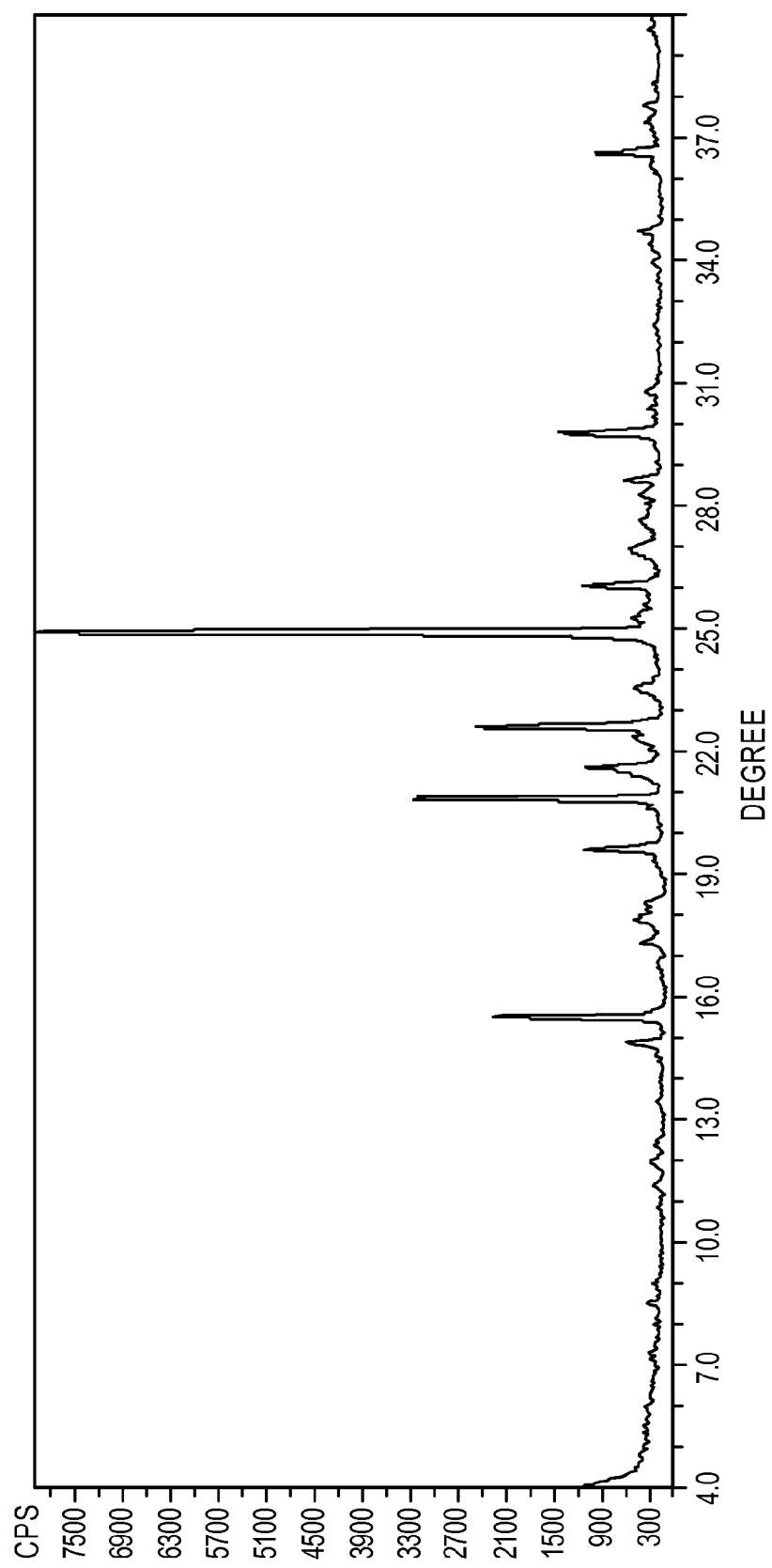
FIG. 19 is an XRPD pattern of crystalline tacedinaline Form C.
Figure 20:
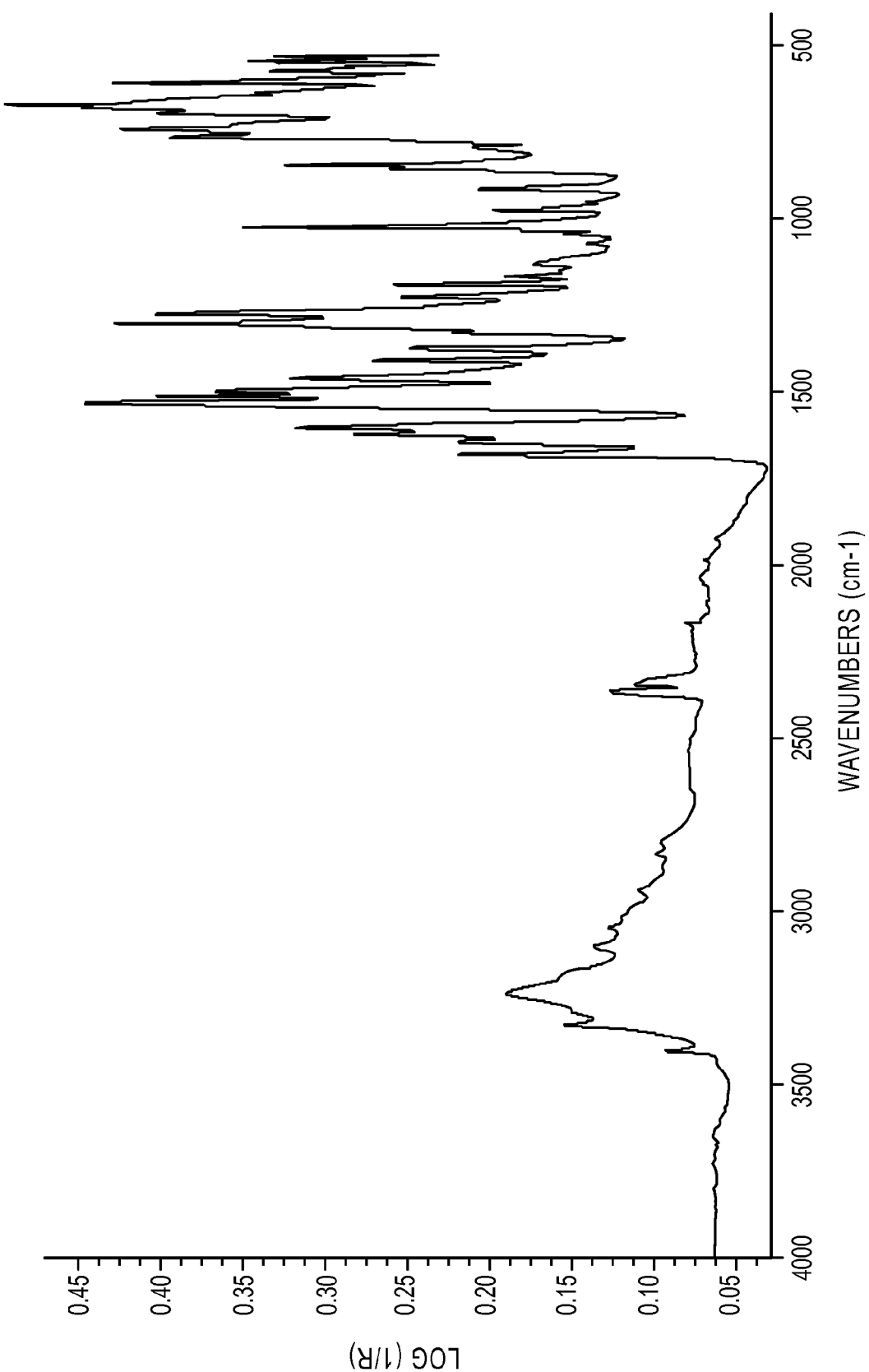
FIG. 20 is an IR spectrum of crystalline tacedinaline Form C.
Figure 21:
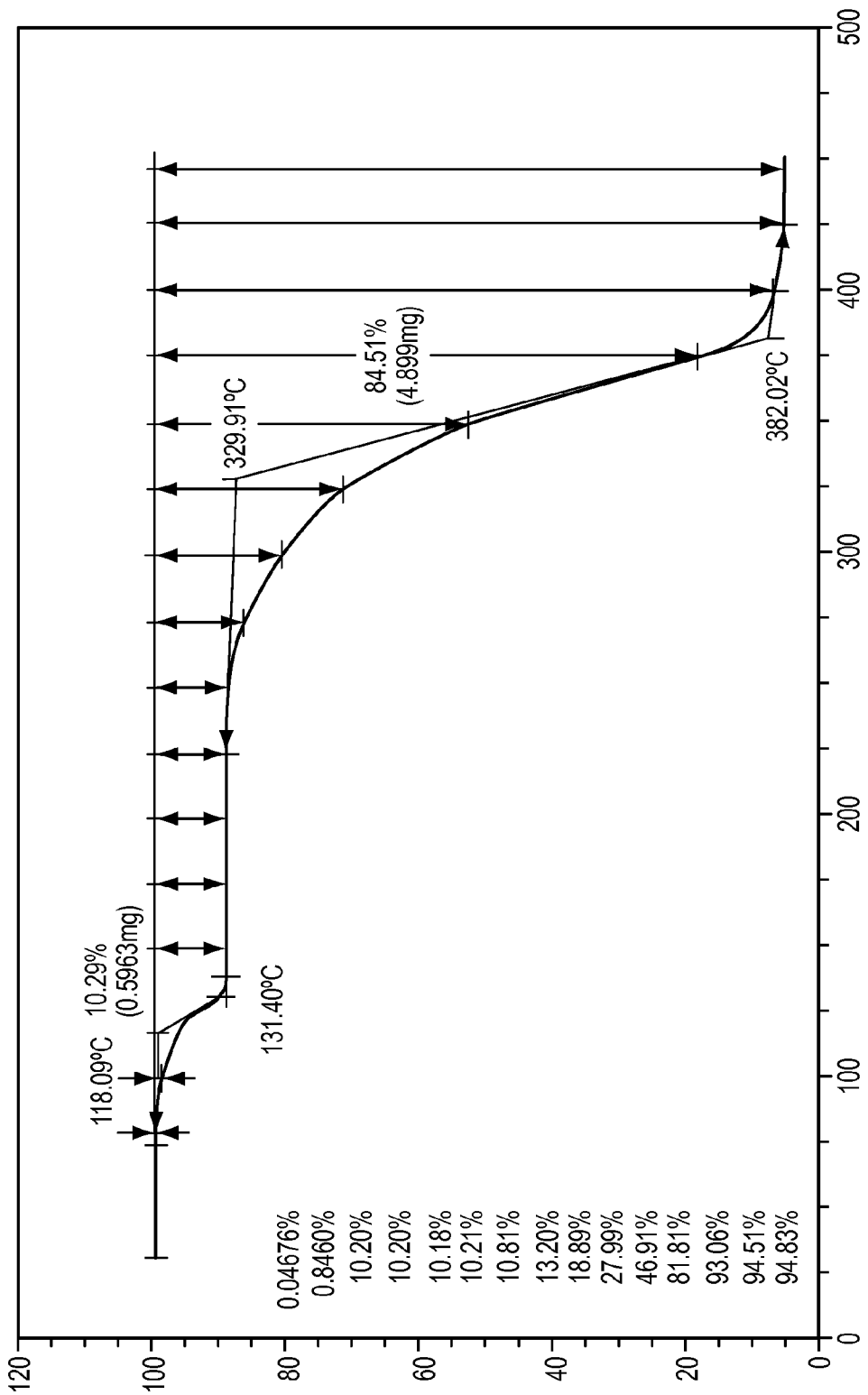
FIG. 21 is a TGA profile of crystalline tacedinaline Form C.
Figure 22:
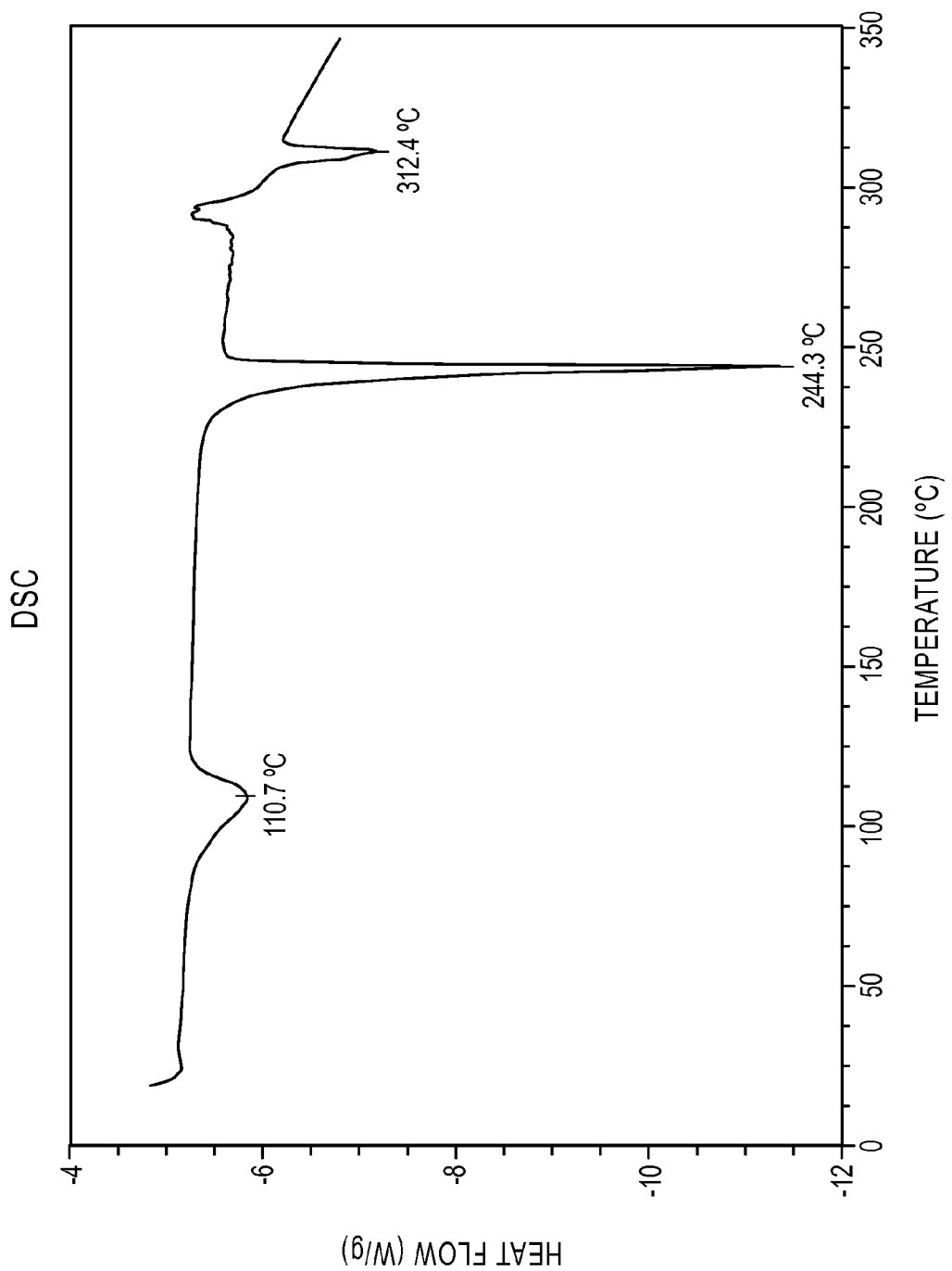
FIG. 22 is a DSC thermogram of crystalline tacedinaline Form C.
Figure 23A:
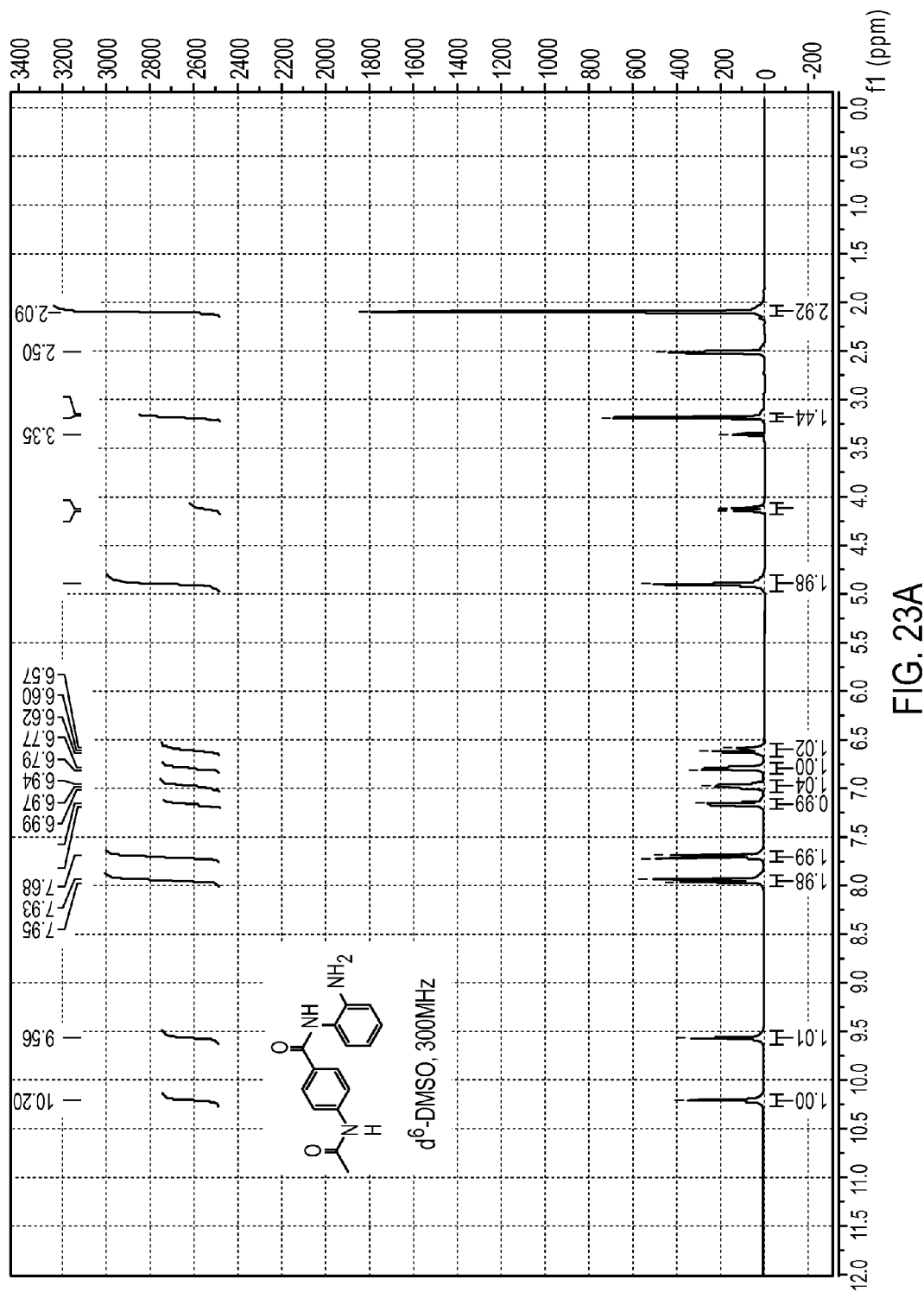
FIGS. 23A-23C are $^1$H-NMR spectra of crystalline tacedinaline Form C.
Figure 23B:
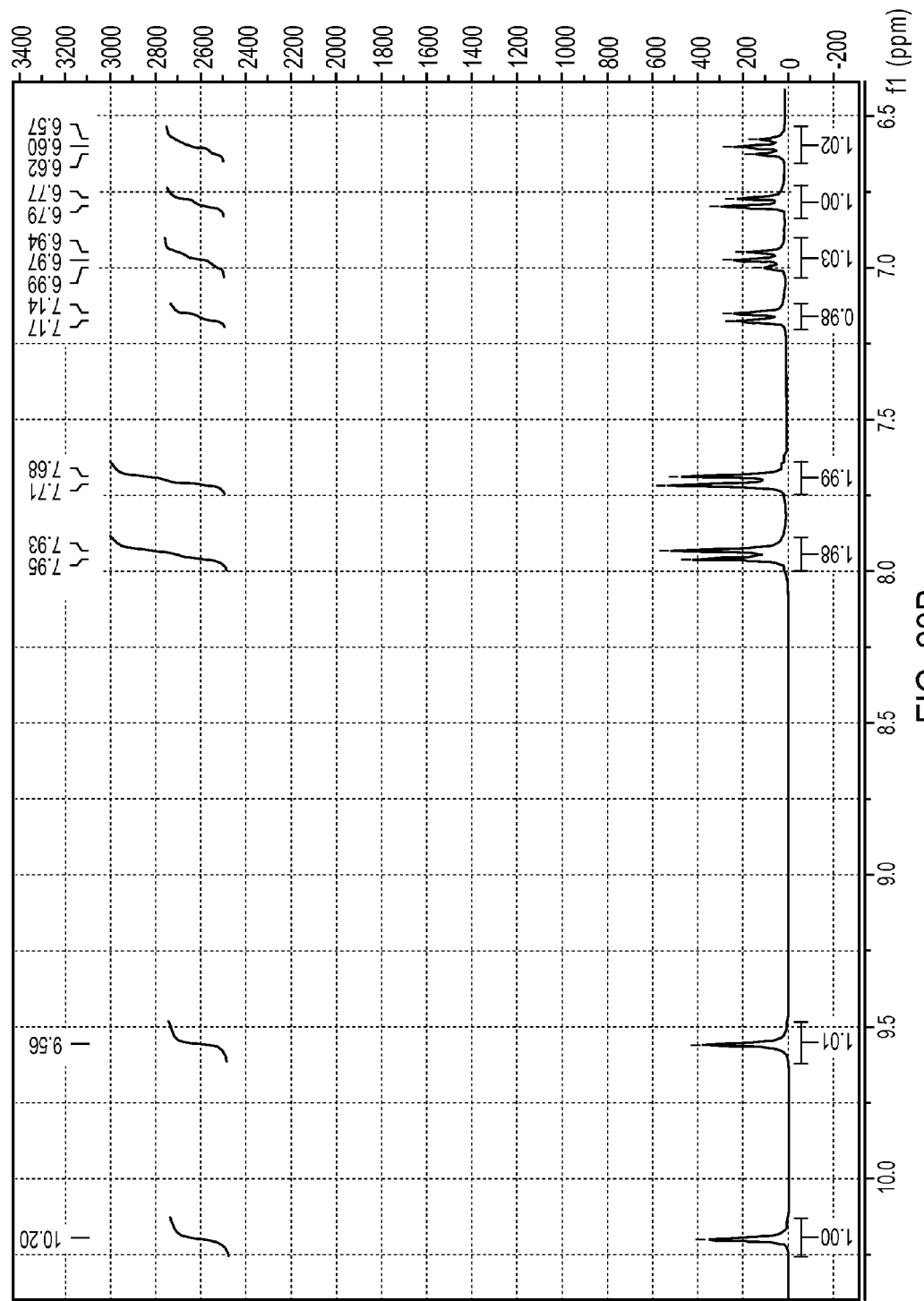
Figure 23C:
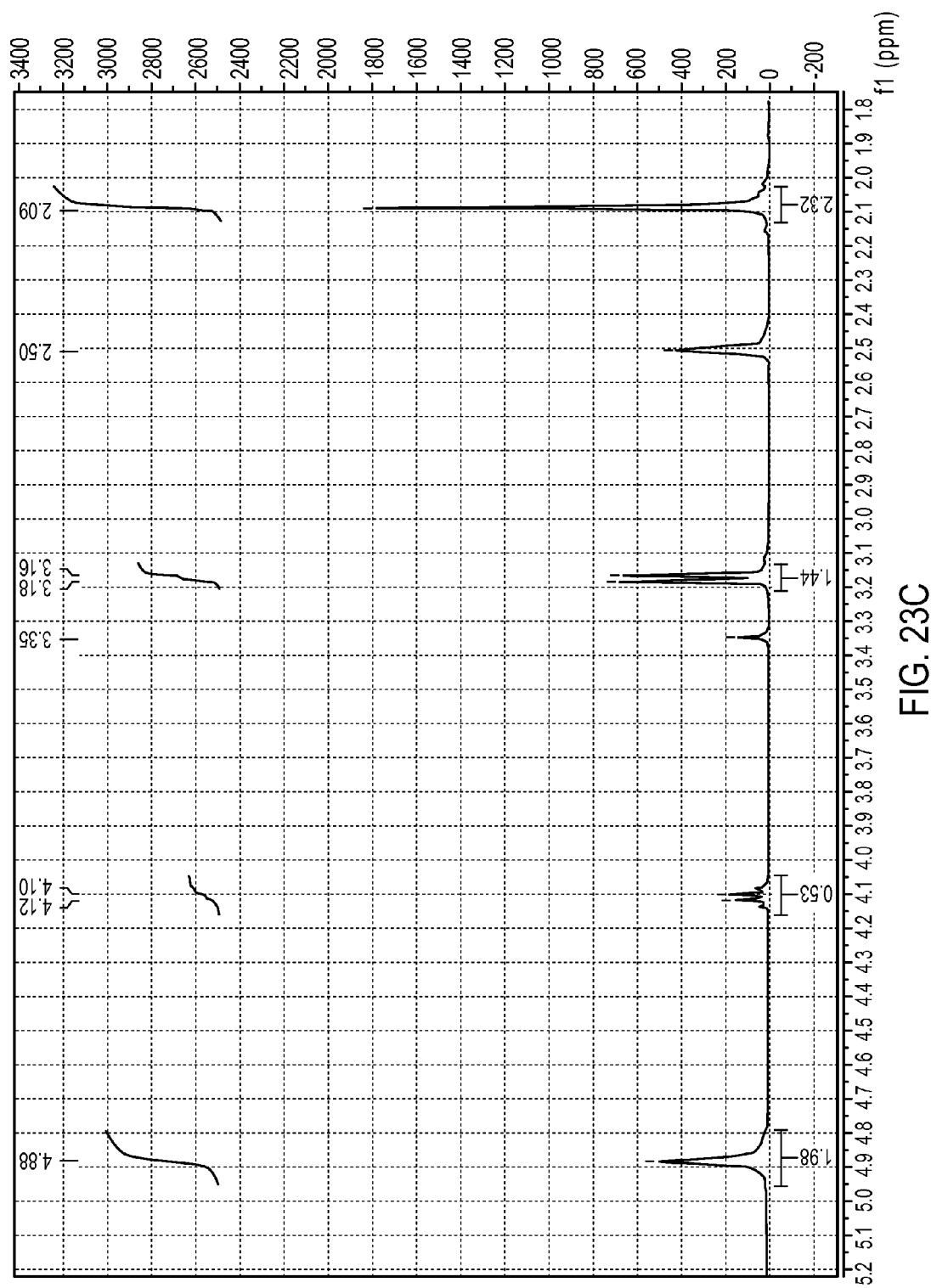
Figure 24A:
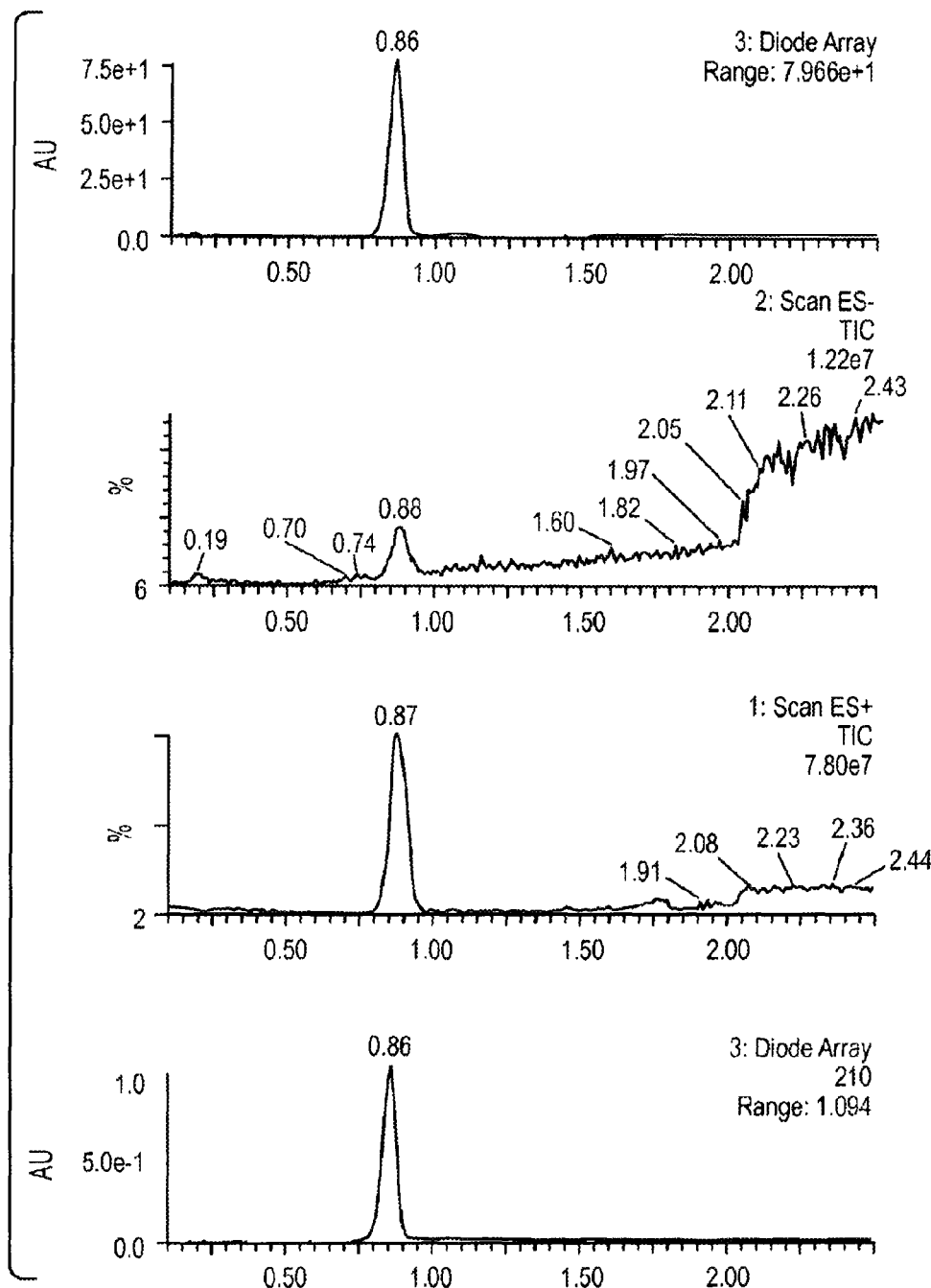
FIGS. 24A-24B are LC/MS data for crystalline tacedinaline Form C.
Figure 24B:
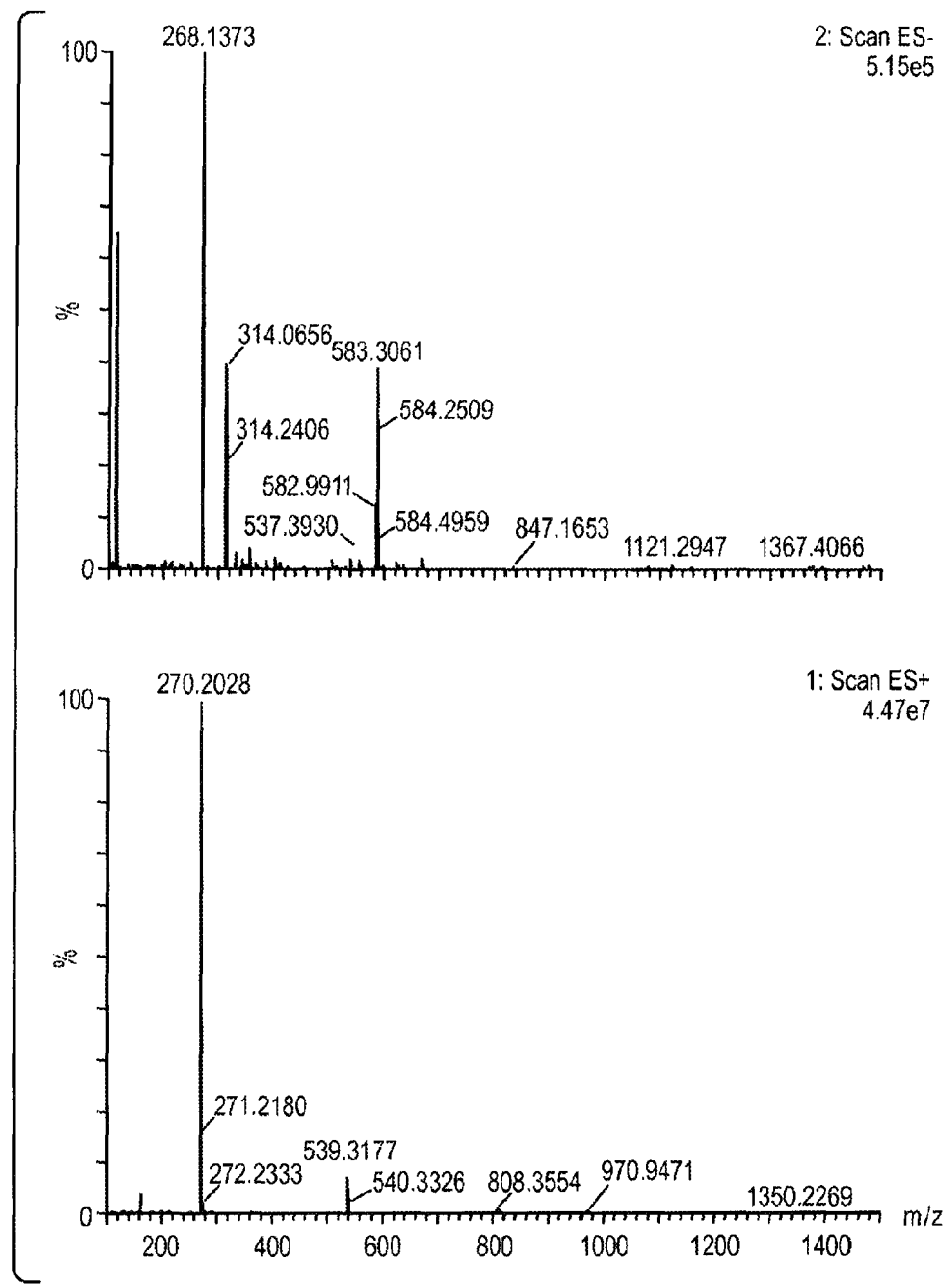

Analytical data were obtained on the product: the XRPD pattern was as shown in FIG. 19, the IR spectrum was as shown in FIG. 20, the TGA profile was as shown in FIG. 21, the DSC trace was as shown in FIG. 22, the $^1$H-NMR spectrum was as shown in FIGS. 23A-23C, and the LC/MS data was as shown in FIG. 24.

The analytical data obtained on the product indicate that it is crystalline tacedinaline Form C, a methanol solvate.

Example 8

Single Crystal X-ray Analysis of Crystalline Tacedinaline Form C

A single crystal of tacedinaline Form C suitable for x-ray diffraction analysis was analyzed. The crystallographic data collection and single crystal parameters for the tacedinaline Form C crystal are set forth in Table 10.

TABLE 10

| formula | $C_{16}H_{19}N_3O_3$ |
|---|---|
| formula weight | 301.35 |
| space group | P 1 21/c 1 (No. 14) |
| a (Å) | 9.7236(5) |
| b (Å) | 7.4334(5) |
| c (Å) | 20.5398(10) |
| β (degrees) | 90.133(4) |
| volume (Å$^3$) | 1484.60(14) |
| Z | 4 |
| d$_{calc}$ (g cm$^{-3}$) | 1.348 |
| crystal dimensions (mm) | 0.25 × 0.20 × 0.20 |
| temperature (K) | 150 |
| radiation (wavelength in Å) | Cu Kα (1.54184) |
| monochromator | graphite |
| linear abs coef (mm−1) | 0.737 |
| absorption correction applied | empirical$^a$ |
| transmission factors (min, max) | 0.76, 0.86 |
| diffractometer | Nonius Kappa CCD |
| h, k, l range | −11 to 11 −8 to 0 −22 to 24 |
| 2θ range (deg) | 4.30-144.17 |
| mosaicity (deg) | 0.79 |
| programs used | SHELXTL |
| F$_{000}$ | 640.0 |
| weighting | 1/[σ$^2$(Fo$^2$) + (0.0695P)$^2$ + 0.7118P] where P = (Fo$^2$ + 2Fc$^2$)/3 |
| data collected | 6351 |
| unique data | 2551 |
| R$_{int}$ | 0.051 |
| data used in refinement | 2551 |
| cutoff used in R-factor calculations | F$_o^2$ > 2.0s(F$_o^2$) |
| data with I > 2.0s(I) | 2461 |
| number of variables | 221 |
| largest shift/esd in final cycle | 0.00 |
| R(F$_o$) | 0.050 |
| Rw(F$_o^2$) | 0.133 |
| goodness of fit | 1.079 |

$^a$Otwinowski, Z.; Minor, W. *Methods Enzymol.* 1997, 276, 307

Example 9

Preparation and Characterization of a Mixture of Crystalline Tacedinaline Forms B and D A sample of 506.9 mg of the mixture of crystalline tacedinaline Form B and Form D (1.6) from Example 1 was placed in a vial and treated drop wise with DMF, with warming on a hot plate, until a solution resulted. About 1.5 mL of DMF were required. The solution was added to 10 mL of cooled dichloromethane. The resulting slurry was placed in the freezer for about 10 minutes and vacuum filtered. The filter cake was placed in a dessicator under diaphragm pump pressure for about 30 minutes to give 424.7 mg (84% yield) of crystalline product.

Figure 17A:
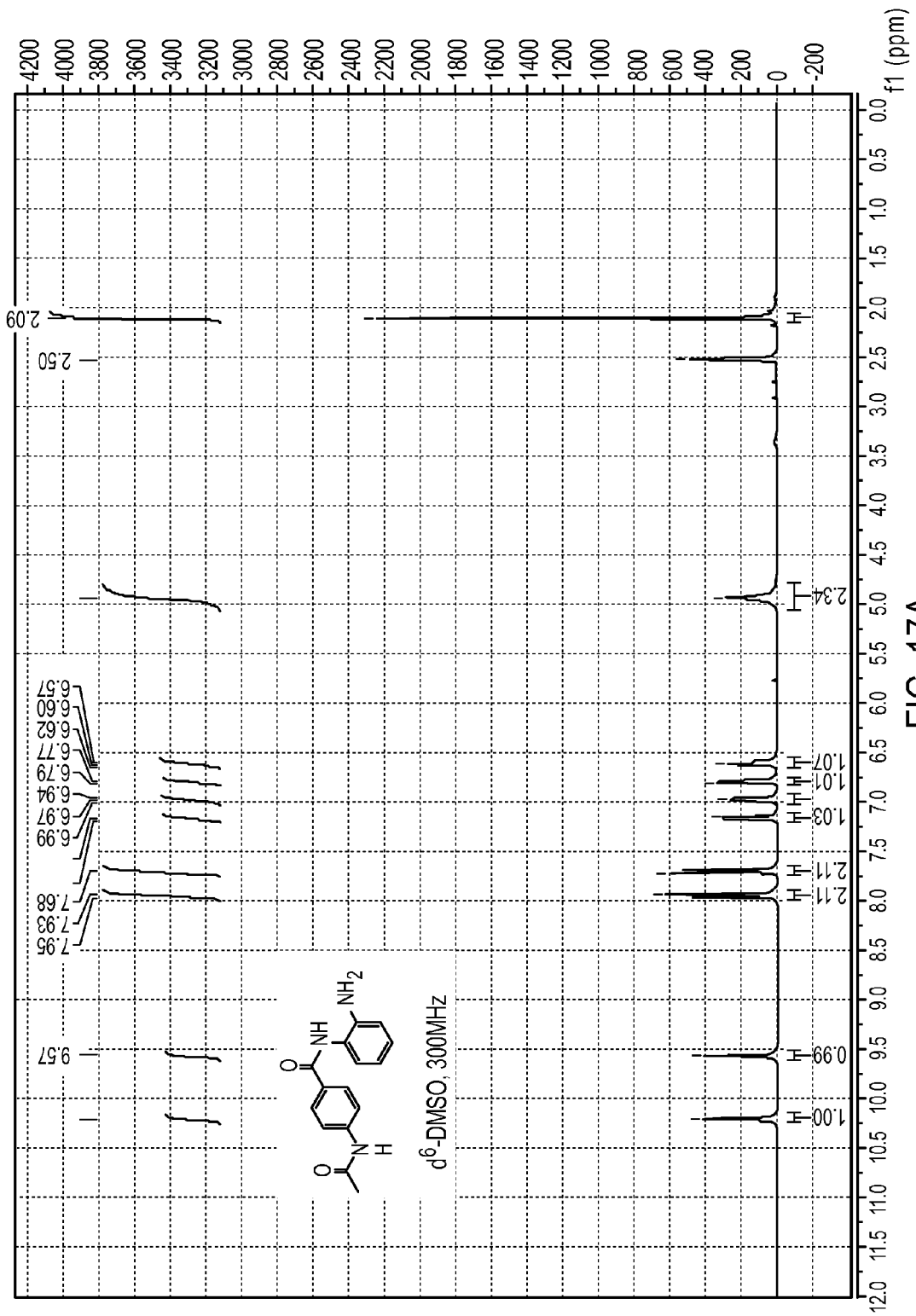
FIGS. 17A-17C show exemplary $^1$H-NMR spectra of an embodiment of a mixture of crystalline tacedinaline Forms B and D.
Figure 17B:
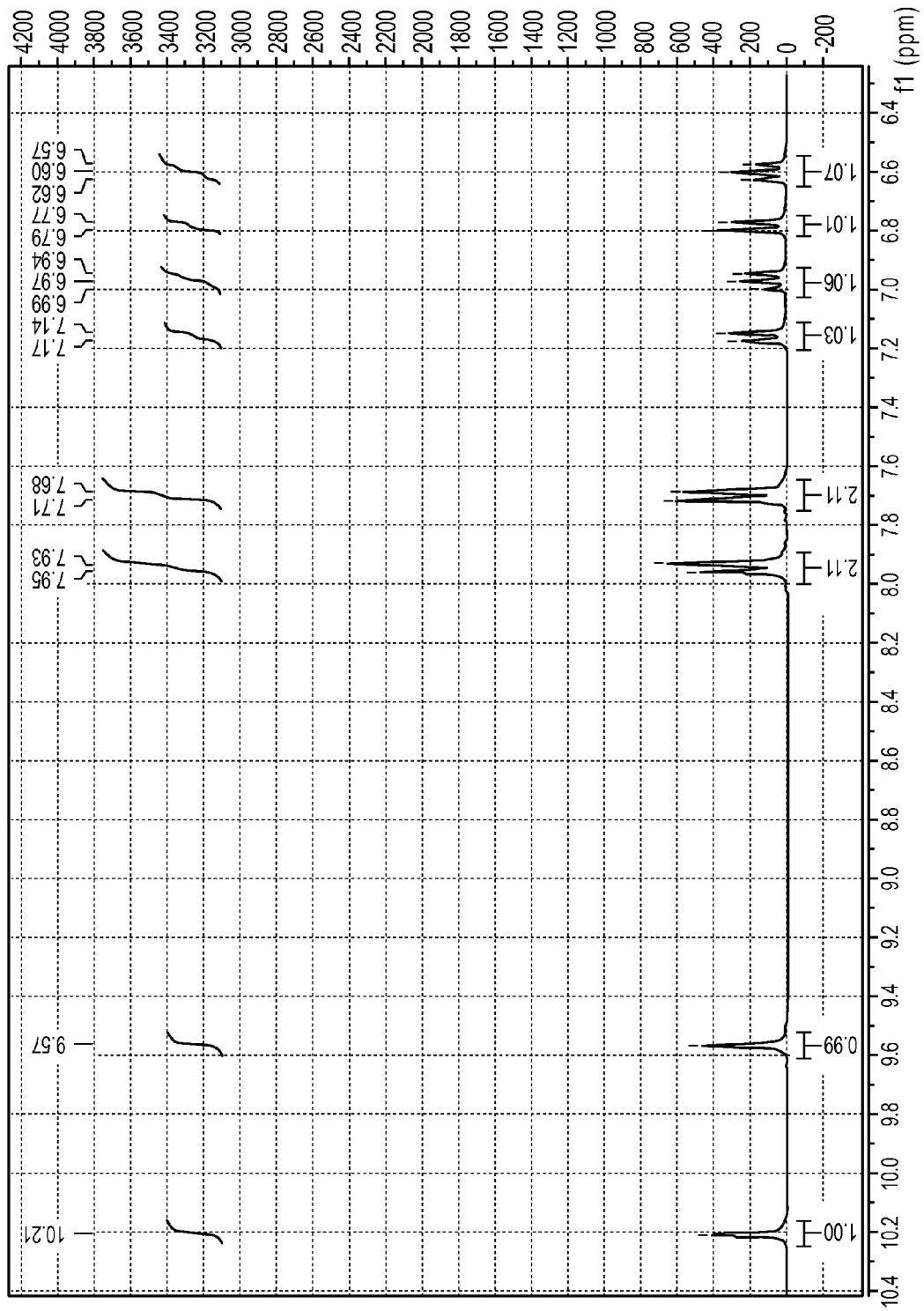
Figure 17C:
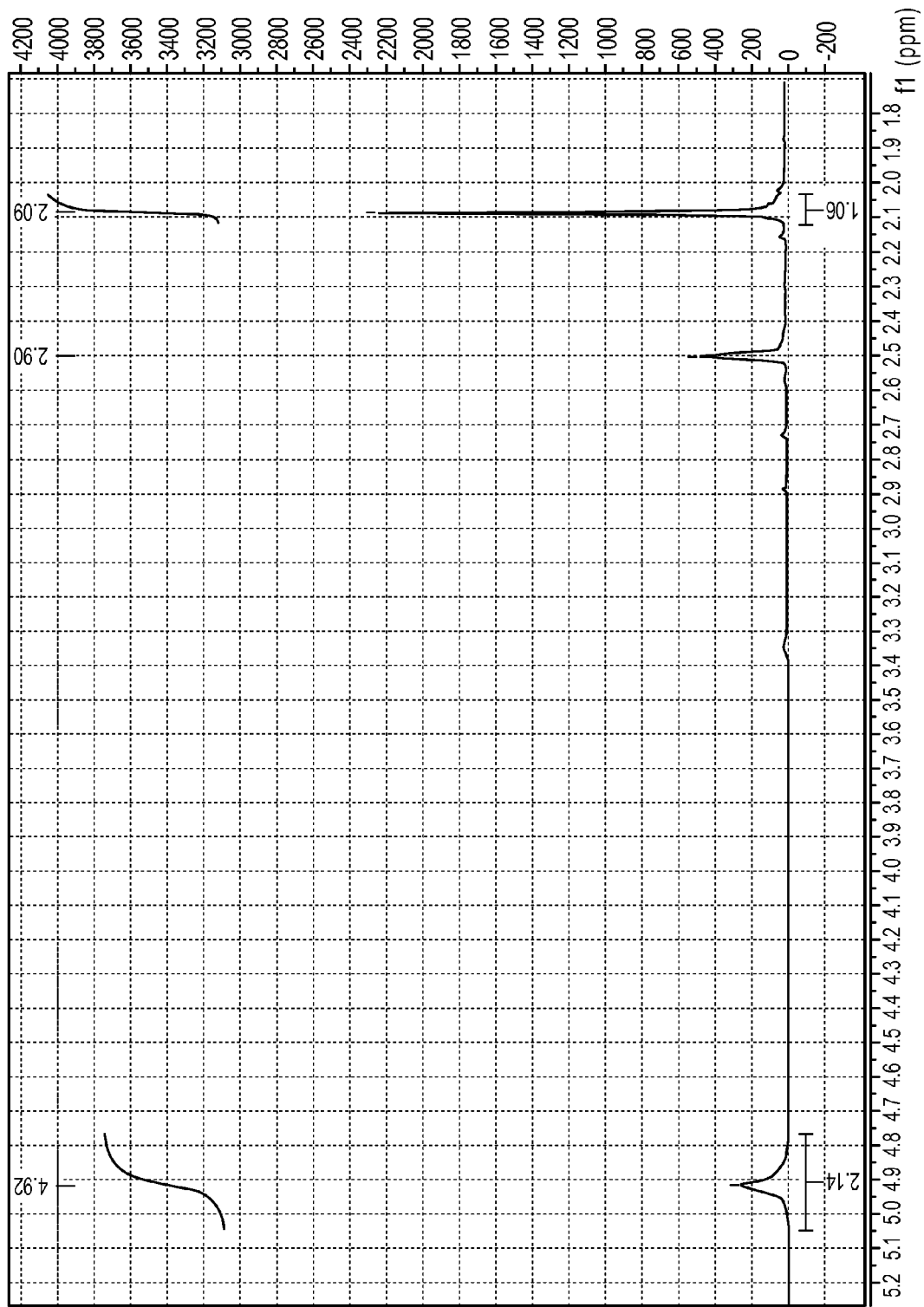
Figure 18A:
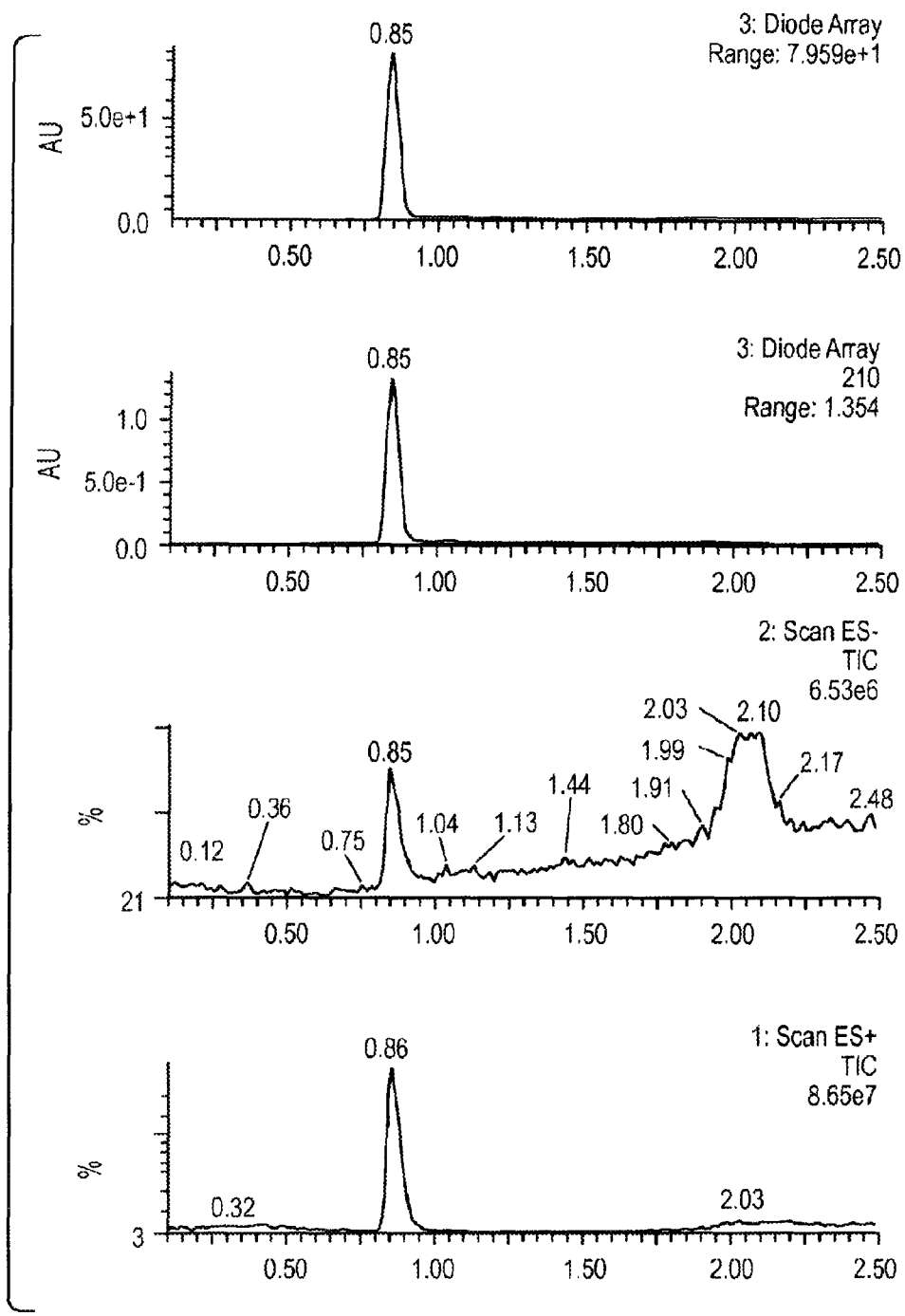
FIGS. 18A-18B show exemplary LC/MS data for an embodiment of a mixture of crystalline tacedinaline Forms B and D.
Figure 18B:
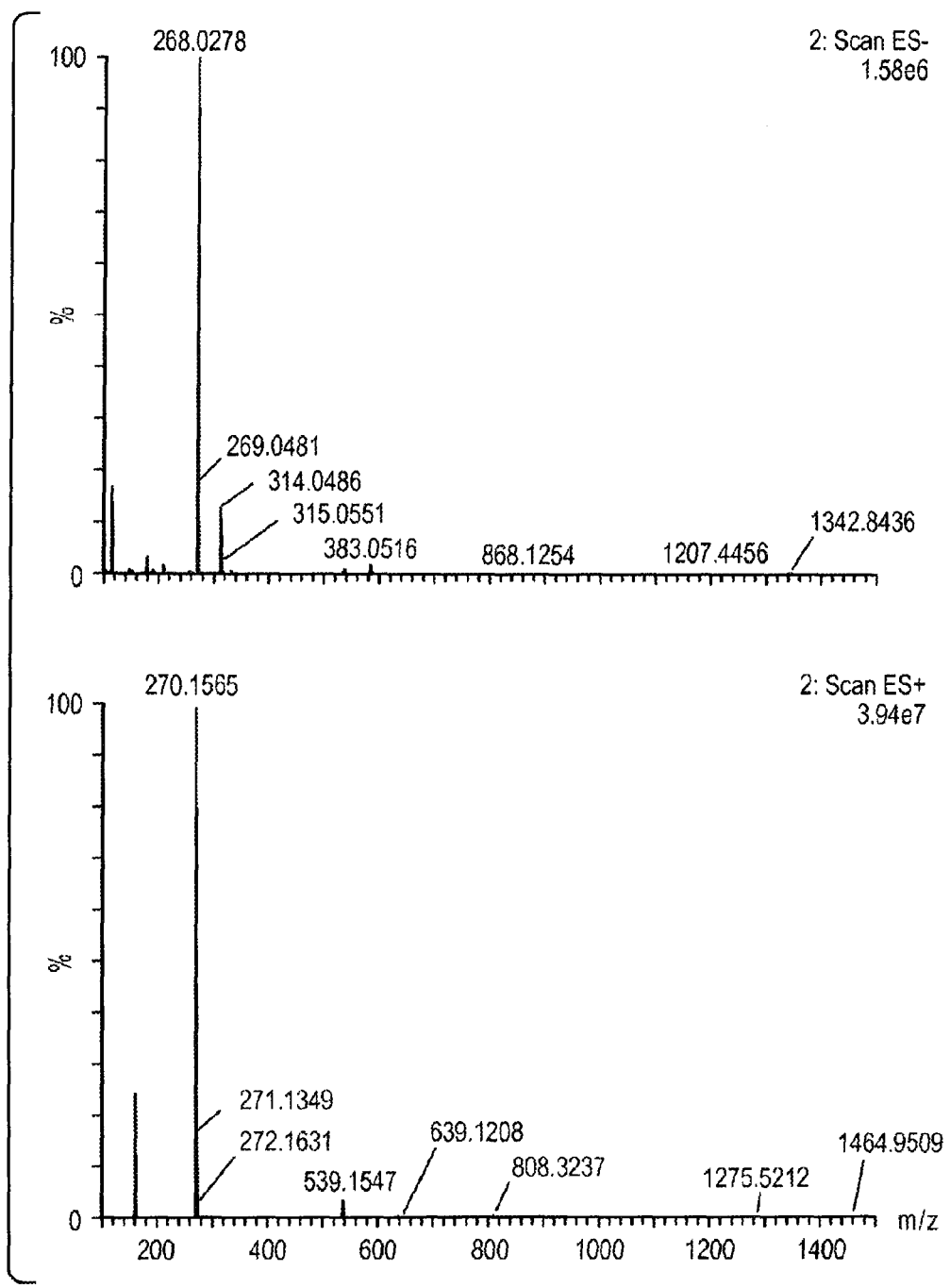

Analytical data were obtained on the product: the XRPD pattern was substantially as shown in FIG. 13, the IR spectrum was as shown in FIG. 14, the TGA profile was as shown in FIG. 15, the DSC trace was as shown in FIG. 16, the $^1$H-NMR spectrum was as shown in FIGS. 17A-17C, and the LC/MS data was as shown in FIG. 18.

The analytical data obtained on the product indicate that it is a mixture of crystalline tacedinaline Forms B and D.

Example 10A

Preparation and Characterization of Crystalline Tacedinaline Form D

To a mixture of 161.3 mg of crystalline tacedinaline Forms B and D, was added 2 mL of acetone. The resulting slurry was stirred at ambient temperature for 7 days and filtered to give white solid.

Figure 28:
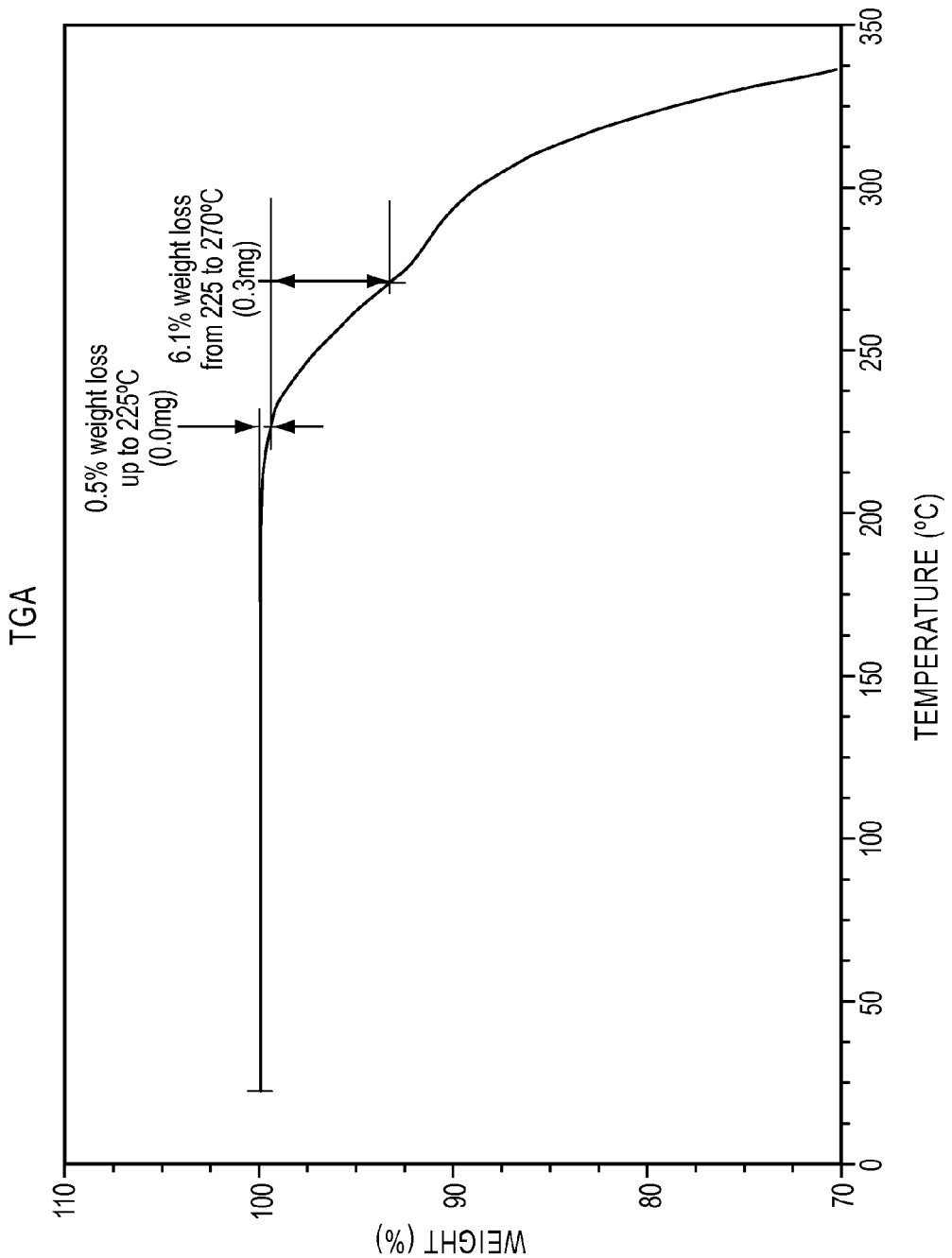
FIG. 28 shows an exemplary TGA profile of an embodiment of crystalline tacedinaline Form D.
Figure 29:
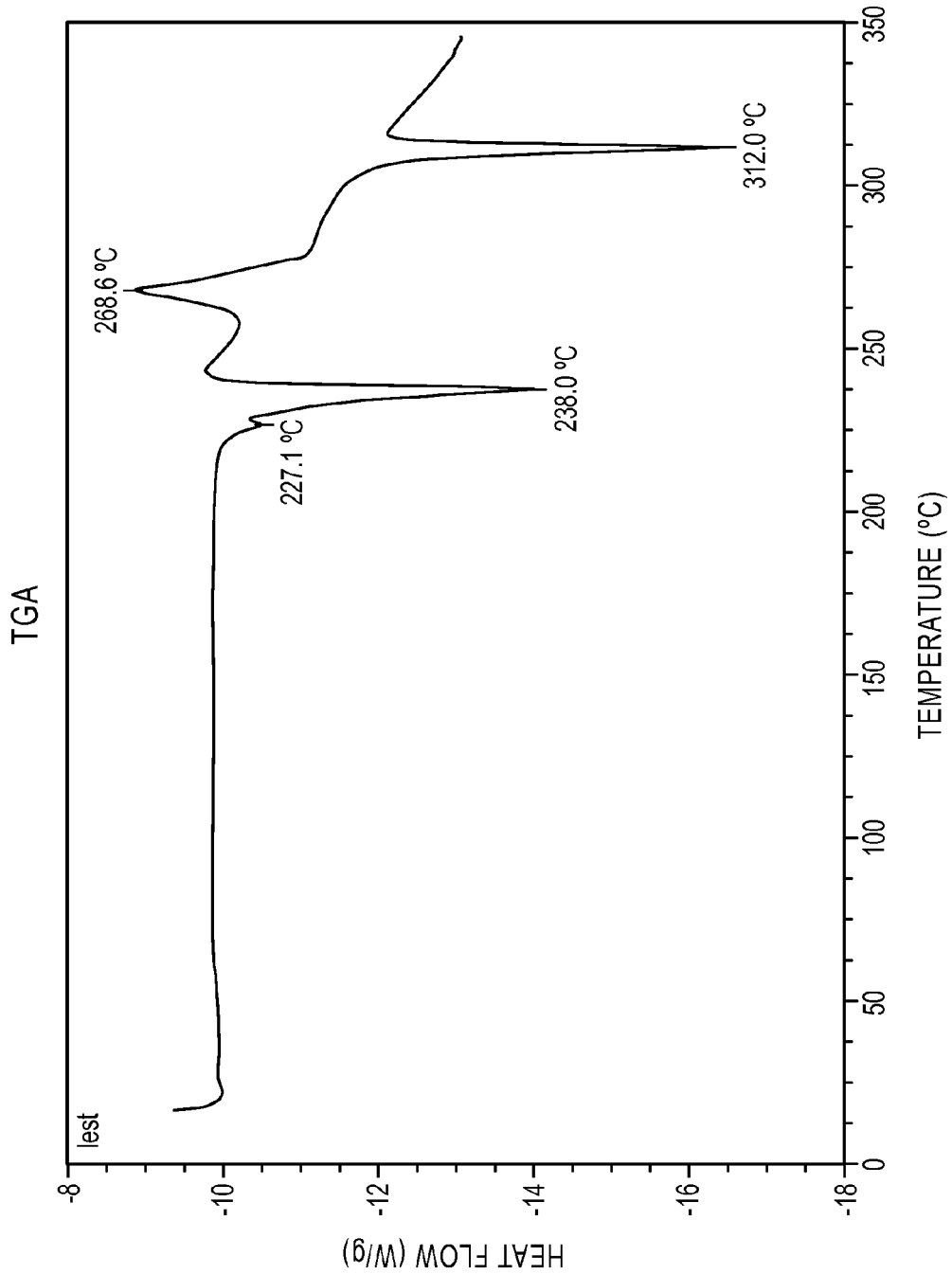
FIG. 29 shows an exemplary DSC thermogram of an embodiment of crystalline tacedinaline Form D.

Analytical data were obtained on the product: the XRPD pattern was as shown in FIG. 26, the IR spectrum was as shown in FIG. 27, the TGA profile was as shown in FIG. 28, the DSC trace was as shown in FIG. 29, the $^1$H-NMR spectrum was as shown in FIGS. 39A-39C, and the LC/MS data was as shown in FIGS. 40A-40C.

The analytical data obtained on the product indicate that it is crystalline tacedinaline Form D.

Example 10B

Single Crystal X-Ray Analysis of Crystalline Tacedinaline Form D

A slurry of 113.6 mg of a mixture of crystalline tacedinaline Forms B and D was mixed in about 2 mL of a 1:1 (v:v) mixture of acetone:water and heated on a hot plate with stirring until it refluxed gently. Additional portions of a 1:1 (v:v) mixture of acetone:water were added until all the solid dissolved. About 8 mL total were required. The solution was filtered through a glass wool plug and the filtrate was allowed to stand at ambient temperature in a closed vial overnight, during which time crystallization occurred. The mixture was vacuum filtered and the crystals were dried under diaphragm pump pressure for about 15 minutes.

A single crystal of tacedinaline Form D suitable for x-ray diffraction analysis was selected and analyzed. The crystallographic data collection and single crystal parameters for the tacedinaline Form D crystal are set forth in Table 11.

TABLE 11

| formula | $C_{15}H_{15}N_3O_2$ |
|---|---|
| formula weight | 269.31 |
| space group | P-1 (No. 2) |
| a (Å) | 7.2687(5) |
| b (Å) | 12.6881(9) |
| c (Å) | 15.5597(14) |
| α (degrees) | 105.784(6) |
| β (degrees) | 100.001(6) |
| γ (degrees) | 97.274(5) |
| volume (Å³) | 1336.84(18) |
| Z | 4 |
| $d_{calc}$ (g cm$^{-3}$) | 1.338 |
| crystal dimensions (mm) | 0.24 × 0.12 × 0.04 |
| temperature (K) | 150 |
| radiation (wavelength in Å) | Cu Kα (1.54184) |
| monochromator | graphite |
| linear abs coef (mm−1) | 0.705 |
| absorption correction applied | empirical[a] |
| transmission factors (min, max) | 0.83, 0.97 |
| diffractometer | Nonius Kappa CCD |
| h, k, l range | 0 to 8, −15 to 15, −18 to 18 |
| 2θ range (deg) | 6.05-140.29 |
| mosaicity (deg) | 0.41 |
| programs used | SHELXTL |
| $F_{000}$ | 568.0 |
| weighting | $1/[\sigma^2(F_o^2) + (0.0610P)^2 + 0.5417P]$ where $P = (F_o^2 + 2F_c^2)/3$ |
| data collected | 19661 |
| unique data | 4158 |
| $R_{int}$ | 0.032 |
| data used in refinement | 4158 |
| cutoff used in R-factor calculations | $F_o^2 > 2.0s(F_o^2)$ |
| data with I > 2.0s(I) | 3411 |
| number of variables | 395 |
| largest shift/esd in final cycle | 0.00 |
| R($F_o$) | 0.043 |
| Rw($F_o^2$) | 0.111 |
| goodness of fit | 1.056 |

[a]Otwinowski, Z.; Minor, W. *Methods Enzymol.* 1997, 276, 307

Example 11

Competitive Slurry Experiment

A slurry containing 25.8 mg tacedinaline Form A, 25.8 mg of a mixture of tacedinaline Forms B and D, a few milligrams of tacedinaline Form B, and 0.5 mL of tetrahydrofuran (THF) was stirred overnight and filtered to give 38.6 mg of a white solid. The white solid was analyzed by XRPD and determined to be tacedinaline Form A.

The result of this experiment suggest that crystalline tacedinaline Form A is more thermodynamically stable, relative to tacedinaline Forms B, and D.

Example 12

Solubility Study

Analysis of the relative solubilities of crystalline tacedinaline Forms A, B, and D was performed as follows.

A calibration curve was prepared using 5 samples (samples 02-06) of various concentrations in water, as set forth in Table 12. The starting material was Form B. The only peak in the spectrum, at approximately 267 nm, was used. The UV parameters were: scan range: 190-800 nm; 480 nm/min; 1 cm cuvette.

TABLE 12

| Sample | Concentration (mg/mL) | UV absorbance value | Peak (nm) |
|---|---|---|---|
| 02 | 0.0196 | 1.44 | 267.83 |
| 03 | 0.01568 | 1.16 | 267.71 |
| 04 | 0.01176 | 0.87 | 267.67 |
| 05 | 0.00588 | 0.54 | 267.23 |
| 06 | 0.00196 | 0.19 | 267.74 |

Figure 43:
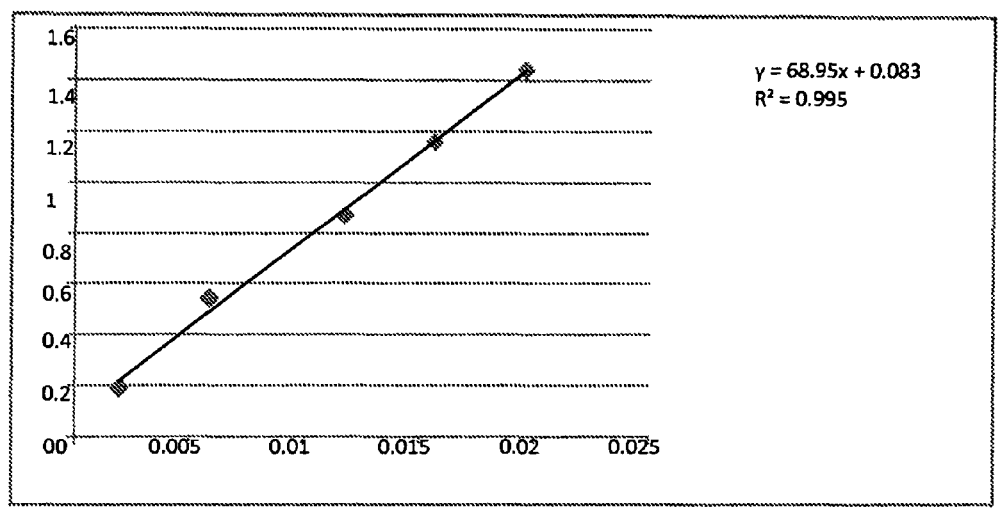
FIG. 43 shows a graphic representation of the data of Table 12.

A graphic representation of the data of Table 12 is in FIG. 43.

Each sample was placed in water to give a slurry. The slurries were stirred at ambient temperature for 24 hours. The temperature in the laboratory was monitored and found to be steady at 23° C. After 24 hours, the vials containing the slurries were centrifuged for about 5 minutes. The mother liquors were decanted and filtered through 0.2 micron filters, then diluted appropriately and analyzed by UV. Solids were dried under dry air purges and analyzed by XRPD. The results are set forth below in Table 13.

TABLE 13

| Starting Form | Ending Form | Solubility (mg/mL) |
|---|---|---|
| A | A | 0.0176 |
| B | B | 0.0426 |
| B + D | D | 0.0208 |

The results of Examples 10A, 11, and 12 show that relative thermodynamic stability of crystalline tacedinaline Forms A, B, and D is as follows: A>D>B.

Example 13

Accelerated Stability Studies

Accelerated stability studies were performed on samples of crystalline tacedinaline Forms A, B, C, and a mixture of Forms B and D, under conditions of 40° C. and 75% relative humidity. For the studies on Form A, samples were taken at 8 days, 15 days, one month, 10 weeks, and 8 months. For the studies on Forms B, C, and a mixture of Forms B and D, samples were taken at 2, 4, 6, 8, and 10 weeks.

The results of the studies on Forms B, C, and a mixture of Forms B and D, which are set forth below in Table 14, show that, at least under these conditions, crystalline tacedinaline Form B is more stable than Form C, as Form C converted to either Form D, or a mixture of Form D with some amount of Form A present.

As can also be seen from the results in Table 14, the mixture of Form B and Form D is also more stable than Form C under these conditions.

TABLE 14

| Starting Material | Pull Time | XRPD Result |
|---|---|---|
| B | 2 weeks | B |
|  | 4 weeks | B |
|  | 6 weeks | B |
|  | 8 weeks | B |
| C | 2 weeks | D + A |
|  | 4 weeks | D |
|  | 6 weeks | D + A |
|  | 8 weeks | D + A |

TABLE 14-continued

| Starting Material | Pull Time | XRPD Result |
|---|---|---|
| B + D | 2 weeks | B + D |
|  | 4 weeks | B + D |
|  | 6 weeks | B + D |
|  | 8 weeks | B + D |

The results of the studies on Form A, which are set forth in Table 15 below, show that, at least under these conditions, crystalline tacedinaline Form A is stable, as no conversion was seen.

TABLE 15

| Starting Material | Pull Time | XRPD Result |
|---|---|---|
| A | 8 days | A |
|  | 15 days | A |
|  | 1 month | A |
|  | 10 weeks | A |
|  | 8 months | A |

Example 14

Preparation of Amorphous Tacedinaline

Into a platinum TG pan was added 16.7 mg Form A. The sample was heated in the TG furnace at 10° C./min up to 245° C. The sample was held at 245° C. for 2 minutes. Pan was removed from TG furnace and solid was scraped out. Solid appeared to be a clear glass. Sample was analyzed by XRPD and appears amorphous.

Figure 31A:
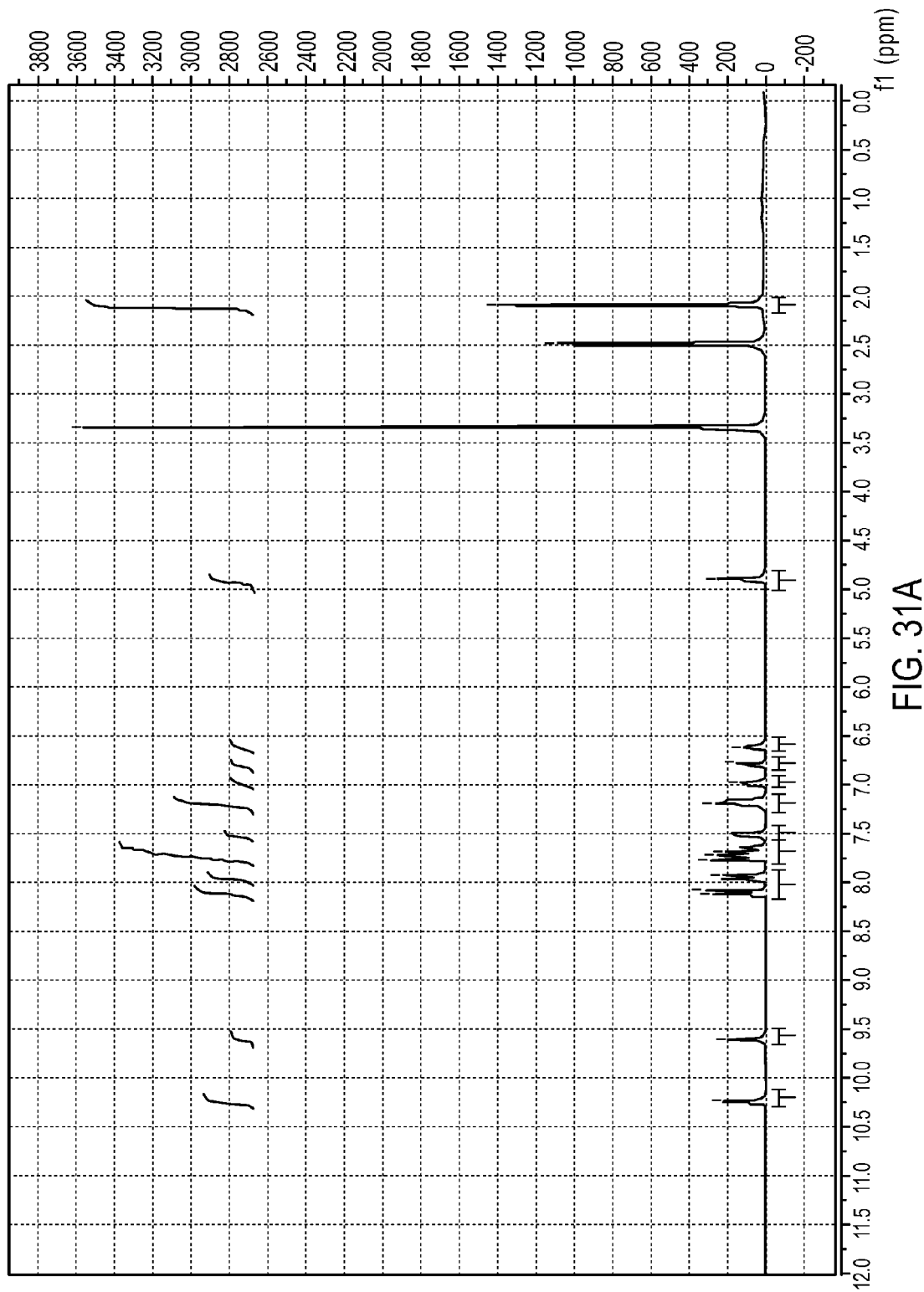
FIG. 31A shows an exemplary ¹H-NMR spectrum of an embodiment of a mixture of amorphous tacedinaline and N-(4-(1-H-benzo[d]imidazol-2-yl)acetamide, and FIG. 31B shows an ¹H-NMR spectrum of N-(4-(1-H-benzo[d]imidazol-2-yl)acetamide.
Figure 31B:
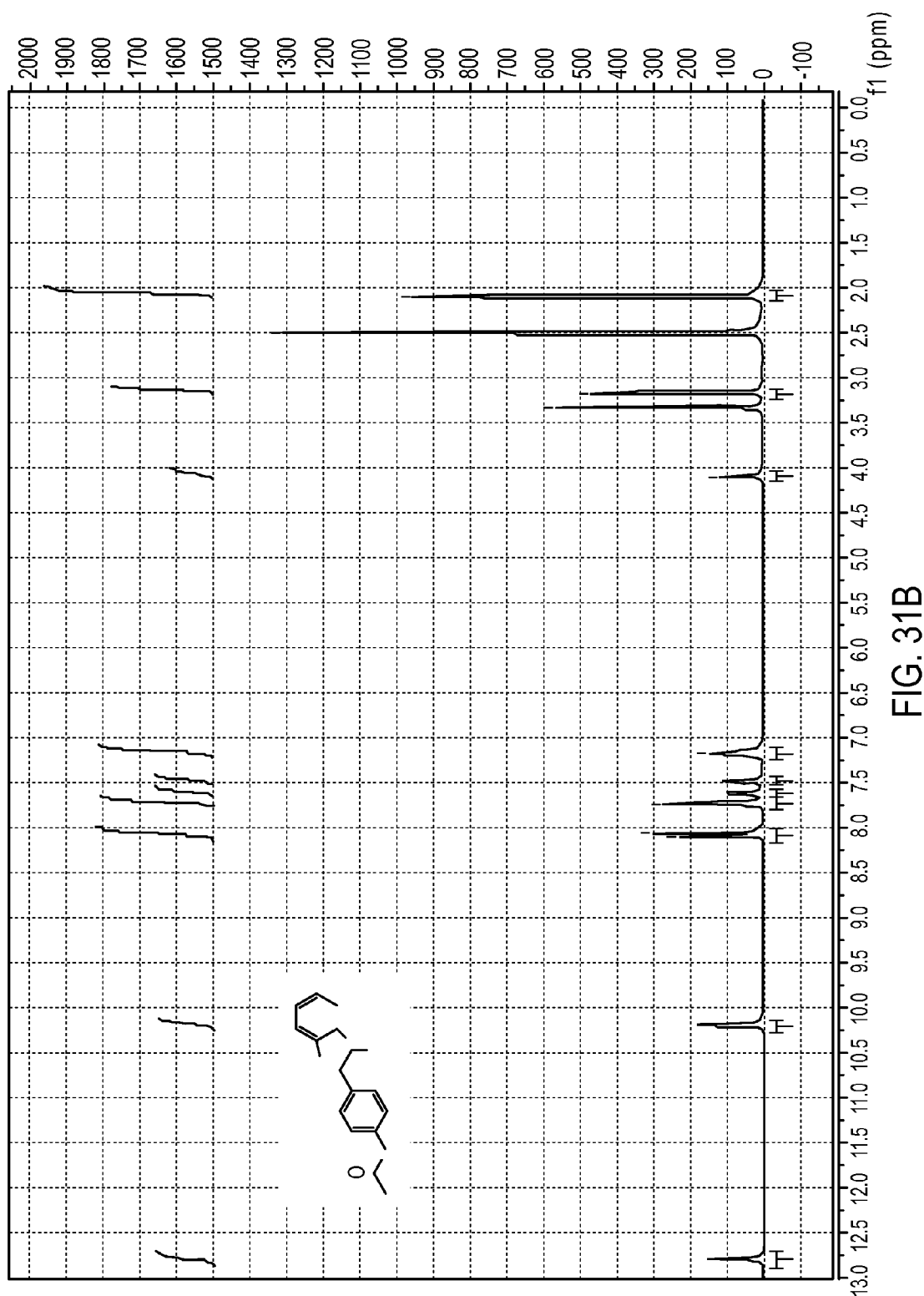
Figure 32A:
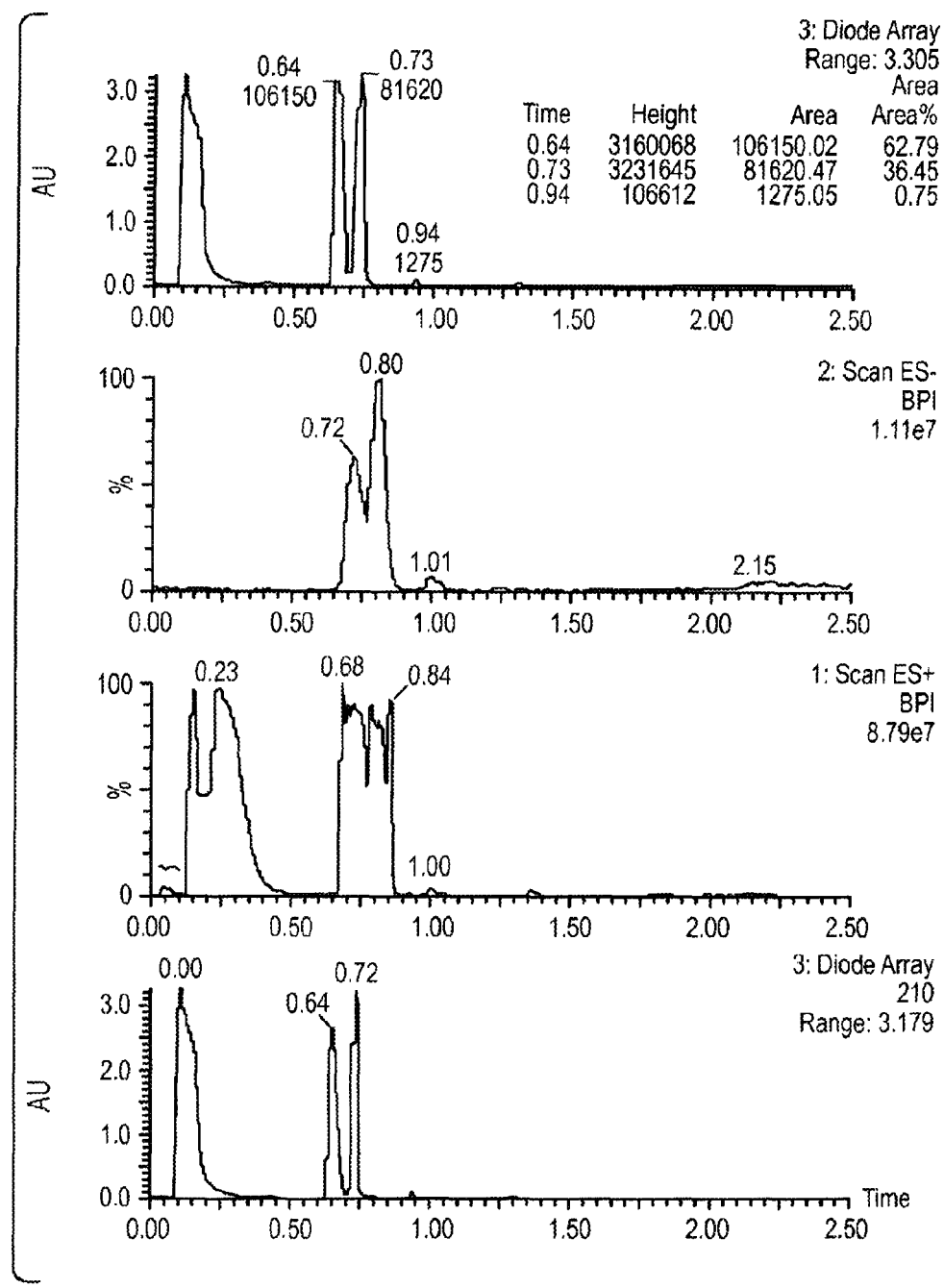
FIGS. 32A-32B show exemplary LC/MS data of an embodiment of a mixture of amorphous tacedinaline and N-(4-(1-H-benzo[d]imidazol-2-yl)acetamide, and FIGS. 32C-32D show LC/MS data for N-(4-(1-H-benzo[d]imidazol-2-yl)acetamide.
Figure 32B:
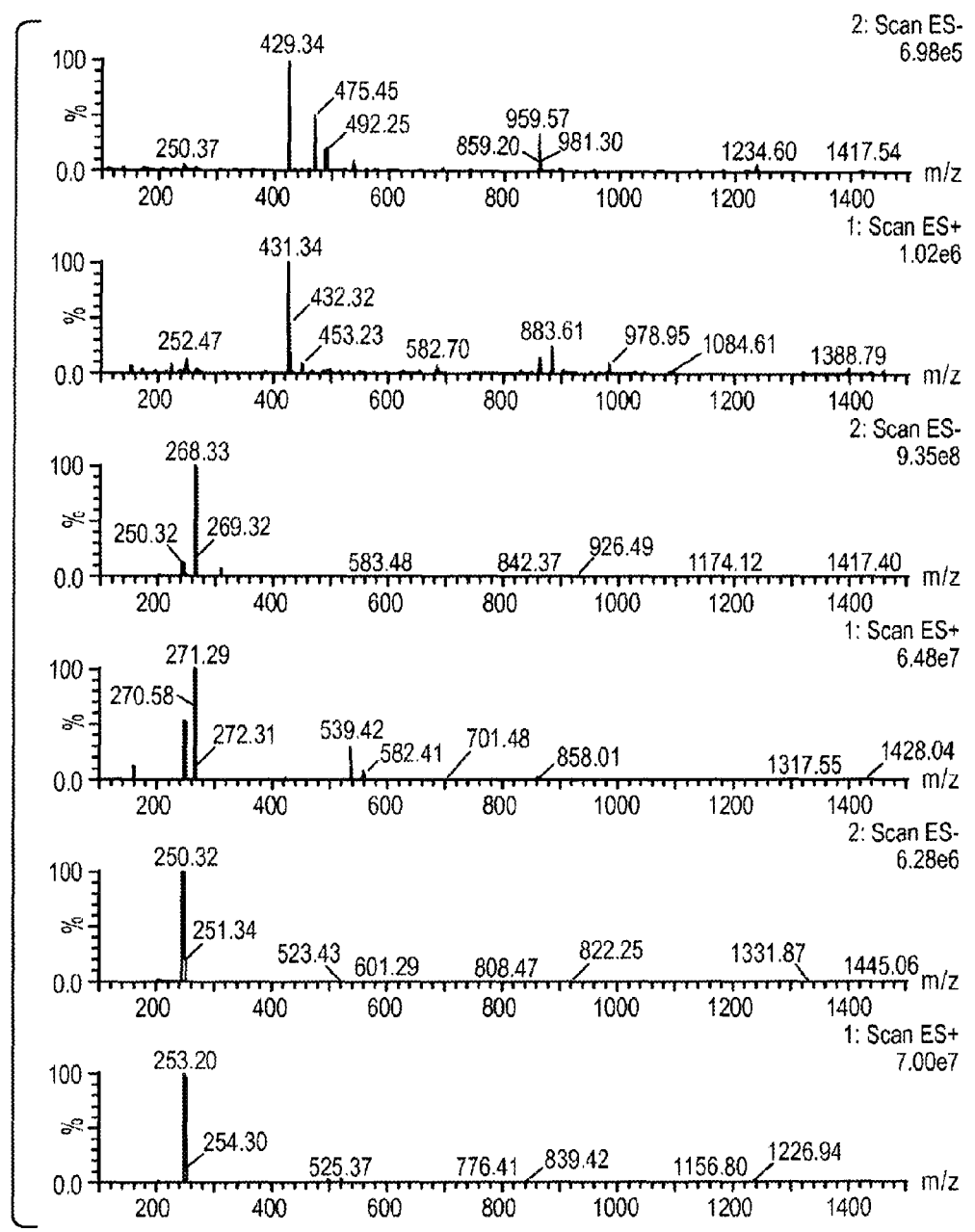
Figure 32C:
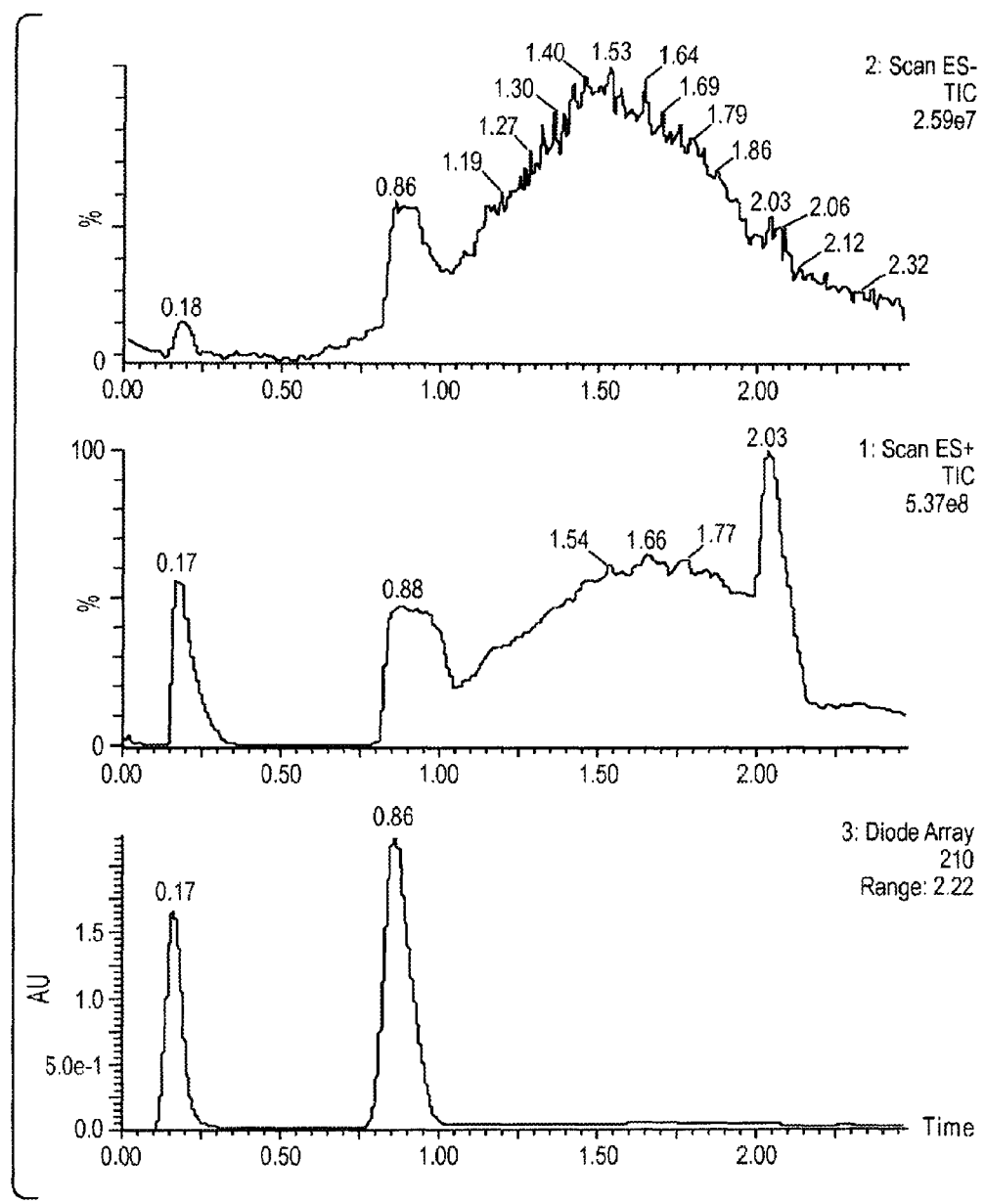
Figure 32D:
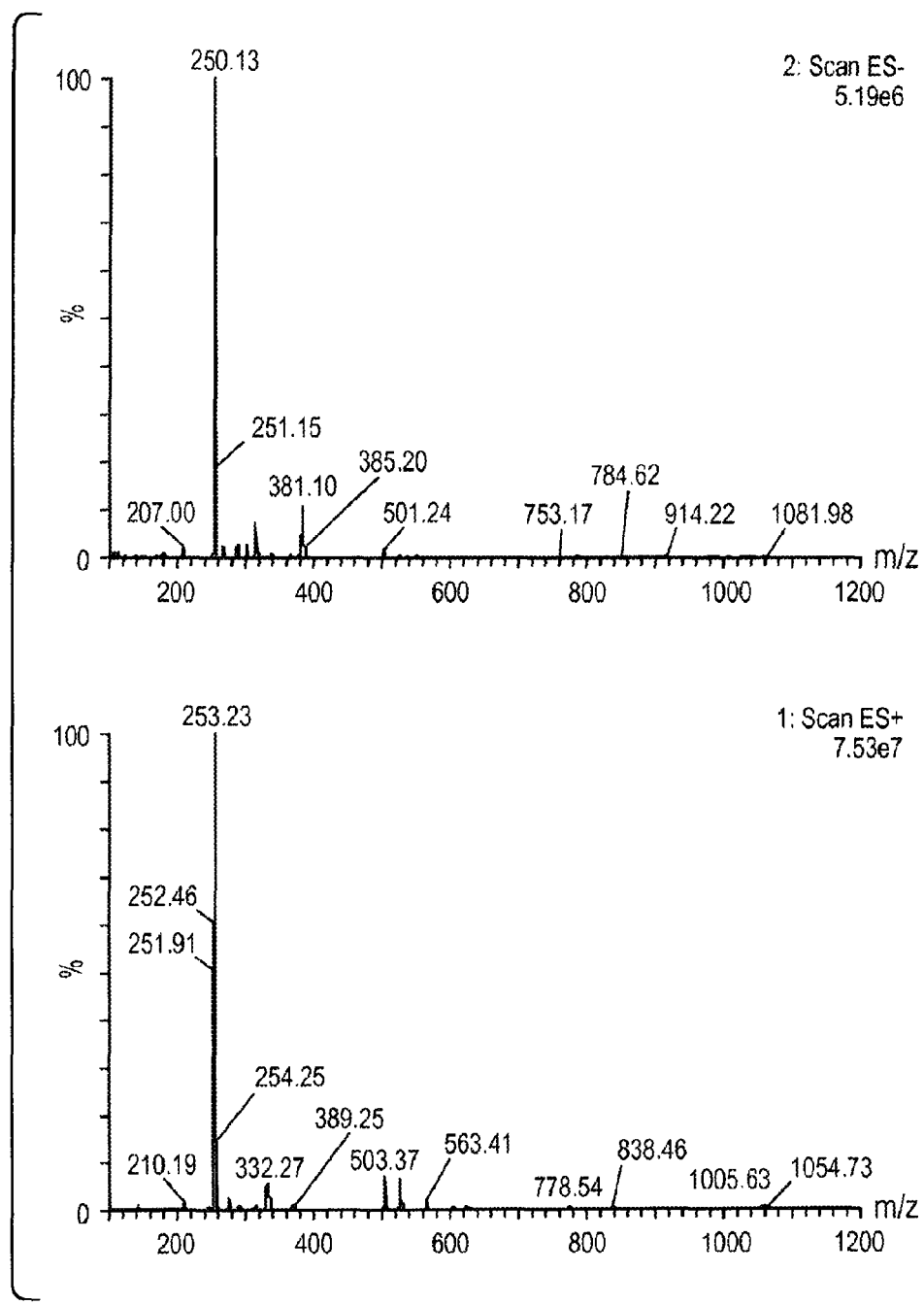

Analytical data were obtained on the product: the XRPD pattern was as shown in FIG. 30, the $^1$H-NMR spectrum was as shown in FIG. 31, and the LC/MS data was as shown in FIG. 32.

The analytical data obtained on the product indicate that it is a mixture of amorphous tacedinaline and N-(4-(1-H-benzo[d]imidazol-2-yl)acetamide.

Example 15

Synthesis of Crystalline Tacedinaline Form A

Synthesis of tert-butyl(2-aminophenyl)carbamate

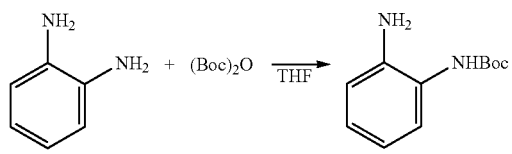 [SMILES: "(Boc)2O" ; Nc1ccccc1N ; CC(C)(C)OC(=O)Nc1ccccc1N ; "THF"]

To a 1 L round-bottom flask, o-phenylenediamine (50.8 g, 0.47 mol) and THF (500 mL) were added under N$_2$. To a 500 mL flask, (Boc)$_2$O (102.5 g, 0.47 mol) and THF (150 mL) were added under N$_2$ and stirred to dissolve. The (Boc)$_2$O solution was transferred to an addition funnel and added dropwise into the diamine solution. The reaction mixture was stirred for 18 hours at room temperature. A total of 620 mL THF was removed from the reaction mixture under reduced pressure. EtOAc (50 mL) and heptane (400 mL) were added, and the resultant slurry was stirred for 1 hour at room temperature. The solid was filtered and washed with heptane (2×50 mL). Drying in vacuo at 38° C. for 4 hours afforded the product tert-butyl (2-aminophenyl)carbamate (69.3 g, 71%, 97.3% HPLC purity) as a white solid.

$^1$HNMR (400 Hz, d$^6$-DMSO) δ: 8.29 (s, 1H), 7.17 (d, J=7.6 Hz, 1H), 6.83 (app dt, J=1.2 Hz, 7.6 Hz, 1H), 6.68 (dd, J=1.2 Hz, 8 Hz, 1H), 6.52 (app dt, J=1.2 Hz, 7.6 Hz, 1H), 4.83 (s, 2H), 1.46 (s, 9H).

Synthesis of tert-butyl (2-(4-acetamidobenzamido)phenyl)carbamate

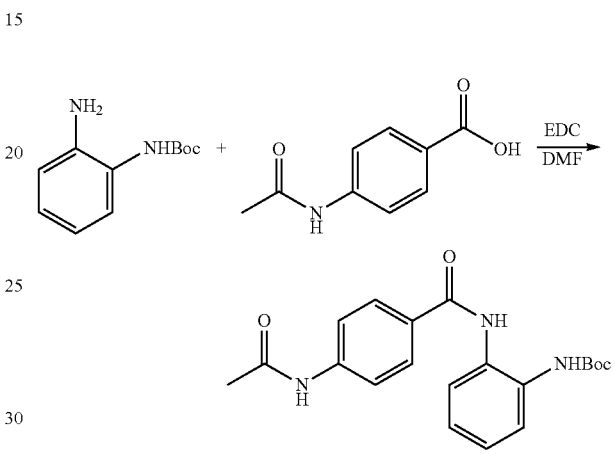

To a 1 L round-bottom flask, were added 4-acetamidobenzoic acid (21.7 g, 122 mmol), tert-butyl (2-aminophenyl)carbamate (23.0 g, 111 mmol), and DMF (90 mL). The mixture was stirred to dissolve under N$_2$, before EDC (27.6 g, 144 mmol) was added in one portion. The reaction mixture was stirred for 2 h, and water (270 mL) was added and stirred for 2 h. The precipitates were filtered, washed with water (2×45 mL) and heptane (2×45 mL). The filter cake was dried at 40° C. in vacuo for 16 h to afford tert-butyl (2-(4-acetamidobenzamido) phenyl)carbamate (31.8 g, 78% yield, 90.6% HPLC purity) as a white solid.

$^1$HNMR (400 Hz, d$^6$-DMSO) δ: 10.27 (s, 1H), 9.76 (s, 1H), 8.70 (bs, 1 h), 7.91 (d, J=8.8 Hz, 2H), 7.73 (d, J=8.8 Hz, 2H), 7.55-7.51 (m, 2H), 7.22-7.13 (m, 2H), 2.10 (s, 3H), 1.45 (s, 9H).

Synthesis of TFA Salt:
4-acetamido-N-(2-aminophenyl)benzamide trifluoroacetate Salt

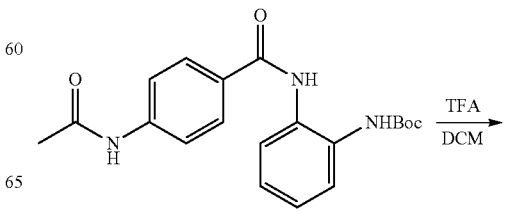

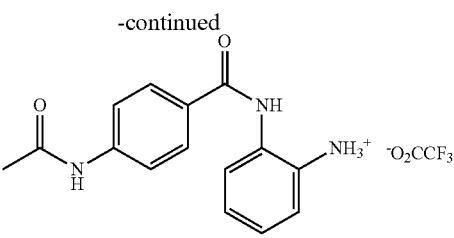

To a 1 L round-bottom flask, were added tert-butyl(2-(4-acetamidobenzamido) phenyl)carbamate (31.8 g, 86.2 mmol), DCM (160 mL) and TFA (95 mL). The reaction mixture was stirred for 2 hours before concentrating in vacuo. EtOH (95 mL) was added and concentrated in vacuo to further reduce the amount of residual TFA. MTBE (320 mL) was added, and the suspension was stirred for 2 hours. The solids were filtered, washed with MTBE (2×60 mL), and dried at 40° C. in vacuo for 18 hours to get 4-acetamido-N-(2-aminophenyl)benzamide trifluoroacetate salt (32.6 g, 99% yield, 92.2% HPLC purity).

$^1$HNMR (400 Hz, d$^6$-DMSO) δ: 10.28 (s, 1H), 10.07 (s, 2H), 7.98 (d, J=8.8 Hz, 2H), 7.73 (d, J=8.4 Hz, 2H), 7.34 (dd, J=1.2 Hz, 8.0 Hz, 1H), 7.24-7.14 (m, 2H), 7.09 (t, J=8.0 Hz, 1H), 2.10 (s, 3H). MS (ESI+): m/z 271.2 [M+H]$^+$.

Synthesis of Crystalline Tacedinaline Free Base Form B

The dried solid of 4-acetamido-N-(2-aminophenyl)benzamide trifluoroacetate salt was suspended in a solution of 1:1 EtOH:H2O (320 mL). Saturated NaHCO$_3$ solution (100 mL) was added slowly to adjust the pH to 8. The resultant slurry was stirred for 1.5 hours. The precipitates were filtered and washed with water (2×60 mL). After drying at 40° C. in vacuo for 16 h, 4-acetamido-N-(2-aminophenyl)benzamide (21.3 g, 92% yield, 97.0% HPLC purity) was isolated as crystalline Form B (white solid).

$^1$HNMR (400 Hz, d$^6$-DMSO) δ: 10.22 (s, 1H), 9.58 (s, 1H), 7.94 (d, J=8.8 Hz, 2H), 7.70 (d, J=8.8 Hz, 2H), 7.16 (dd, J=1.2 Hz, 8.0 Hz, 1H), 6.97 (app dt, J=1.6 Hz, 8.4 Hz, 1H), 6.79 (dd, J=1.2 Hz, 8.0 Hz, 1H), 6.6 (app dt, J=1.6 Hz, 8.4 Hz, 2H), 4.90 (s, 2H), 2.10 (s, 3H).

Synthesis of Crystalline Tacedinaline Free Base Form A

A sample of 2.0098 g crystalline tacedinaline Forms B and D was placed in 50 mL round bottom flask, and 20 mL of 95:5 EtOH/water added. The sample was placed in a 70° C. water bath and allowed to warm up. After 10 minutes, slurry of solid remains. The sample was seeded with 60.3 mg (3%) Form A. A reflux condenser was attached and the slurry was allowed to stir magnetically at 70° C. for 3 hours. The bath was then cooled to 20° C. The cooling process took 1 hour. The sample was then allowed to stir at 20° C. for 1 hour. The slurry was collected by vacuum filtration, and the solids were placed in a vacuum desiccator at 40° C. for 18 hours. The resulting product was isolated as Form A (white solid, 91.8% yield).

$^1$HNMR (500 Hz, d$^6$-DMSO) δ: 10.21 (s, 1H), 9.56 (s, 1H), 7.94 (d, J=9 Hz, 2H), 7.69 (d, J=6 Hz, 2H), 7.15 (d, J=6, 1H), 6.96 (t, J=9 Hz, 1H), 6.78 (d, J=9 Hz, 1H), 6.59 (d, J=6 Hz, 1H), 4.80 (s, 2H), 2.08 (s, 3H)

Example 16

Bioavailability Study of Crystalline Tacedinaline Form A

A study was performed to determine the pharmacokinetics parameters and bioavailability of Tacedinaline Form A in Sprague-Dawley Rats, following a single intravenous injection (IV) and oral administration (PO).

Formulation: IV formulation: The test article was dissolved in 10% DMSO/45% PEG400/45% Saline to yield a final concentration of 0.5 mg/ml for intravenous injection. PO formulation: The test article was suspended in 0.5% methylcellulose in water to yield a final concentration of 0.2 mg/ml for oral administration.

Collection Intervals: Three rats in each group were used for blood collection at each time point: Groups 1 and 2: Pre-dose and post-dose (5 min, 15 min, 30 min, 1 hour, 2 hours, 4 hours, 6 hours, 8 hours, and 24 hours).

Analysis Procedure: The PK blood samples were centrifuged at approximately 8000 rpm for 6 minutes at 2-8° C. and the resulting plasma separated and stored frozen at approximately −80° C. (following separation, the plasma may be initially placed on ice prior to being stored in the −80° C. freezer). All the plasma samples were labeled with detailed information such as study number, animal number, matrix, time points of collection and date of collection.

Pharmacokinetics Analysis: A standard set of parameters including Area Under the Curve (AUC$_{(0-t)}$ and AUC$_{(0-\infty)}$), elimination half-life (T$_{1/2}$), maximum plasma concentration (C$_{max}$), time to reach maximum plasma concentration (T$_{max}$), clearance (CL), and volume of distribution (V$_z$) was calculated using noncompartmental analysis modules in FDA certified pharmacokinetic program WinNonlin Professional v6.1 (Pharsight, USA). Further, the bioavailability was estimated using the following formula:

$$F = \frac{AUC_{(0-\infty)(PO)} \times Dose_{IV}}{AUC_{(0-\infty)(IV)} \times Dose_{PO}} \times 100\%$$

Figure 41:
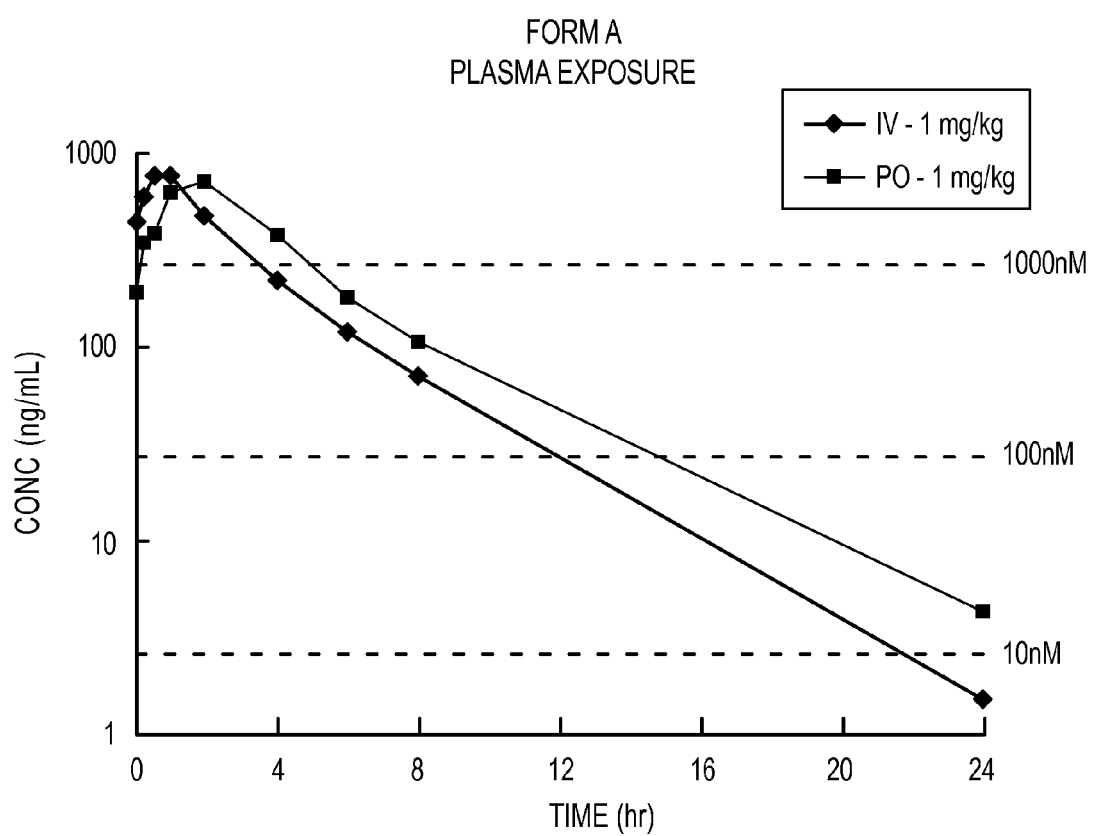
FIG. 41 shows the Plasma Concentration-Time Curve of crystalline tacedinaline Form A in Sprague-Dawley rats following intravenous injection and oral administration at 1 mg/kg.

The results are summarized below in Tables 16 (IV) and 17 (PO), which show selected plasma pharmacokinetics parameters of crystalline tacedinaline Form A in Sprague-Dawley rats following intravenous injection and oral administration at 1 mg/kg, as well as in FIG. 41 which shows the plasma concentration-time curve of the same. This study demonstrates that crystalline tacedinaline Form A shows 100% bioavailability in rats.

TABLE 16

| | IV - 1 mg/kg | | | | | | | | |
|---|---|---|---|---|---|---|---|---|---|
| Animal No. | AUC$_{(0-t)}$ µg/L * hr | AUC$_{(0-\infty)}$ µg/L * hr | MRT$_{(0-\infty)}$ hr | t$_{1/2}$ hr | T$_{max}$ hr | V$_z$ L/kg | CL L/hr/kg | C$_{max}$ µg/L | F % |
| 1 | 3093.33 | 3098.83 | 3.46 | 2.81 | 0.50 | 1.31 | 0.32 | 799.48 | — |
| 2 | 3005.79 | 3011.53 | 3.57 | 2.82 | 0.50 | 1.35 | 0.33 | 714.90 | — |
| Mean | 3049.56 | 3055.18 | 3.52 | 2.81 | 0.50 | 1.33 | 0.33 | 757.19 | — |

TABLE 17

| | PO - 1 mg/kg | | | | | | | | |
|---|---|---|---|---|---|---|---|---|---|
| Animal No. | $AUC_{(0-t)}$ µg/L * hr | $AUC_{(0-\infty)}$ µg/L * hr | $MRT_{(0-\infty)}$ hr | $t_{1/2}$ hr | $T_{max}$ hr | $V_z\_F$ L/kg | $CL\_F$ L/hr/kg | $C_{max}$ µg/L | F % |
| 1 | 3697.50 | 3731.83 | 4.60 | 3.81 | 2.00 | 1.47 | 0.27 | 686.56 | 122.15 |
| 2 | 4016.76 | 4026.28 | 4.06 | 2.90 | 2.00 | 1.04 | 0.25 | 781.22 | 131.79 |
| Mean | 3857.13 | 3879.06 | 4.33 | 3.35 | 2.00 | 1.25 | 0.26 | 733.89 | 126.97 |

$AUC_{(0-t)}$ Area under the curve from the time of dosing to the last measurable concentration
$AUC_{(0-\infty)}$ Area under the curve from the time of dosing extrapolated to infinity, based on the last observed concentration
CL  Total body clearance, CL = Dose/AUC
$C_{max}$  Maximum observed concentration, occurring at $T_{max}$
F  Bioavailability
$MRT_{(0-\infty)}$ Mean residence time from the time of dosing to infinity
$T_{max}$  Time of maximum observed concentration
$T_{1/2}$  Terminal half-life = $\ln(2)/\lambda z$
$V_z$  Volume of distribution based on the terminal phase

What is claimed is:

1. A Crystalline 4-(acetylamino)-N-(2-aminophenyl)-benzamide Form A.

2. A pharmaceutical composition comprising crystalline 4-(acetylamino)-N-(2-aminophenyl)-benzamide Form A according to claim 1.

3. The pharmaceutical formulation comprising crystalline 4-(acetylamino)-N-(2-aminophenyl)-benzamide Form A according to claim 1, further comprising at least one pharmaceutically acceptable carrier.

4. The pharmaceutical formulation according to claim 3, which is a solid unit dosage form.

* * * * *